US012706196B2

(12) United States Patent
Shiramoto

(10) Patent No.: US 12,706,196 B2
(45) Date of Patent: Aug. 11, 2026

(54) INFORMATION TERMINAL, RECORDING MEDIUM, INFORMATION PROCESSING SYSTEM, AND INFORMATION PROCESSING METHOD

(71) Applicant: EVALUATION INFORMATION RESEARCH INSTITUTE, LIMITED, Tokyo (JP)

(72) Inventor: Chikako Shiramoto, Tokyo (JP)

(73) Assignee: EVALUATION INFORMATION RESEARCH INSTITUTE, LIMITED, Tokyo (JP)

( * ) Notice: Subject to any disclaimer, the term of this patent is extended or adjusted under 35 U.S.C. 154(b) by 480 days.

(21) Appl. No.: 18/004,302

(22) PCT Filed: Jun. 17, 2021

(86) PCT No.: PCT/JP2021/023050
§ 371 (c)(1),
(2) Date: Jan. 5, 2023

(87) PCT Pub. No.: WO2022/009643
PCT Pub. Date: Jan. 13, 2022

(65) Prior Publication Data

US 2023/0253084 A1 Aug. 10, 2023
US 2024/0321419 A2 Sep. 26, 2024

(30) Foreign Application Priority Data

Jul. 6, 2020 (JP) ................................ 2020-116661
Sep. 18, 2020 (JP) ................................ 2020-157567
Feb. 15, 2021 (JP) ................................ 2021-022175

(51) Int. Cl.
*G16H 20/00* (2018.01)
*G06F 40/40* (2020.01)
*G06Q 10/087* (2023.01)

(52) U.S. Cl.
CPC ............ *G16H 20/00* (2018.01); *G06F 40/40* (2020.01); *G06Q 10/087* (2013.01)

(58) Field of Classification Search
None
See application file for complete search history.

(56) References Cited

U.S. PATENT DOCUMENTS 11,386,890 B1 * 7/2022 Fan ......................... G06F 40/30
2016/0210764 A1 7/2016 Gomi et al.
(Continued)

FOREIGN PATENT DOCUMENTS

JP H394374 A 4/1991
JP H11272710 A 10/1999
(Continued)

*Primary Examiner* — Nicole A K Schmieder
(74) *Attorney, Agent, or Firm* — HAUPTMAN HAM, LLP

(57) ABSTRACT

In a life information system: a user specifies, in advance, a character string expressing an intent; a sentence relating to details of an article from purchase to consumption is received, the sentence having been input to an information terminal by means of speech or the like by the user in accordance with a rule for registering a nickname serving as a keyword for identifying the article; the intent of the user is identified from the sentence, and the nickname of the article is extracted; a table of a type corresponding to the intent of the user is selected from tables of different types storing user-specific data of a database; and the nickname of the article extracted from the sentence is associated with the nickname of the article registered for each user of the table.

33 Claims, 22 Drawing Sheets

(56) References Cited

U.S. PATENT DOCUMENTS

| | | | | |
|---|---|---|---|---|
| 2017/0235889 | A1* | 8/2017 | Mian | G16H 70/60 702/179 |
| 2017/0358304 | A1 | 12/2017 | Castillo Sanchez et al. | |
| 2019/0164556 | A1* | 5/2019 | Weber | G10L 15/34 |
| 2021/0042724 | A1* | 2/2021 | Rathod | G07G 1/0054 |

FOREIGN PATENT DOCUMENTS

| | | | | |
|---|---|---|---|---|
| JP | 2007249375 | A | * | 9/2007 |
| JP | 2009140167 | A | | 6/2009 |
| JP | 201066811 | A | | 3/2010 |
| JP | 2013191137 | A | | 9/2013 |
| JP | 2017157198 | A | | 9/2017 |
| JP | 20185536 | A | | 1/2018 |
| JP | 201814086 | A | | 1/2018 |
| JP | 201921268 | A | | 2/2019 |
| WO | 2015029801 | A1 | | 3/2015 |

* cited by examiner

Inventory list by class

CLASS carbohydrate

| Store | Brand | Product name | Alias | Acquisition date yyyy/mm/dd | Target consumption deadline yyyy/mm/dd | Spot | Current | Urgent | D1 | D2 | D3 | Finished | Spare | Purchase |
|---|---|---|---|---|---|---|---|---|---|---|---|---|---|---|
| A *** | *** | chinese noodle | | 2020/5/31 | 2020/6/6 | refrigerator | ☐ | ☐ | ☐ | ☑ | ☐ | ☐ | ☐ | ☑ |
| K *** | company B | pasta | | 2020/4/12 | 2020/7/21 | shelf | ☐ | ☐ | ☐ | ☐ | ☐ | ☐ | ☐ | ☐ |
| T *** | haruyutaka | flour | haruyutaka | 2020/5/3 | 2020/9/30 | shelf | ☐ | ☐ | ☐ | ☐ | ☐ | ☐ | ☐ | ☐ |
| E *** | company J | bagel | J bagel | 2020/5/22 | 2020/6/21 | freezer | ☐ | ☐ | ☐ | ☐ | ☑ | ☐ | ☐ | ☐ |

vegetables>> processed food>>

FIG. 6A

Inventory list by target consumption deadline

| Store | Brand | Product name | Alias | Acquisition date yyyy/mm/dd | Target consumption deadline yyyy/mm/dd | Spot | Current | Urgent | D1 | D2 | D3 | Finished | Spare | Purchase |
|---|---|---|---|---|---|---|---|---|---|---|---|---|---|---|
| K *** | company F silken tofu | tofu | silken tofu | 2020/5/31 | 2020/6/2 | refrigerator | ☐ | ☑ | ☑ | ☐ | ☐ | ☐ | ☐ | ☐ |
| K *** | brand G | pork | | 2020/5/30 | 2020/6/2 | refrigerator | ☐ | ☑ | ☑ | ☐ | ☐ | ☐ | ☐ | ☐ |
| K *** | | cabbage | | 2020/5/31 | 2020/6/6 | refrigerator | ☐ | ☐ | ☐ | ☑ | ☐ | ☐ | ☐ | ☐ |
| A *** | *** | chinese noodle | | 2020/5/31 | 2020/6/6 | refrigerator | ☐ | ☐ | ☐ | ☑ | ☐ | ☐ | ☐ | ☑ |
| E *** | company J | bagel | J bagel | 2020/5/22 | 2020/6/21 | freezer | ☐ | ☐ | ☐ | ☐ | ☑ | ☐ | ☐ | ☐ |

FIG. 6B

INPUT SCREEN mm/dd 24h clock

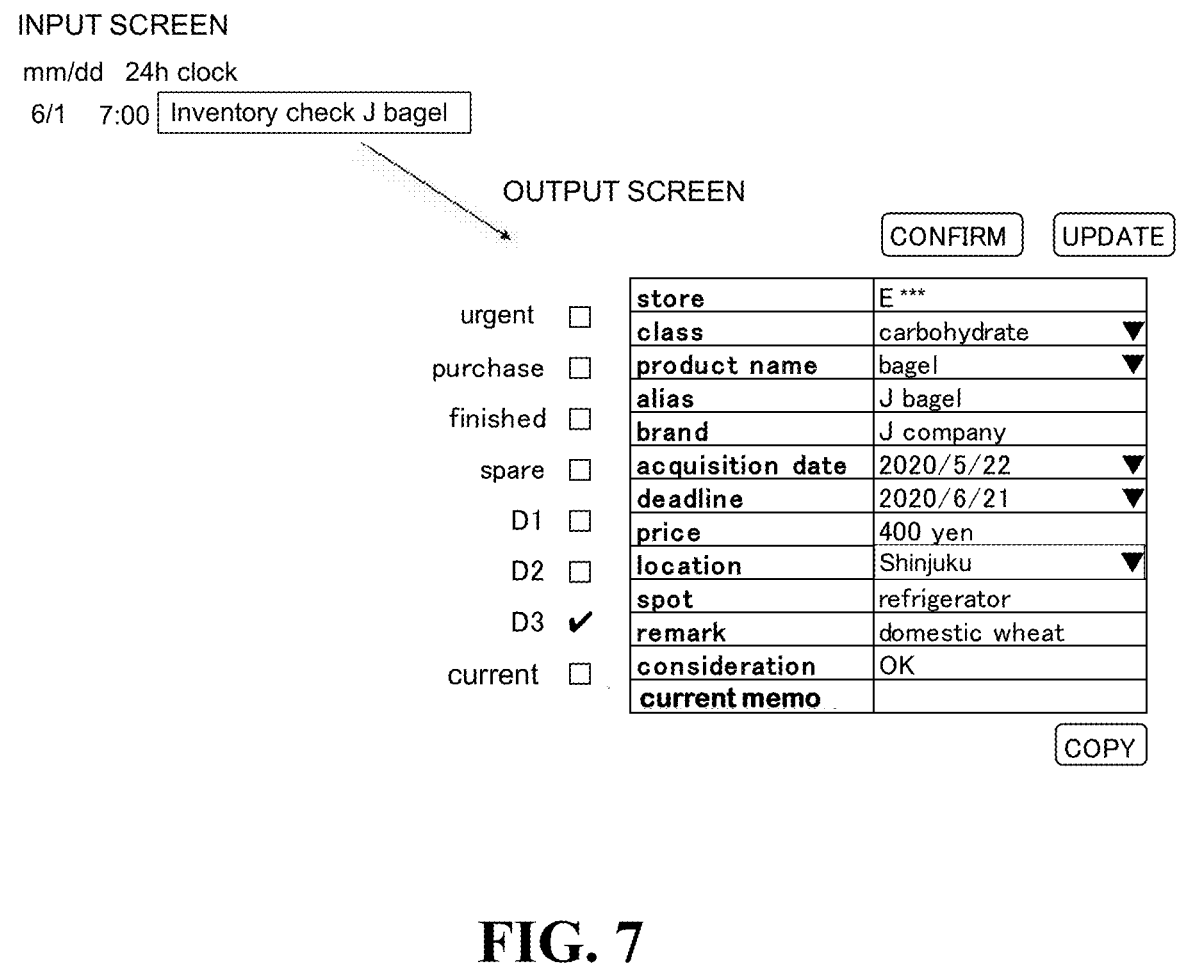

6/1 7:00 Inventory check J bagel

OUTPUT SCREEN

CONFIRM UPDATE urgent ☐
purchase ☐
finished ☐
spare ☐
D1 ☐
D2 ☐
D3 ✔
current ☐

| store | E *** |
|---|---|
| class | carbohydrate ▼ |
| product name | bagel ▼ |
| alias | J bagel |
| brand | J company |
| acquisition date | 2020/5/22 ▼ |
| deadline | 2020/6/21 ▼ |
| price | 400 yen |
| location | Shinjuku ▼ |
| spot | refrigerator |
| remark | domestic wheat |
| consideration | OK |
| current memo | |

COPY

FIG. 7

| Product name | Brand |
| --- | --- |
| soy sauce | brand X |
| miso | brand Y |
| green onions | |
| mayonnaise | brand Z |

E Example of consumption status of article items and transition of possibilities % depending on whether there was a problem

| Consumption Date | Consumption Time | Article Item | Before Consumption Possibility% | Within 6 hours Problem? | After 6 hours Possibility% | Possibility% Update Status |
|---|---|---|---|---|---|---|
| 12/12 | 6:55 | Article Item 1 | 50% | No | 0% | Before Update |
| | | Article Item 2 | 0% | No | 0% | Latest |
| | 12:00 | Article Item 3 | 20% | Yes | 27% | Latest |
| | | Article Item 4 | 50% | Yes | 67% | Before Update |
| | | Article Item 5 | 70% | Yes | 94% | Latest |
| | | Article Item 6 | 55% | Yes | 74% | Latest |
| | | Article Item 7 | 65% | Yes | 87% | Latest |
| | | Article Item 8 | 30% | Yes | 40% | Before Update |
| | 17:30 | Article Item 1 | 0% | Yes | 0% | Latest |
| | | Article Item 4 | 67% | Yes | 93% | Latest |
| | | Article Item 8 | 40% | Yes | 56% | Latest |
| | | Article Item 9 | 95% | Yes | 131% | Latest |
| | | Article Item 10 | 10% | Yes | 14% | Latest |
| | | Article Item 11 | 50% | Yes | 69% | Latest |

Replaced by 100% if the calculation results exceed 100%

FIG. 11

F Possibility % by Article Item for Physical Condition Events

| Physical Condition Event | | | | Possibility % of the Article Items | | | | | | | | |
|---|---|---|---|---|---|---|---|---|---|---|---|---|
| Date | Time | Level | Conversion Value | 3 | 4 | 5 | 6 | 7 | 8 | 9 | 10 | 11 |
| 12/12 | 13:00 | 3 | 5.4 | 27% | 93% | 94% | 74% | 87% | 56% | | | |
| 12/12 | 14:10 | 4 | 12.8 | 27% | 93% | 94% | 74% | 87% | 56% | | | |
| 12/12 | 18:20 | 2 | 1.6 | | 93% | | | | 56% | 100% | 14% | 69% |
| 12/12 | 21:15 | 1 | 0.2 | | 93% | | | | 56% | 100% | 14% | 69% |

G Example of Calculation of Scores by Article Item for Physical Condition Events

| Physical Condition Event | | | | Score of the Article Item | | | | | | | | |
|---|---|---|---|---|---|---|---|---|---|---|---|---|
| Date | Time | Level | Conversion Value | 3 | 4 | 5 | 6 | 7 | 8 | 9 | 10 | 11 |
| 12/12 | 13:00 | 3 | 5.4 | 0.3 | 1.2 | 1.2 | 0.9 | 1.1 | 0.7 | | | |
| 12/12 | 14:10 | 4 | 12.8 | 0.8 | 2.8 | 2.8 | 2.2 | 2.6 | 1.7 | | | |
| 12/12 | 18:20 | 2 | 1.6 | | 0.4 | | | | 0.3 | 0.5 | 0.1 | 0.3 |
| 12/12 | 21:15 | 1 | 0.2 | | 0.1 | | | | 0.0 | 0.1 | 0.0 | 0.0 |
| | | Average values | | **0.6** | **1.1** | **2.0** | **1.6** | **1.8** | **0.7** | **0.3** | **0.0** | **0.2** |

FIG. 12

OUTPUT SCREEN

| DATE | TIME | CONTENT | CONSIDERATION |
|---|---|---|---|
| 2019/6/17 | 13:00 | Store B lunch box containing mackerel | Beware of freshness |
| 2019/6/17 | 14:00 | ⇒level 0.9 | |
| 2019/6/17 | 15:00 | ⇒level 2.4 | |
| 2019/8/8 | 12:30 | Store B lunch box containing mackerel | Beware of freshness |
| 2019/8/8 | 14:10 | ⇒level 1.2 | |
| 2019/8/8 | 15:30 | ⇒level 2.8 | |
| 2019/11/23 | 19:00 | Store A grilled Japanese mackerel | |
| 2019/11/23 | 20:00 | ⇒level 2.5 | |

INFORMATION TERMINAL, RECORDING MEDIUM, INFORMATION PROCESSING SYSTEM, AND INFORMATION PROCESSING METHOD

RELATED APPLICATIONS

The present application is National Phase of International Application Number PCT/JP2021/023050, filed Jun. 17, 2021, and claims priority based on Japanese Patent Application Nos. 2020-116661, filed Jul. 6, 2020, 2020-157567, filed Sep. 18, 2020 and 2021-022175, filed Feb. 15, 2021.

TECHNICAL FIELD

The present disclosure relates to information terminals, recording media, information processing systems, and information processing methods for effectively utilizing information.

BACKGROUND ART

In recent years, the functions of mobile information terminals such as smartphones have improved, and an environment has been established in which consumers can easily and quickly input various types of information using images, voice, and other methods.

In such an environment, services have emerged to provide health guidance by obtaining information on dietary contents and health condition from consumers. There are also systems that allow consumers to manage information on products such as foods using portable information terminals.

Patent Literature 1 discloses, as a method of operating an automatic assistant, a technique in which a natural language processing module presumes a user's intention from a text string.

Patent Literature 2 discloses a technique for obtaining nutrition information based on meal information collected by a method of selecting sentences, images, or menus, and further obtaining related information on health by means of lifestyle habit questionnaires, biometric log information, and other methods, and transmitting advice information after analyzing such information.

CITATION LIST

Patent Literatures

Patent Literature 1: Japanese Unexamined Patent Application Publication No. 2018-14086

Patent Literature 2: Japanese Unexamined Patent Application Publication No. 2017-157198

SUMMARY OF THE INVENTION

Technical Problem

With the conventional system, it was not easy for general consumers to use databases on a daily basis to improve the comfort of their lives and reduce waste.

Commodity information can be input to an information terminal by recognizing images or barcodes by a simple operation performed the consumer. However, if images have a similar appearance, there is a problem that even if the contents are different from each other, the product information is recognized as the same product. In addition, products that can be recognized by a barcode are limited, and those with no barcode cannot be handled.

By processing natural language using voice input or other means, there is a possibility that many types of information can be handled more flexibly than by other methods. However, there is a problem that a conventional method of mechanically analyzing natural language sentences and capturing the user's intentions may be inaccurate. The problems to be solved by the present invention include, but are not limited to, the problems described above.

Solution to Problem

A life information system as an aspect of the present disclosure is capable of analyzing sentences in natural language and inferring the user's intentions by setting certain rules in advance for the method of entering sentences related to articles that users acquire and consume on their own, while employing an input method using sentences that allow free content to be entered. This system therefore updates the database on the user's own articles based on a more accurate analysis of the sentence than a system that employs a method of extracting words entered without any rules.

Specifically, the life information system has rules to specify, in advance, character strings that express the user's intention to direct actions to the database, and to register, in the database in advance, nicknames, which are keywords to identify articles. According to these rules, the system receives a sentence about articles entered by the user, identifies the user's intention by recognizing the specified character string for directing the action to the database in the sentence, extracts the nicknames of the articles from the remaining character string, and selects a table of a type corresponding to the user's intention from tables of types containing user-specific data in the database. Then, by matching the nicknames of the articles extracted from these sentences with their nicknames registered for each user in the table, the user's own data on the articles can be extracted, the database can be updated in one operation, and a notification can be sent to the user's information terminal.

BRIEF DESCRIPTION OF DRAWINGS

FIG. 6A is a display example of a screen of an inventory list grouped by class.

FIG. 6B is a display example of a screen of a target consumption deadline order inventory list.

FIG. 7 is a display example of a screen for confirming details of inventory.

FIG. 11 is a diagram showing an example of transition of possibilities % due to the consumption status of article items, and the presence or absence of problems.

FIG. 12 is a diagram illustrating an example of the calculation of possibilities % and scores for each article item.

DESCRIPTION OF EMBODIMENTS

Figure 1:
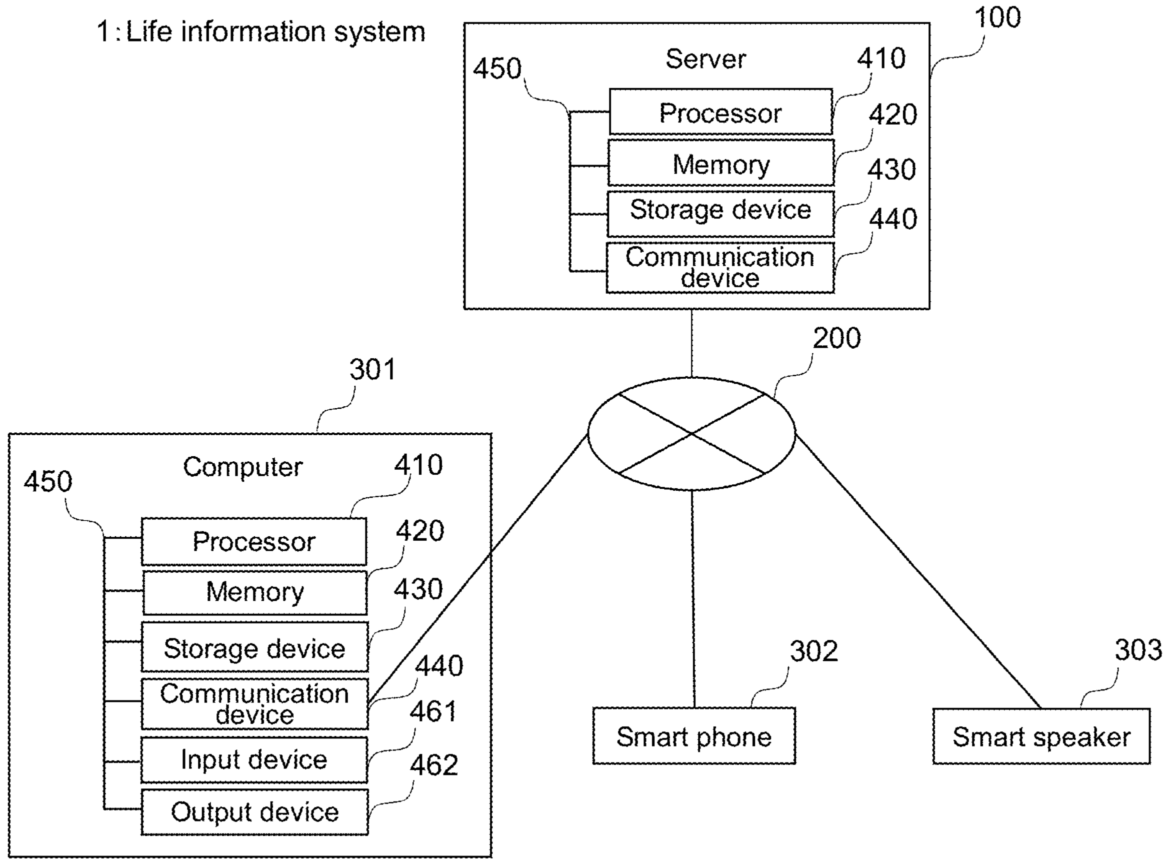
FIG. 1 is a hardware configuration diagram of a life information system.

Hereinafter, embodiments of the present disclosure will be described in detail with reference to the accompanying drawings. FIG. 1 is a hardware configuration diagram of the life information system 1, which is an information processing system according to an embodiment of the present disclosure. As shown in the figure, the life information system 1 includes a server 100 and information terminals used by users, which are connected by a communication network 200 such as the internet or a wireless communication line. A computer 301, a smartphone 302, and a smart speaker 303 are illustrated as information terminals used by users. An information terminal 300 used by the user in FIG. 2 includes, in addition to these information terminals, electronic devices other than those illustrated in FIG. 1.

Figure 2:
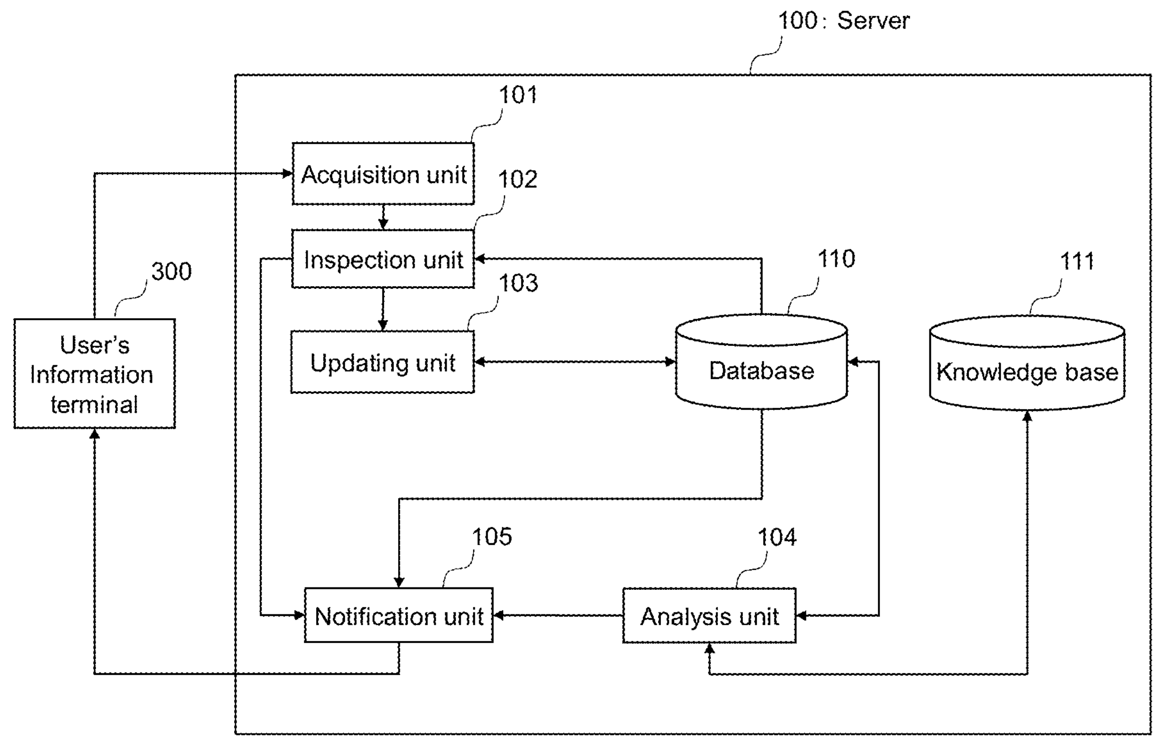
FIG. 2 is a block diagram of the life information system.

FIG. 2 is a block diagram of the life information system 1. An acquisition unit 101 receives data input from an information terminal 300 used by the user, the content of the data is analyzed by an inspection unit 102, and the analysis result is passed to an updating unit 103. The inspection unit 102 queries a database 110 for user-specific information necessary for inspecting the sentence during the inspection. The updating unit 103 updates the database 110 based on the information obtained from the inspection unit 102. An analysis unit 104 analyzes based on the data in the database 110 and a knowledge base 111, transmits the analysis result from a notification unit 105 to the information terminal 300 used by the user, and updates the data in the database 110 and the knowledge base 111 as necessary. The notification unit 105 transmits the input result recognized by the inspection unit 102 to the information terminal 300 used by the user, so that the user can confirm, add, or edit the input content. Note that when the input content from the user analyzed by the inspection unit 102 is only a request for displaying extracted data and is not for data update, the notification unit 105 directly receives the content of the user's request from the inspection unit 102, extracts data corresponding to the user's intention from the database 110, and transmits the data to the information terminal 300 used by the user. The server 100 includes a processor 410, a memory 420, a storage device 430, a communication device 440, a bus 450, and other devices. The information terminal 300 used by the user includes the processor 410, the memory 420, the storage device 430, the communication device 440, the bus 450, an input device 461, an output device 462, and other devices. Although FIG. 1 shows an example of components in the case of the computer 301 among the information terminal 300 used by the user, other types of information terminals 300 may have a similar configuration. The bus 450 performs information communication within the server 100 and the information terminal 300 used by the user. The communication device 440 is used as an interface for communication between the server 100 and the information terminal 300 used by the user via the communication network 200. The processor 410 reads programs or data from the storage device 430 or the communication device 440 into the memory 420, and executes various processes.

In the present embodiment, a case is assumed in which the life information system 1 is operated in the server 100 separately from the information terminal 300 used by the user, but the life information system 1 may be operated inside the information terminal 300 used by the user on the premise that the function of the knowledge base 111 is limited. The present invention also includes information processing methods and programs for implementing all or parts of the functions of the life information system 1, and such programs may not only be executed on the server, but may be downloaded to an information terminal from the network. Alternatively, the information may be stored in an information terminal in advance, or may be stored in a recording medium readable by an information terminal.

As described above, the results of input by the user to the information terminal 300 are processed through the communication network 200, an acquisition unit 101, an inspection unit 102, and if necessary, an updating unit 103 and an analysis unit 104. While the transmission of information to the information terminal 300 used by the user is processed through the notification section 105, in the following explanation, in some cases, such intermediate processes are omitted, and explanations are given as if the user directly operates the database 110 and the processing results are displayed on the information terminal 300. In addition, there are cases where it is not specified that the processing is performed by each part of the life information system 1. Even in such cases, the above intermediate processes are actually involved, but explanations of the processing that cannot be misunderstood are omitted below. It should be noted that in the sections below, where the scope is not specified and is described as "existing", this means that the data exists in the database 110.

Sentence input is a means for quick recording in the database 110, and can also be done by voice, typing on the information terminal 300 with a keyboard or touch panel, or various other input methods. The following description is mainly based on the premise that the user operates the smartphone 302 or the like while checking the screen.

Figure 8:
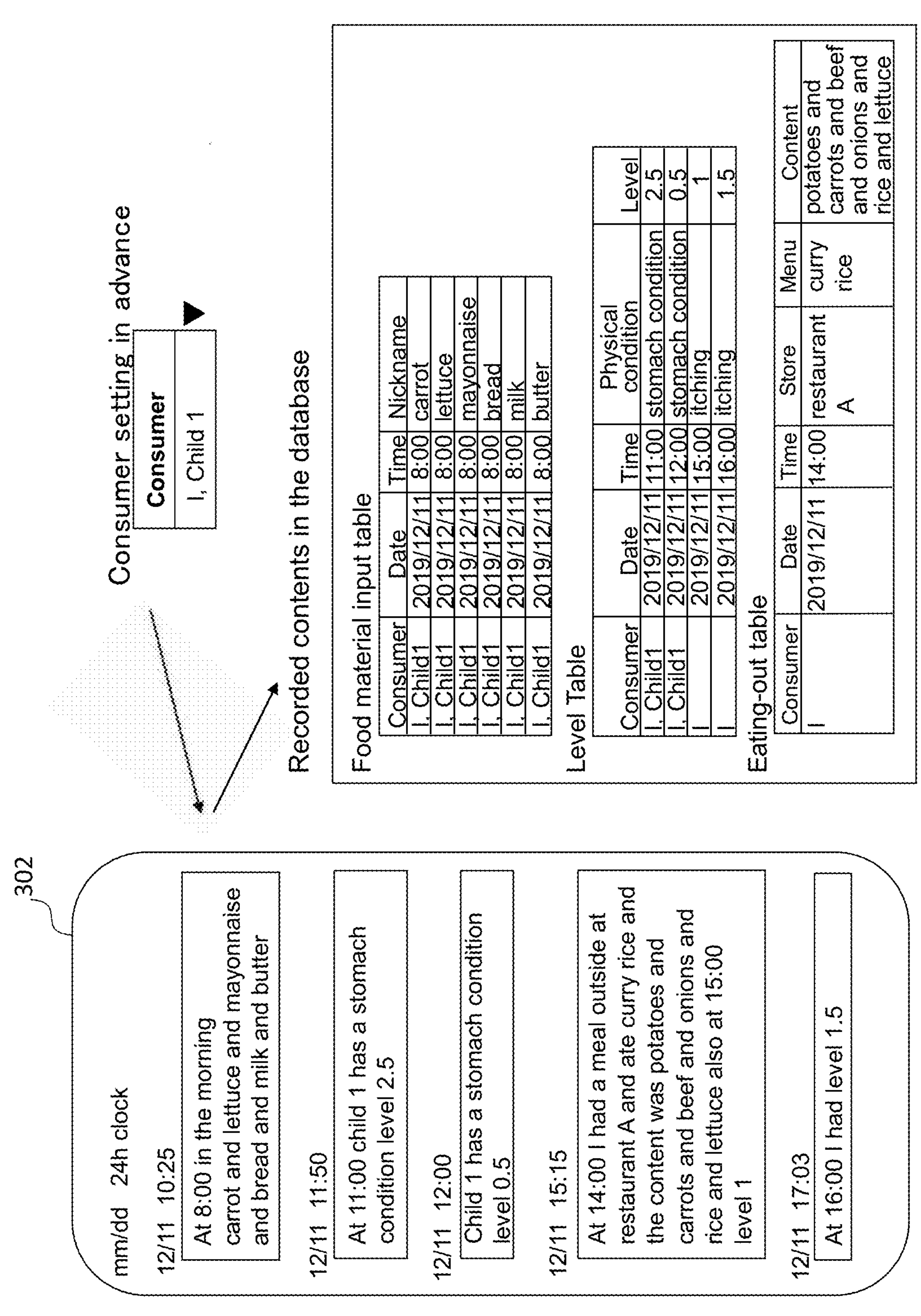
FIG. 8 is a diagram illustrating an example of a screen and processing related to the consumption of articles and physical condition.

FIG. 8 shows an example of the sentence input by displaying a portion on the screen of the smartphone 302 (hereinafter referred to as an "input box") in which text can be entered by sentences or other means, and the user can input in chronological order while confirming the input content. Also it is possible to prompt the user to confirm the contents before updating the database 110 for accuracy.

Before updating the database 110, the input sentence is analyzed by the inspection unit 102 and converted to be recorded in the database 110, and the result is displayed as a confirmation screen on the information terminal 300. When the content is confirmed by the user, the database 110 is updated. When the user does not have time to confirm, the input sentence may be recorded as it is so that the user can confirm it later, or an image such as a food item may be recorded in the information terminal 300 as a reminder record, and the user may input a sentence later on another occasion. Data may be transmitted from the information terminal 300 by e-mail or other means, and this invention can be used even in the case of the smart speaker 303 or the like, for example, where confirmation cannot be performed on the screen at the time of input. In the method in which the user selects representative options on the screen of the information terminal 300 one by one, it takes considerable effort to display and confirm them, and there is a problem that the corresponding options are not always available and the input contents may be inaccurate, but it is also possible to select the input contents from the pull-down menu on the screen of the information terminal 300, such as the computer 301 or the smartphone 302, or to freely input the contents one by one, without using a sentence.

In the case of sentence input, the acquired data is processed by the updating unit 103 via the acquisition unit 101 and the inspection unit 102. However, when the user directly inputs data item by item from the screen of the information terminal 300, the updating unit 103 directly processes the data from the acquisition unit 101 without going through the inspection unit 102.

In the present embodiment, general consumers are assumed to be the main users of the life information system 1, but people who support general consumer input in their home, or businesses that handle consumer goods such as restaurants or the like can also be assumed to be users. In addition, if the consumer who is the subject user of the life information system 1 does not directly enter data into the information terminal 300 by him/herself or if the content or method of input is insufficient, an intermediary may conduct a hearing from the subject consumer or may collect and edit the consumer's data from outside the life information system 1, and then the intermediary may input the data to the information terminal 300 as a user. Such a user may be related to the subject consumer, or may operate the life information system 1 as a business or support the use of the life information system 1 by consumers. The following describes the case where the user is also the subject consumer.

The life information system 1 is an information processing system for managing information on articles, and the articles that can be managed are not limited to foods, but also consumer articles such as clothes, cosmetics, supplements, and all other items around the user that affect his/her comfort of life. In the present embodiment, food items, which are particularly numerous and consumed on a daily basis, and therefore have a high need for control, are taken as examples and described.

General consumers repeatedly purchase and consume articles in their homes on a daily basis. In particular, since foods contain a wide variety of raw materials, it has been difficult for conventional methods to collect information in a way that allows us to ascertain even the differences in trace amounts of ingredients due to differences in the brands or the like of foods consumed on a daily basis. It is difficult for users to continuously keep daily records if not only a large number of product names but also raw materials, purchase stores, and related matters such as expiration dates cannot be input intuitively and quickly from an information terminal by a simple operation at the time of purchase, consumption and confirmation of the stock of foods or the like. In addition, it is difficult to perform an efficient and objective analysis by relying only on memory or by simply keeping a chronological record of the contents of one's diet and health condition in a diary or spreadsheet software. Also, questionnaires and biometric log information do not provide a timely and comprehensively grasp of changes in the level of physical condition felt by the consumer. Since it is difficult to grasp essential differences such as materials of articles in images, and barcodes cannot handle all articles, including those consumed when eating out and perishables, these methods may be used in a complementary manner, but in the present embodiment, the explanation is based on the premise of a sentence-based input method. It should be noted that in the present embodiment, even if articles are stored by general consumers in their home or elsewhere, they will be referred to as inventory in the same manner as in the case of a business in order to distinguish them from articles in other states, and will be described as objects for management.

Figure 18:
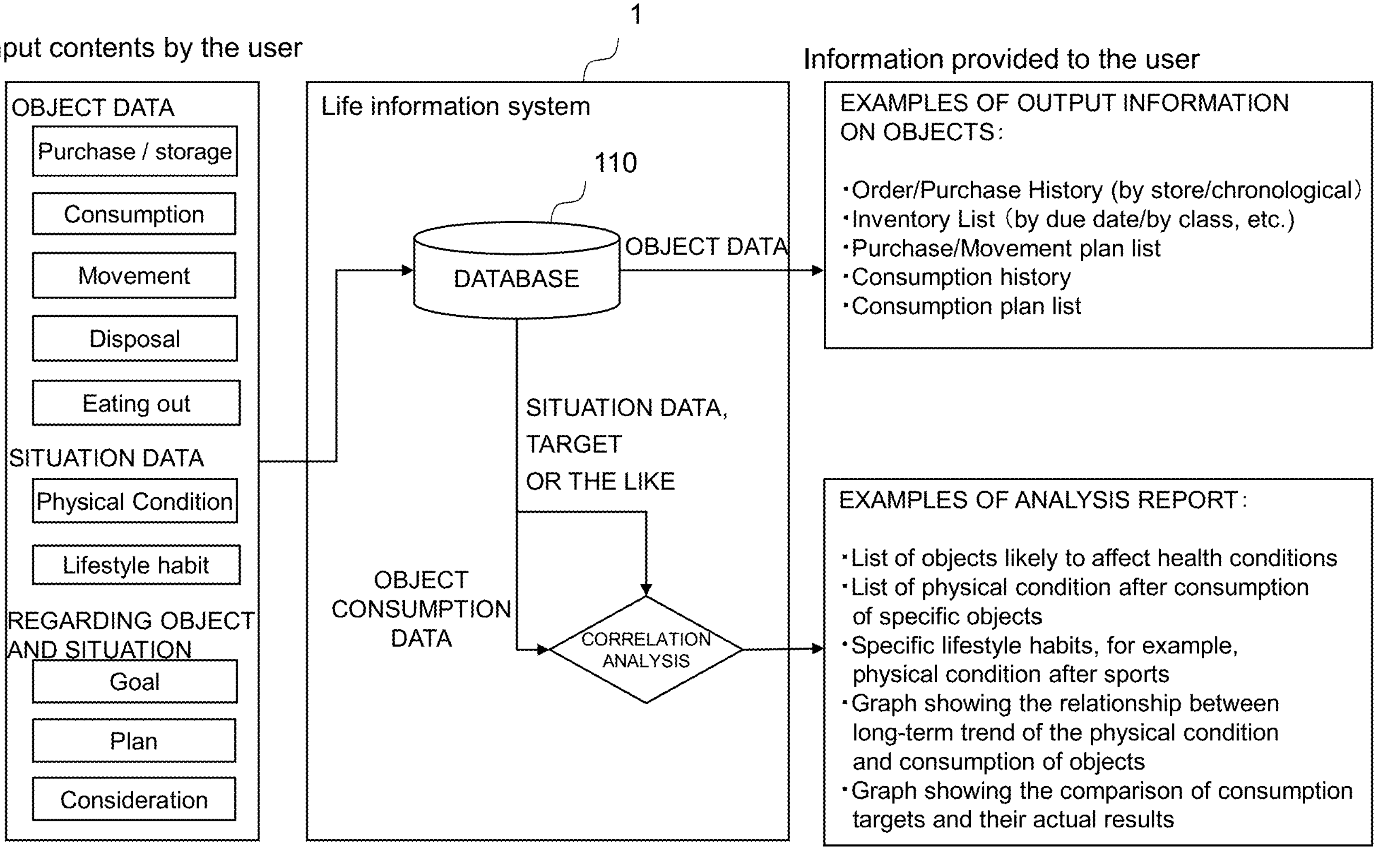
FIG. 18 is a diagram showing an outline of the flow from data input to output.

FIG. 18 shows an outline of the flow of information provided to the user from data input to the life information system 1 by the user. The life information system 1 can provide useful information to the users by analyzing the correlation of data not only on articles in their home and eating out situations (hereinafter referred to as "object data"), but also data on physical condition and lifestyle habits (hereinafter referred to as "situation data") in association with the object data. By recording the information input by the user in the database 110 as data, the life information system 1 can give meaning to the data in relation to the other data even if it is not useful on its own, which helps the user to utilize the information effectively. Note that the processing related to the database 110 described in the present embodiment is an example, and other processing methods using the database 110 that bring about an equivalent effect may be used, or some or all of the processing may be executed by a program that provides an effect equivalent to using the database 110.

The life information system 1 receives sentences entered into the information terminal 300 by voice or other means concerning detailed "object data" from purchase to consumption of articles (including the state of the user's food intake at a restaurant and elsewhere) and "situation data" such as the state of his/her physical condition, inspects their data contents, updates the database 110, references the information stored in the knowledge base 111, and analyzes the correlation between the user's consumption of articles and his/her physical condition. Based on the analysis results, this system proposes reference information to the user to improve his/her physical condition, sets a target consumption pace of articles according to the user's request, presents the user with advice based on the results compared with the actual consumption of articles, and also extracts and provides various useful information for life from the database 110 according to the user's request.

The user inputs information on articles (object data) and information related to his/her life (situation data) including appearance of any worrisome physical condition into the information terminal 300 as an event as it occurs. These contents are recorded in the database 110 together with information on the date and time of occurrence of the event. Although the life information system 1 can record events such as changes in the purchase and consumption of all articles in the home, as well as other changes in lifestyle habits and physical condition, it is also possible to record only events that the user wishes to pay attention to for the time being. As shown in FIG. 18, the life information system 1 covers not only the user's events but also considerations, goals, and plans.

In the life information system 1, it is possible to collectively update a plurality of data according to the user's intention by using an input method that can be intuitively and speedily performed from the information terminal 300 by a simple operation for the user, such as voice input and other means. This enable inventory management of articles using a database in general households, which was difficult in the past, and allows users to live efficiently without relying on memory, reducing psychological burden, increasing comfort in daily life, and effectively utilizing articles. In addition, by using the life information system 1, the user can create meal menus, dress outfits, and shopping plans efficiently without any waste. Furthermore, the user can easily check the cost-performance of articles and reduce wasteful expenditure. By managing the target consumption deadline and storage locations of articles, the user can significantly reduce food loss and other resource wastage, consume food and other items while they are still fresh, and reduce storage space.

Tables 1 to 4 below show examples of types of master tables, tables, queries as extraction processing results, and reports in the database 110. When using the information terminal 300 that allows the user to operate the screen, these can be displayed in tabular form on the screen, and the user can check and edit them on the screen. Of the three letters at the end of field names, the two letters on the left indicate the contents such as a value and number, while the lowercase letter on the right indicates their properties. The properties of the lowercase letters on the right are shown in Table 5. Except for class C1o in class table M-1, product name C2o and class C1s in product name table M-2, and initial setting of their corresponding samples, as well as selectable action content C4s and intention R6o in intention table M-11, initial setting of their corresponding samples, and inclusion conversion table M-10, the user can enter data that ends in m (master), o (original), or t (temporary used for original export). As an example, a level E1v of food material and level report R-2 refers to level E1o in level table T-4. Data names ending in "s" are selected by referring to data names ending in "m" (master) and "o" (original), while in the case of input by sentence, selection is made only if the target character string matches the reference m (master) and o (original). Although Tables 1 to 5 exemplify the contents related to the description of the present embodiment, the types and fields of tables or the like are not limited thereto.

TABLE 1

MASTER TABLES

| Number | Name | Fields |
|---|---|---|
| M-1 | class | classC1o |
| M-2 | product name | classC1s product nameC2o |
| M-3 | area | areaR5o |
| M-4 | store | areaR5s storeR2o taxF80 considerationD8o remarksD6o |
| M-5 | location summary | location summaryL2o currentN1o |
| M-6 | location | location summaryL2s locationL3o |
| M-7 | spot | spotL4o |
| M-8 | consumer | consumerL1o |
| M-9 | physical condition | featureR4o |
| M-10 | inclusion conversion | product nameC3o quantityQ4o inclusionE6o inclusion amountQ5o |
| M-11 | intention | action contentC4s intentionR6o |

TABLE 2

TABLES

| Number | Name | Fields |
|---|---|---|
| T-1 | menu | menuE5o considerationD9o remarksD7o |
| T-2 | food material | ID numberA1i storeR1o brandE2o product nameC2s aliasE30 acquisition dateT4o target consumption deadlineT5o locationL3s spotL4s currentN2t current memoM1t spareF1o finishedF2o purchaseF3o considerationD3o remarksD1o urgentF4o priceP1o Day1F5o Day2F6o Day3F7o |
| T-3 | consumption date and time | date and timeT1t consumerL1s menuE5s |
| T-4 | level | ID numberA9i date and timeT3o featureR4s levelE1o considerationD4o remarksD2o |
| T-5 | eating out | ID numberA8i date and timeT2o areaR5s storeR3o taxF9o menuE4o considerationD5o priceP2o contentD6o |
| T-6 | food material input | nicknameI1t quantityQ3t |
| T-7 | purchase time | storeR2s acquisition dateT4t spotL4s |
| T-8 | purchase content | brandE2t nicknameI3t target consumption deadlineT5t remarksD1t priceP1t |
| T-9 | stockpile | nicknameI5o shortest allowable consumption intervalT6o |

TABLE 3

EXTRACTION PROCESSING RESULTS (QUERIES)

| Number | Name | Fields |
|---|---|---|
| Q-1 | nickname | ID numberA1c storeR1v brandE2v classC1v product nameC2v aliasE3v nicknameA3i |
| Q-2 | food material record writing | ID numberA1c date and timeT1t storeR2v brandE2v product nameC2v nicknameI1t menuE5v location summaryL2h locationL3v spotL4v currentN1h current memoM1r spareF1n finishedF2n considerationD3r remarksD1r priceP1v |
| Q-3 | food material current confirmation | ID numberA1c date and timeT1t storeR2v brandE2v product nameC2v menuE5v location summaryL2h locationL3v spotL4v currentN2y current memoM1r finishedF2r considerationD3r remarksD1r priceP1v |
| Q-4 | food material plan | brandE2v product nameC2v target consumption deadlineT5v currentN2r urgentF4p Day1F5p Day2F6p Day3F7p |
| Q-5 | purchase history | storeR2e brandE2v product nameC2v nicknameA3c acquisition dateT4e target consumption deadlineT5v considerationD3r remarksD1r priceP1v |
| Q-6 | shopping | areaR5e storeR1e brandE2v classC1e product nameC2v purchaseF3y remarksD2r |
| Q-7 | inventory list | ID numberA1c storeR1e brandE2v classC1e product nameC2v acquisition dateT4v target consumption deadlineT5r location summaryL2h locationL3e spotL4e currentN1h/N2r spareF1n |

TABLE 3-continued

EXTRACTION PROCESSING RESULTS (QUERIES)

| Number | Name | Fields |
|---|---|---|
| | | finishedF2n purchaseF3r considerationD3r remarksD2r urgentF4y Day1F5r Day2F6r Day3F7r |
| Q-8 | stockpile detail | ID numberA1c storeR1e brandE2v classC1e product nameC2v nicknameI5s target consumption deadlineT5v shortest allowable consumption intervalT6r recommended consumption deadlineT7i location summaryL2h locationL3v spotL4v currentN2r spareF1r finishedF2r purchaseF3r considerationD3i remarksD1v urgentF4r Day1F5r Day2F6r Day3F7r |
| Q-9 | stockpile quantity | purchasable quantityQ2i total quantityQ1i brandE2v classC1v product nameC2v nicknameI5s considerationD3i |

TABLE 4

REPORTS

| Number | Name | Fields |
|---|---|---|
| R-1 | food material record | ID numberA1c date and timeT1o possibility % A4c scoreA5i storeR2s/R3c brandE2c product nameC2c aliasE3v nicknameA3c quantityQ3o target consumption deadlineT5c menuE5c locationL3c spotL4v current memoM1o/M2o considerationD3c remarksD1v/D2v priceP1c |
| R-2 | food material and level | ID numberA1c/A8c/A9c date and timeT1c/T2c/T3c featureR4c levelE1v brandE2c product nameC2w menuE4c current memoM1v/M2v considerationD3r/D4r/D5r remarksD1r/D2r contentD6c |
| R-3 | reaction confirmation | ID numberA1c/A8c/A9c date and timeT1c/T2c/T3c featureR4c levelE1v product nameC2w nicknameI4o menuE4v current memoM1v/M2v considerationD3r/D4r/D5r remarksD1v/D2v contentD6v |
| R-4 | conversion value | date and timeT3c featureR4c levelE1v conversion valueA2i |
| R-5 | score | ID numberA7i possibility % A4i scoreA6i storeR1v brandE2v product nameC2s considerationD3v |

TABLE 5

LOWERCASE LETTER AT THE END OF THE FIELD NAMES

| Mark | Description |
|---|---|
| m | Master |
| o | Original |
| t | Used temporarily to write "o", and to be deleted or overwritten after use |
| s | Selected from "m" or "o" |
| c | Written from "m", "o" or "i", and not updated thereafter |
| v | The latest information at the point of time is shown from "m" or "o" |
| w | The information on "c" is shown |
| e | Can be shown by narrowing down "m" or "o" |
| h | Hidden extract condition from "m" or "o" |
| r | Editable by referring to "m" or "o" |
| p | One of the editable extract conditions to refer to "o" |
| y | Flag on (yes), and one of the editable extract conditions |
| n | Flag off (no), and one of the editable extract conditions |
| i | Calculated value |

The large category of articles is a "class", and the class C1o of articles can be set in advance for each class, for example, "dairy products" and "fruits" in the class table M-1. The middle category of articles is a "product name", and for example, general product names such as "cheese" and "milk" among the class of "dairy products" are registered. When articles are initially registered, the product name C2o is made an essential field, and the product name C2o can be assigned the class C1s in the product name table M-2, which is a master table of the product name. When registering a new product name C2o, the class C1s is selected. As for representative product names, samples of the class C1s and the product name C2o and their corresponding templates are prepared in the product name table M-2, and the user can edit them as appropriate. For example, in the template, the product name C2o "apple" is assigned in advance to the class C1s, which is "fruit".

The sub-category of articles is "brand". The brand E2o field, which falls in the food material table T-2, is a field for freely entering information necessary for the user to identify the article in the household, such as the place of origin, manufacturer name, and other information for distinguishing the article. In the case of inputting the contents of "organic cabbage from Nagano prefecture" purchased at store A, the cabbage corresponds to the product name C2s, which is cabbage of the vegetable class C1s, and the contents such as "organic from Nagano prefecture" and " . . . brand" are registered as the brand E2o in the food material table T-2. As shown in the flow diagram of FIG. 4B, the presence or absence and content of the brand E2o entry is used to determine the identity of the article item. Input of the brand E2o to the food material table T-2 is not essential, and if it is not input, the identity can also be determined by the combination of a store R1o and a product name C2o. As shown in another example of FIG. 5, the store name and date of purchase can be collectively input together with information on articles purchased at the same time.

The data of each article is recorded in the food material table T-2 of the database 110 by the updating unit 103, together with information such as the spot L4s, the product name C2s, the brand E2o, the store R1o, the target consumption deadline T5o, and the like. Since the product name C2o is assigned the class C1s in the product name table M-2, the article can be made to correspond to a class C1e in the inventory list query Q-7. In response to a request from the information terminal 300 used by the user, the notification unit 105 transmits information for displaying an inventory list of articles by the spot L4e, the class C1e, or the like of the inventory list query Q-7 to the information terminal 300 used by the user. FIG. 6A is a display example of the inventory list grouped according to the class.

The food material table T-2 is a user's article list in the case of food as an example, and articles other than food can be handled in the same way as food. Since the food material table T-2 contains information on the store R1o, which means the store that sells the articles, as well as the product name C2s and the brand E2o, it is possible to specify the article items according to the flow of FIGS. 4A and 4B with that information. FIG. 7 shows an example of calling an inventory check screen using a sentence and an example of displaying the inventory list query Q-7 based on the food material table T-2 for each article. FIGS. 6A and 6B show lists of such information, and in the case of a screen-operable information terminal 300, the user can also edit the inventory contents from the screen such as shown in FIGS. 6A and 6B, and FIG. 7.

Figure 4A:
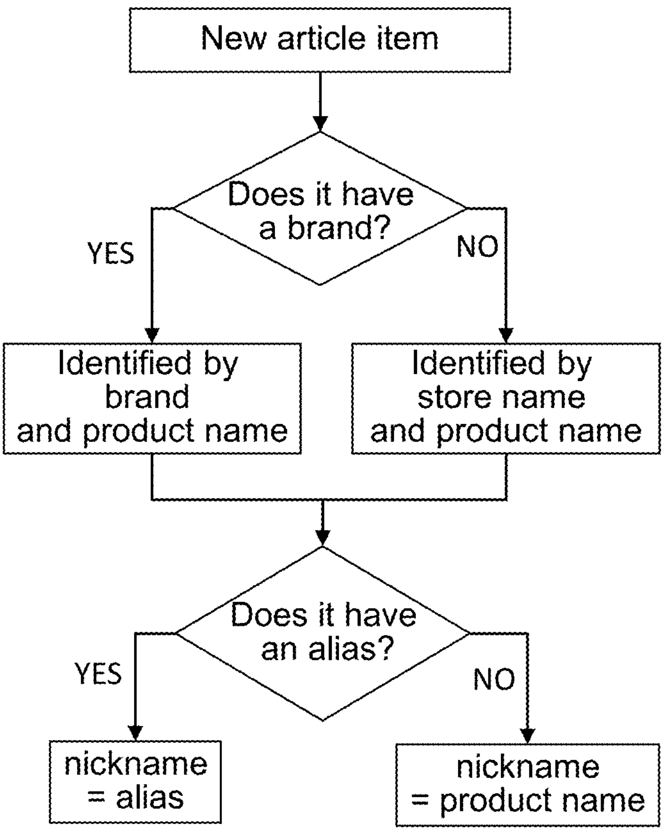
FIG. 4A is a diagram illustrating a flow of a method of specifying an article item and determining a nickname.

The present disclosure specifies that an article is either a raw material itself, or an article made of the same raw material which is treated as an article of the same item, and what is considered a raw material is not only a main substance but also a trace substance as far as possible. Therefore, in the present embodiment, an article with the same product name C2s and the same brand E2o, or if the brand E2o is not entered, an article with the same product name C2s and the same store R1o is regarded as an article of the same item. FIG. 4A contains a flow of a method of identifying article items depending on the presence or absence of a brand. For example, an article is considered to be the raw material itself such as "cabbage" or "carrot" in cooking food at the consumer's home, or to be made from the same raw material if it has both the same product name and the same brand in the case of processed food or the like, and such articles are treated as the same article item. Generally, an article means the same object as an article item, but a consumer may handle a plurality of articles having different purchase dates and target consumption deadlines even for the same article item, and each article in that case can be handled as separate records in the food material table T-2, and different contents can be input to the remarks D1o and the like in addition to the dates. In addition, when adding a new article, a copy of the record of the existing article item in the food material table T-2 can be used to update it.

Concerning articles, the life information system 1 records detailed information in the database when a user purchases, receives, stores, moves, uses, transfers, or disposes of articles. By doing so, the data recorded at the time of acquisition can be carried over during subsequent events of the articles, providing useful information for management and analysis. Therefore, the types of user's intentions described below include at least acquisition records and consumption records of articles. Since article items are linked to the information such as product name, class, brand, store of purchase, expiration date, or the like, by processing the information on acquisition and stored in the database, when recording the consumption of articles, it is possible to specify which article items of the inventory are consumed, and the consumption of articles can be recorded in detail so that the raw materials can be identified. As for processed foods and other items, if there are any raw materials that the user is interested in, the user records them in the remarks D1o in the food material table T-2. It should be noted that the processing relating to the acquisition and consumption of article items and the like in this embodiment can also be applied in another embodiment as follows: the article item is replaced by a virtual item other than the article, such as a schedule of housework, and the acquisition and consumption are replaced by addition and application of items and the like.

The acquisition unit 101 receives sentences related to articles that are input from the information terminal 300 used by the user according to the rules predetermined for each user at each timing, such as when purchasing food from a store or when consuming food. By limiting the intentions and contents of sentences input by the user in natural language with the prior consent of the user, the life information system 1 can accurately grasp the intention of the sentence and update the database. It should be noted that the description of the rules and prior arrangements described below means that the processing by the life information system 1 is limited to the user's prior agreement.

Figure 3:
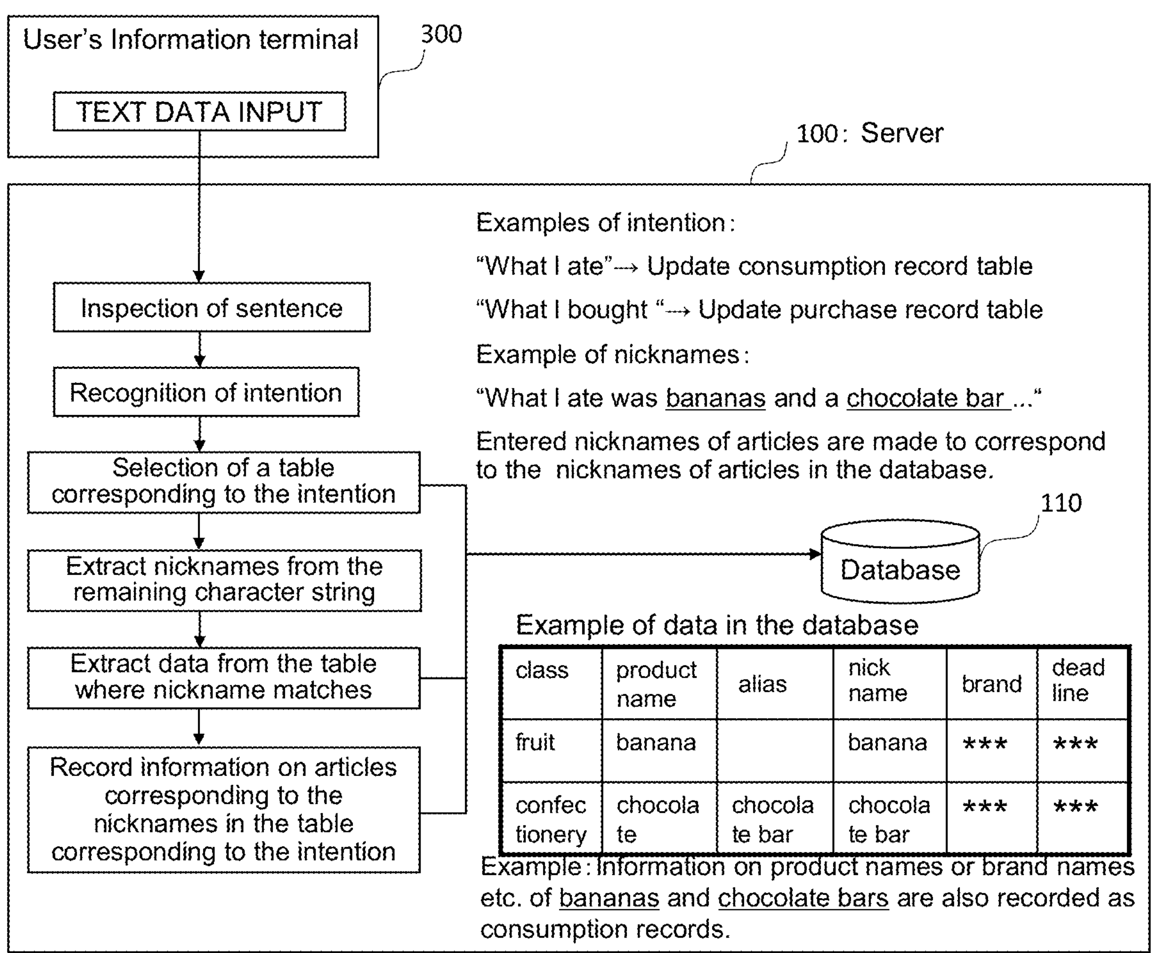
FIG. 3 is a diagram showing a flow from recognition of an intention in sentences until data is updated using a nickname.

FIG. 3 shows a flow from intention recognition to updating data using a nickname when the user inputs data by sentence into the information terminal 300. Prior to inputting life event data, a rule is established whereby the user specifies in advance a character string (hereinafter referred to as a "character string representing an intention") for indicating an intention and instructing an operation to the database. As a method, as shown in the example of FIG. 3, a rule is established that sentences containing the keywords "what I ate" should be treated as having an intention of consumption input, and when the keywords "what I bought" are included in the sentence, they should be treated as having an intention to input purchase details. Keywords can be set for each user. Note that a rule may be provided that, for example, when consumption input is frequent and the sentence does not contain a keyword representing the intention, it is regarded as having the intention of consumption input.

Within the database 110, there are several types of tables with different structures, as shown in Tables 1 and 2. The data in each table is distinguished for each user, and user-specific data is stored. By registering a character string representing an intention corresponding to the action content C4s for the database 110 in the intention R6o field in the intention table M-11, and by including the character string representing the intention in the sentence entered by the user, the type of table that corresponds to the intention of the user is selected, and it is determined what corresponding action should be taken for it. In the intention table M-11, samples of selectable action contents C4s, intentions R6o and their corresponding relationships are initially set, but the user can also register unique character strings in the intention R6o field.

The inspection unit 102 identifies a user's intention by recognizing a predetermined character string for instructing an operation to the database 110 in the sentence acquired by the acquisition unit 101. In this case, not only a single character string representing an intention as in the example of FIG. 3, but also a main word that is a main character string and, a sub-word that is a secondary character string, can be combined to instruct the database 110 to operate. In the example of D in FIG. 9, the "shopping plan" is the main word, and the "check" is the sub-word. When the inspection unit 102 recognizes the intention in the sentence, it recognizes the specific operation for the database 110, such as what kind of operation is to be performed for which table, and the operation can be processed by the updating unit 103, depending on the other contents in the sentence.

FIG. 8 shows an example where the intentions in the sentence are recognized and recorded in the corresponding table. If a character string representing an intention, for example, a keyword "meal outside" is agreed upon in advance for recording eating out, the data of eating out is recorded in the eating out table T-5. In the other example of FIG. 8, the level table T-4 is updated for the case of the sentence including "stomach condition". Updating of the food material input table T-6 and the consumption date and time table T-3 is an example of the case where there is no input of a character string representing the intention. This is the case where a rule for updating the food material input table T-6 and the consumption date and time table T-3 is established for such case.

The inspection unit 102 extracts the pre-registered nicknames of articles from character strings other than those representing the intention in the sentence. The updating unit 103 collectively updates the data of existing article items corresponding to the respective nicknames in a case where the character strings of the nicknames of one or a plurality of articles extracted by the inspection unit 102 match the character strings of one or a plurality of nicknames registered in the table selected in accordance with the intention of the user in the database 110. Note that, regarding recognition of the intention of the user, although situation data such as physical condition input and processing such as target setting can be handled in the same manner as the processing of object data, the cases of object data such as foods are described below as examples.

A nickname is a keyword for providing a one-to-one correspondence with an article item for each user, and by assigning a nickname as a keyword for specifying an individual article item to the article item in advance, it is possible to accurately extract data of the article items from the database 110 only by inputting nicknames, and the general consumer can easily utilize the result of a complicated process.

The nickname query Q-1 is based on the food material table T-2, and according to the nickname query Q-1, the product name C2v is used for the nickname A3i unless an alias E3o is specified in the food material table T-2. If the alias E3o has been specified by the user in advance, the alias is used as the nickname A3i. For example, even if the product name C2v is "apple", if the alias E3o "green apple" is specified, the alias is given priority and the nickname A3i becomes "green apple". If the alias E3o is not entered, the nickname A3i will be "apple". The table at the bottom right of FIG. 3 is another example of such a method. FIG. 4A shows how to identify an article item and how to determine a nickname based on the presence or absence of an alias. When inputting nicknames I3t in the purchase content table T-8 regarding the purchase of articles or nicknames I1t to the food material input table T-6 regarding the consumption of articles, the database 110 can be updated collectively by making the input nicknames of the articles correspond to the nicknames A3i of inventory articles. If the alias E3v is not set for different article items with the same product name C2v, and neither of them has the finished flag F2o or the spare flag F1o, the product name C2v is used for extraction as a nickname A3i, but plural different article items may be extracted for one nickname A3i. In such a case, by prompting the user to set an alias E3o to either one of the items, the article items can be accurately distinguished. Or, if the consumption input is performed without the alias E3o, it can be handled in the order of the earliest date of acquisition according to the setting situation, as described later.

When a plurality of nicknames are inputted for a single intention, nicknames in the sentence can be more accurately recognized by setting a rule in advance for each user, to use a character or a symbol such as "and", "&", "," or the like as separators for a word or symbol between a nickname and another nickname of articles in the sentence inputted by the user. For example, in the expression "What I ate at 13:00 on Wednesday was potato and onion and olive oil", the rules are set to separate words with conjunctions such as "and" or "and then", symbols such as "&" or ",", or spaces. For example, a character string input as "cabbage and garlic and carrot" or "cabbage & garlic & carrot" is divided and extracted into the three words, "cabbage", "garlic", and "carrot" by the inspection unit 102. When the extracted character string does not match the existing nickname A3i of the nickname query Q-1, it may be processed by matching the product name C2s of the food material table T-2. Also, when the input character string partially matches the product name C2s or brand E2o of the article previously recorded in the food material table T-2, the user may be prompted to select them as candidate articles, or patterns of incorrect input, such as product names, may be stored in the knowledge base 111 to prompt the user to select them as candidates for conversion. Alternatively, as a new article item, a character string may be temporarily recorded as the product name in an unclassified state, or the user may be asked for the registration content at the time or later.

As described above, by entering a plurality of nicknames for a single intention, a plurality of records in the table can be manipulated collectively. Furthermore, the inspection unit 102 recognizes character strings representing the fields of information related to article input after the nickname of the article in the sentence, thereby extracting the following contents of the fields, and the updating unit 103 can record the information on the article together with the nickname of the article. For example, if a character string such as "and the remarks are . . . and the consideration is . . . and current memo is . . . and then", is entered following each nickname, the inspection unit 102 can recognize the contents of a plurality of fields for each nickname by clarifying the field name with a character string such as "remarks are" or "consideration is". Note that the "and then" at the end of the above sentence is an example that separates a nickname from another nickname, and is treated as a delimiter of information relating to a single nickname. In addition, it should be noted that a rule may be established that if the field name is not included as in this example, and the character string "which is" is simply used after the nickname, it is recognized as the remarks D1o. Furthermore, by including a specific character string in the remarks D1o or the like, it can be used as a user's own flag when extracting data. In addition, immediately after the nickname, for example, by using a character string that means cancellation or replacement, such as "cancel" or "change to", after setting a rule in advance, it is possible to cancel a nickname already entered or replace it by another nickname. For example, assume that a rule has been agreed upon in advance that when the character string "change to" is entered, the character string immediately before "change to", is replaced by the immediately following nickname. Namely, the character string "cabbage change to lettuce" will be broken down into "lettuce", "change to", and "cabbage", but only the character string "lettuce", not "cabbage", will be recorded in the database 110. As another example, according to prior arrangements, if a phrase that should normally be one word is entered consecutively, such as "at 13:00 level 2.5 level 2.8" or "at 13:00 14:00 . . . ", only the latter word can be adopted.

When entering the purchase details, the user first selects the purchase store R2s that has been registered in advance in the purchase time table T-7, and then enters the purchase date and time T4t. A spot L4s can also be selected for each storage location. Further, the nickname I3t, or the like is entered in the purchase content table T-8, and the purchase items are added to the food material table T-2 based on these input details. Information such as a product name C2s, a brand E2o, a target consumption deadline T5o, and an amount P1o is added to the food material table T-2 using the purchase time table T-7 and the purchase content table T-8, or by directly adding a record to the food material table T-2. The handling of nicknames differs slightly between inputs related to article consumption and the like, described later, and inputs at the time of acquisition. As input contents when obtaining an article, in addition to the store name R2s, the nickname or the product name is entered as the article name I3t, and in some cases, the brand name E2t is also entered. In the case of transfer instead of purchase, the transferor's name may be entered in the store name R2s.

Figure 4B:
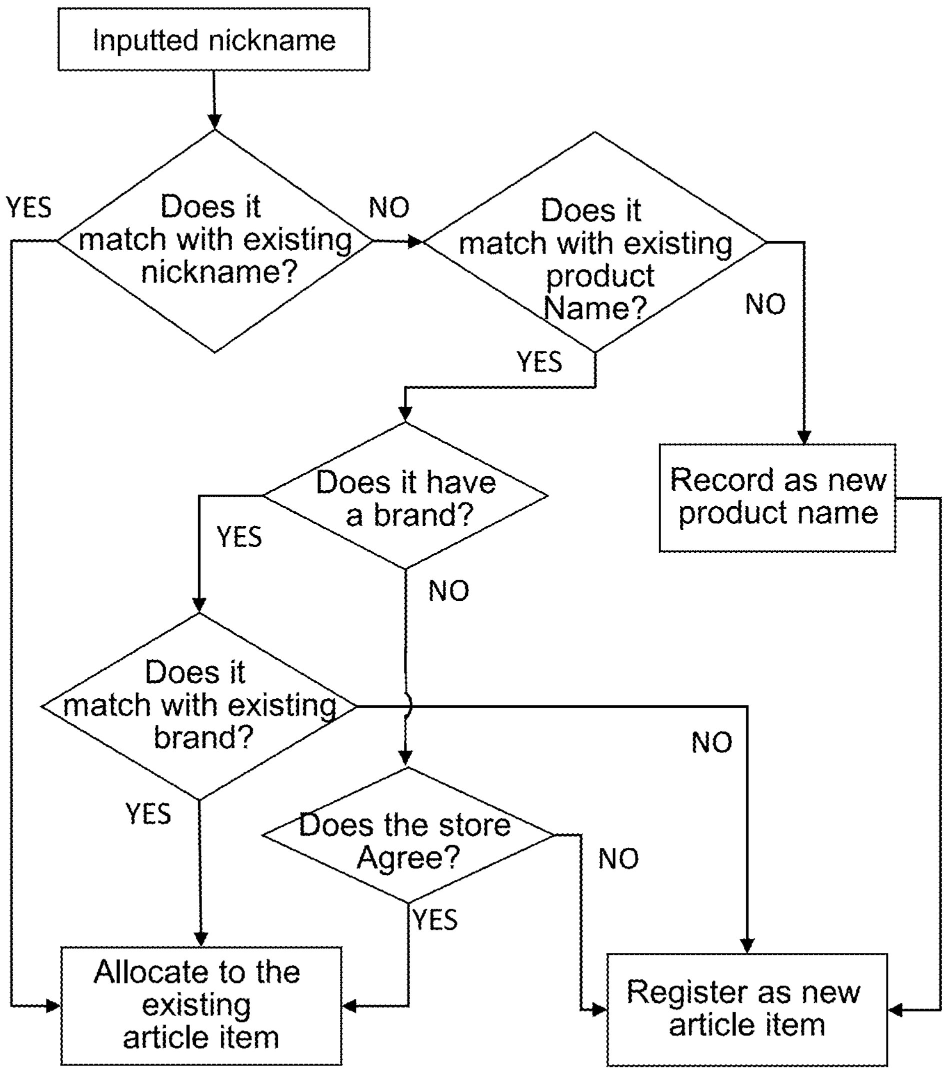
FIG. 4B is a diagram illustrating a flow of an article item allocation method.

FIG. 4B shows the flow of the method of allocating article items, such as at the time of acquisition. The flow of FIG. 4B applies the flow of the method of specifying article items in FIG. 4A to processing such as at the time of acquisition. When the same article item as an already existing one is purchased, if the nickname I3t entered in the purchase content table T-8 matches the nickname A3i of the nickname query Q-1, it is matched with the article item of the food material table T-2, and some of the existing data is transcribed as that of the new acquisition date T4o. At the time of acquisition, the input nickname I3t that does not match the existing nickname A3i is basically treated as a new article item. However, as shown in FIG. 4B, if the name of the entered article does not match the nickname A3i, it is also checked whether it matches the existing product name C2s recorded in the food material table T-2. This assumes a case where the user has entered the product name when recalling data for an existing article item, even though it has an alias. Further, the identity is determined by the determination of whether the input brand E2t is identical to the existing brand E2o, or whether the input store name R2s is identical to the existing article store name R1o. Once the acquired articles are recorded, it is possible to check the purchase history by referring to the data in the food material table T-2 by store R2e and by acquisition date T4e, using the purchase history query Q-5.

As a method of entering date and time when entering an event prior to the time of input, there is a method of selecting the date and time from options, but this requires some work, and entering date and time by a sentence is inaccurate unless the intention is limited. Therefore, if there is a character string representing the date and time before the keyword representing the user's intention in the input sentence, the inspection unit 102 converts the character string to the past date and time data as the timing immediately before the input, and instead of the sentence input time, the updating unit 103 records the date and time T1t of the consumption date and time table T-3, the date and time T3o of the level table T-4, or the date and time T2o of the eating out table T-5, or the like as the date and time of occurrence of the actual life event of the user according to the user's intention. Then, the notification unit 105 sends the data of the user's life event extracted in response to the user's request each time to the information terminal 300 used by the user for display. FIG. 8 shows an example of recognizing the date and time from the input contents. As other examples, for a description such as "at 19:00 yesterday" or "two hours ago", the past date and times are calculated from the input dates and times. Note that the user may be able to make a setting in advance to omit the input of the time, such as setting dinner to be 19:00. In that case, for example, if the sentence "yesterday's dinner was" is input on December 2nd, the event is recorded as an event at 19:00 on December 1st. If there is no character string related to the date and time in the sentence, the date and time of input to the information terminal 300 is treated as the event occurrence time and recorded in the corresponding table.

The user can register in advance the store R2o in the store table M-4 where the user frequently purchases articles. Then, by setting the flag F8o to determine whether a store's price includes tax or not, the user can calculate the price in a uniform way by simply entering the store name R2s into the purchase table T-7 at the time of purchase, even if the price sometimes includes tax, and sometimes does not. In addition, by registering the store R2o, it is possible to display a list of considerations D3r and amounts P1v corresponding to the articles in the purchase history query Q-5 for each store.

Figure 5:
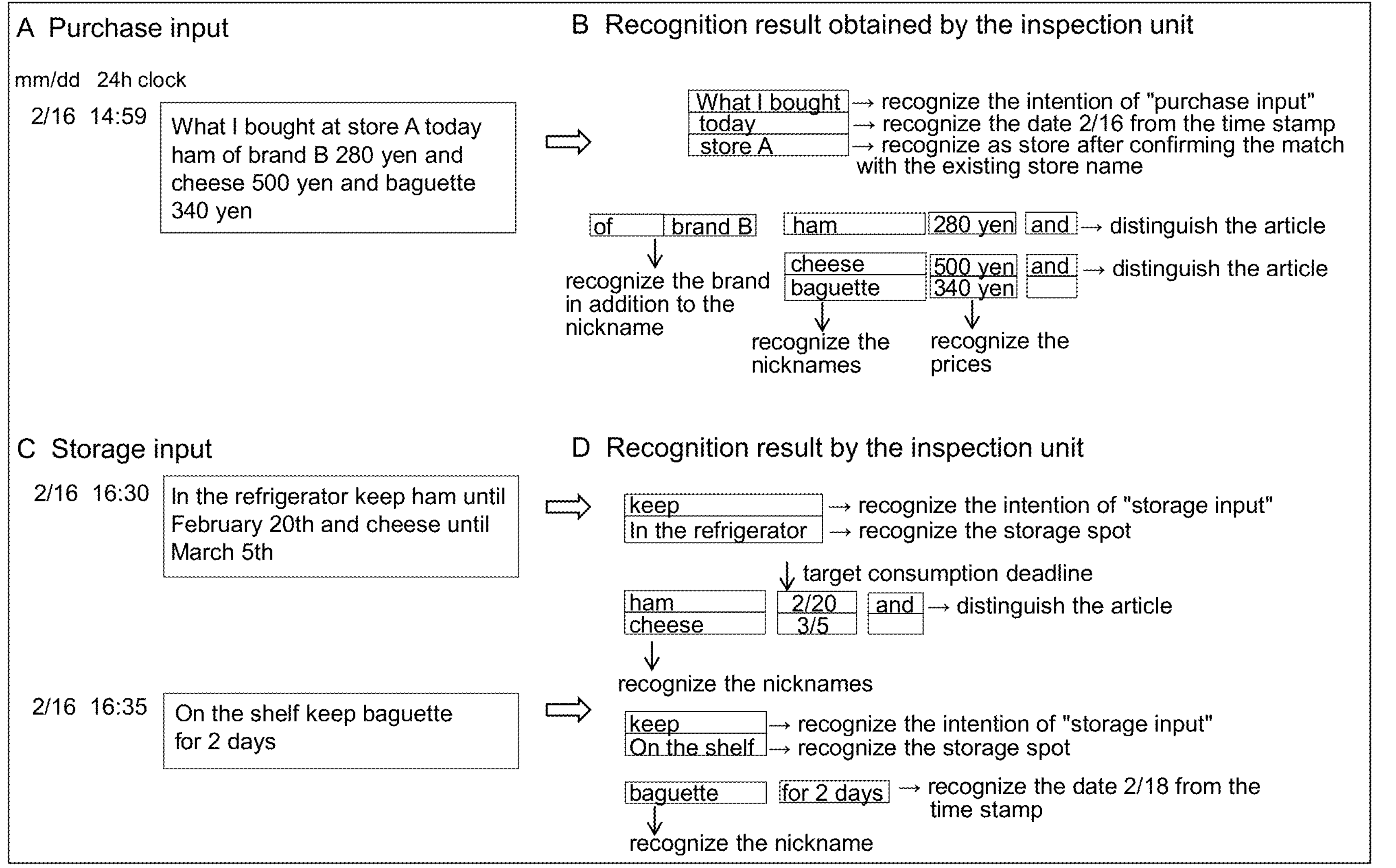
FIG. 5 is a diagram showing an example of a screen and processing related to purchase and storage inputs.

By registering the storage spot L4o such as "refrigerator" or "freezer" in the location table M-7 in advance, the user can manage the inventory of articles by storage spot. A of FIG. 5 shows an example of recording the purchase contents of the articles in the database 110 by sentences. When the acquisition date T4t, a character string intended to input the purchase contents such as "what I bought", the store name R2s, and the brand E2t, the nickname I3t, the price P1t, or the like of the articles are input, the contents of B of FIG. 5 are recognized by the inspection unit 102, and recorded in the purchase time table T-7 and the purchase content table T-8 by the updating unit 103. If the purchase and storage inputs are separated, the storage spot can also be put on hold as for an unstocked article. As shown in the example of C of FIG. 5, when the purchased article is stored, the storage spot L4s can also be entered together with the nickname I3t, and when the inspection unit 102 recognizes the intention R6o related to storage as in the example of D of FIG. 5, the storage spot L4s of the article can be recognized.

Although the input of the price P1t at the time of purchase is not essential, if the price P1t is recorded as in the example of in A and B of FIG. 5, it is also possible to calculate the cost of consumption for a certain period or for each menu. Although the consumption record may be performed more than once from the time an article is purchased until it is finished, the cost can be calculated in a simplified manner by assigning the purchase price P1o to the consumption events. For example, when an article is used five times, one-fifth of the price can be treated as a consumption record corresponding to the consumed article. The scheduled number of uses may be calculated from the user's past consumption pattern, or the scheduled number of uses may be calculated from the quantity of the article at the time of purchase by referring to the standard amount of use from the knowledge base 111 according to the product name of the article.

The purchase or the order result may be entered by reading the image of the receipt or the delivery note with the information terminal 300, or by capturing an order result mail text or the like. When recording from the order result stage, the user may also check the list of expected arrivals. With respect to an ordered product, the user can call data of articles again when the article is actually obtained, and update the data by entering the target consumption deadlines T5o, the storage locations L4s, or the remarks D1o in the food material table T-2 while checking the actual article.

One cause of food loss, which has become an issue in recent years, is the discarding of expired food at home. One of the causes of this is to buy large quantities of food and forget to consume it. Similar problems apply to non-food items. The expiration date or the consumption deadline printed on the article is not necessarily the date of consumption desired by the user. In addition, there are many articles that do not have an expiration date written on them, or need to be consumed as soon as possible after opening. Since consumption of deteriorated food adversely affects health, it is desirable to consume food in a fresh state. In order for the user to efficiently set the target consumption deadline, a method of quickly inputting while actually checking the articles is required.

Figure 15:
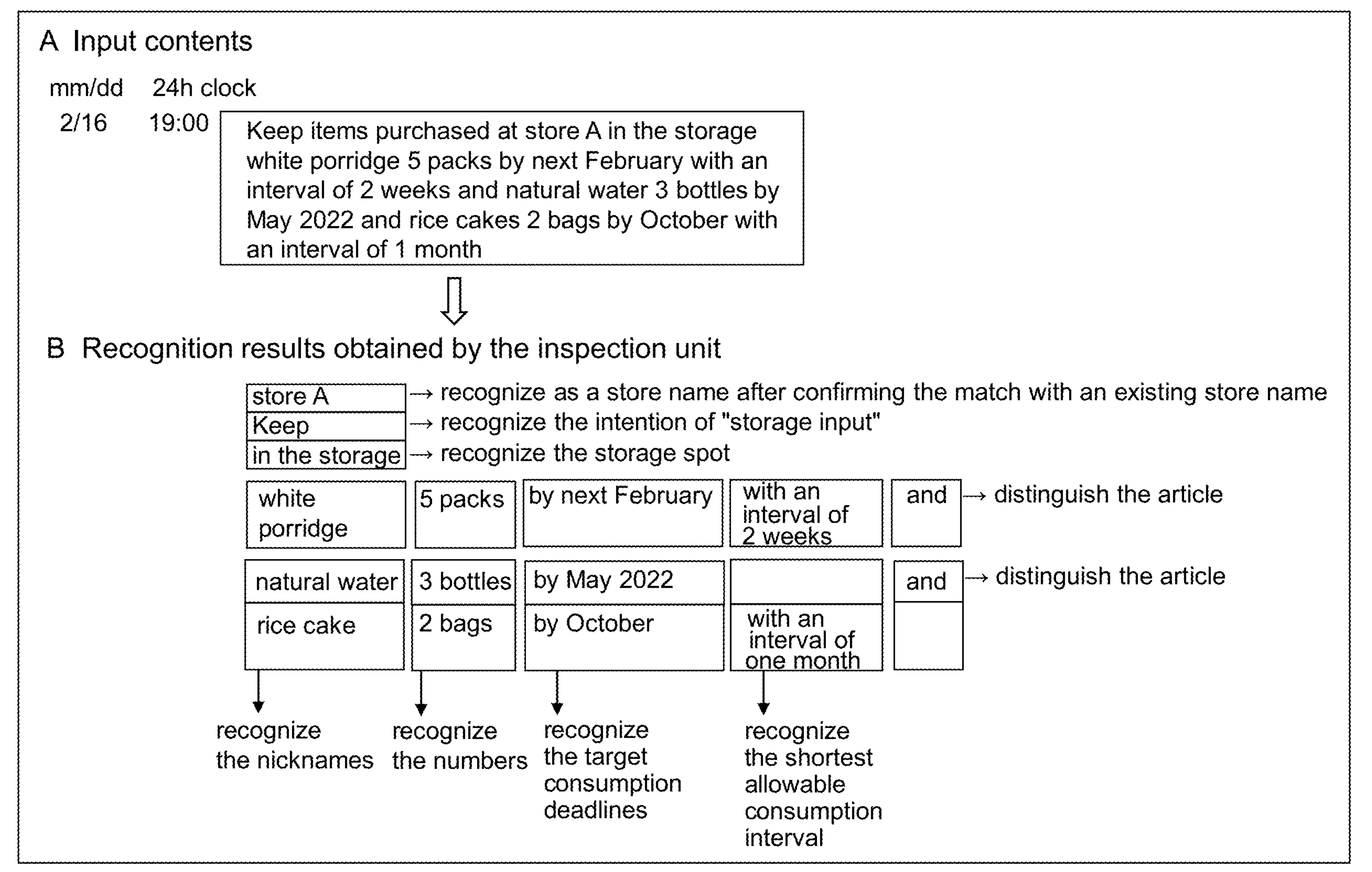
FIG. 15 is a diagram illustrating an example of a screen and processing related to rolling stocks.

The user can freely set the target consumption deadline regardless of the expiration date written on the food label or the like, or even if the expiration date is not written. The target consumption deadline may be entered by the user on the purchase entry or inventory check screen by selecting the date individually. However, if it is entered in a sentence, the character strings representing the dates after the keywords representing the nicknames of articles in the sentence separated by each purchase entry or inventory check intention are converted to date data, and recorded in the food material table T-2 as the target consumption deadline T5o. For example, it is possible to perform an input using a sentence such as "Enter the deadline of sesame oil until January 15 and lettuce in 3 days". In this case, the intention of updating the target consumption deadline T5o of the food material table T-2 is recognized by making the character string "Enter the deadline" correspond to the intention R6o of the intention table M-11, and the nicknames "sesame oil" and "lettuce" correspond to and are recognized as A3i. For example, if the entry time point is Apr. 10, 2020, the target consumption deadline for "sesame oil" and "lettuce" are recorded as Jan. 15, 2021 and Apr. 13, 2020, respectively, in the target consumption deadlines T5o of the corresponding articles. C of FIG. 5 and FIG. 15 are examples in which the target consumption deadline T5o are also input when entering storage of articles. For specific article items, an additional field of days available for storage may be provided, so that the target consumption deadline T5o can be calculated in advance from the acquisition date T4o.

With the life information system 1, the user can efficiently stockpile inventory as rolling stock without waste by adding a little information about the articles. When the user owns more than one of the same article items, the notification unit 105 calculates the recommended consumption deadline T7i for each article from the shortest allowable consumption interval T6o of the stockpile table T-9, which is an interval wherein the user can consume the article item, and the target consumption deadline T5o of the individual article of the article item, and in response to a request from the information terminal 300 used by the user, information for displaying the recommended consumption deadline T7i of the article is transmitted to the information terminal 300 used by the user. If the shortest allowable consumption interval T6o is not specified and there are a plurality of stocks of articles, when the target consumption deadline approaches, it may be necessary to consume them all together, which becomes a burden to the user. The shortest allowable consumption interval T6o, which is the shortest interval for comfortable consumption of the article, can be entered in advance by a user subjectively, or when there is no input, the notification unit 105 can determine it by referring to information of other consumers in the knowledge base. The notification unit 105 can also transmit a list of the target consumption deadlines T5o or the recommended consumption deadlines T7i for each article to the information terminal 300 used by the user in response to a request from the information terminal 300 used by the user, and can also transmit a notification to prompt the user to consume the article when the recommended consumption deadline T7i of each article approaches.

The user inputs stockpile target articles into the stockpile table T-9 with the nickname I5o, and the shortest allowable consumption interval T6o for the target articles as necessary. By matching the input nickname I5o with the nickname A3i of the nickname query Q-1, the data of the stockpile detail query Q-8 and the stockpile quantity query Q-9 are extracted, and related calculations become possible. The recommended consumption deadline T7i can be checked in the stockpile detail query Q-8. FIG. 15 shows an example of inputting a target consumption deadline T5o and a shortest allowable consumption interval T6o by a sentence when storing purchased articles.

Figure 16:
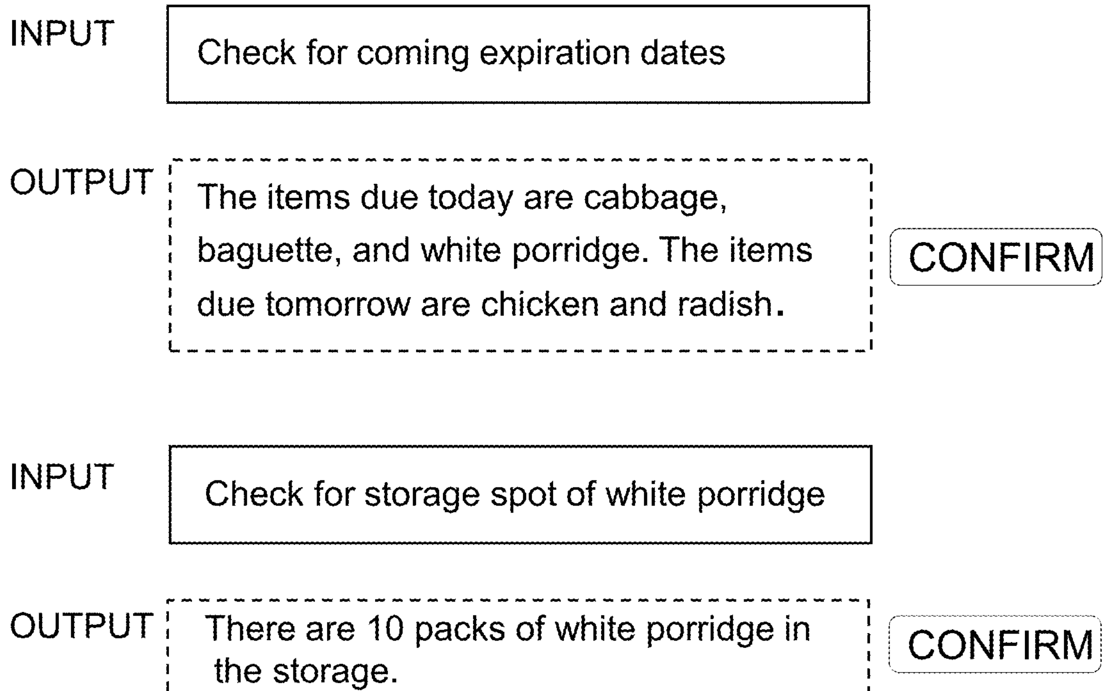
FIG. 16 is a display example of a screen for confirming inventory expiration date and storage spot.

FIG. 16 is a display example of a screen of the information terminal 300 when confirming the target consumption deadline T5o or the recommended consumption deadline T7i and the storage spot L4s by a sentence. Among the examples of deadlines in this figure, "white porridge" is assumed to be the stockpiled article for which the recommended consumption deadline T7i is calculated from the target consumption deadline T5o and the shortest allowable consumption interval T6o entered as the example in FIG. 15.

In addition, for articles registered as the articles to be stockpiled by the user in advance in the stockpile table T-9, the notification unit 105 calculates the storable period of the articles from the relationship between the past target consumption deadline T5o and the acquisition date T4o in the food material table T-2, and further calculates the maximum storable quantity of the articles to be kept for the user in the stockpile quantity query Q-9 from the shortest allowable consumption interval T6o. When the total quantity of article Q1i falls below the maximum storable quantity, a notification concerning the purchasable quantity Q2i of the articles can be sent to the information terminal 300 used by the user.

When the user has plural articles of the same item with different target consumption deadlines, if m is the shortest allowable consumption interval, $t_n$ is the target consumption deadline and $r_n$ is the recommended consumption deadline of the n-th item, $r_n$ is calculated as $t_{n+1}-m$ or $t_n$, whichever is smaller. Note that the target consumption deadline $t_{n+1}$ is the target consumption deadline of the next article among the same items that have a target consumption deadline after the n-th article.

Further, assuming that the storable period of the n-th article is $p_n$, the acquisition date is $d_n$, the standard storable period of the article item based on the average actual past storable periods of the same article item or the data in the knowledge base 111 is p, the inventory quantity of the same article item is q and the maximum storable quantity is a, the purchasable quantity b is calculated according to the following mathematical expression.

$$p_n=t_n-d_n$$

$$a=p/m$$

$$b=a-q$$

In order to manage the article information by spot, the tables M-5 to M-7 have fields for location summary L2o as a large section, location L3o as a middle section, and spot L4o as a small section. The user can manage the inventory for plural sites by registering the location L3o in the location table M-6 prior to the input of the purchase or consumption events. In addition, by selecting the location L3s of the articles at the time of recording the food material table T-2, the user can display the articles by the location L3e in the inventory list query Q-7. Further, by setting the current flag N1o in the location summary L2o of the location summary table M-5, only the data of the articles corresponding to the location L3o associated with the location summary L2s of the corresponding location table M-6 will be subject to the writing of the actual consumption record by the food record writing query Q-2 based on the nicknames, and the inventory listing query Q-7 can display only the corresponding data at location L3.

For example, "Shinjuku" such as the location of the user's residence and "from Shinjuku to Yokohama" which means the user's movement schedule are registered in the location L3o as the middle section, and they are summarized in the location table M-6 by selecting and associating with one of the options of the location summary L2s, for example "Tokyo". After that, by setting the current flag N1o to "Tokyo" in the location summary L2o in the location summary table M-5, the user can display the inventory list of the articles including not only "Shinjuku" but also "from Shinjuku to Yokohama" in the inventory list query Q-7.

When the user wants to record the lifestyle habit and physical condition of a person other than a user, for example, a child of the user, the user can easily perform consumption recording of food material and input of physical condition by entering the name of the target consumer before entering the contents of a series of events or for each individual event. Since the user can manage information of a plurality of consumers, for example, it is possible to manage an object or physical condition corresponding to a family member. The method is to set a consumer L1o in the consumer table M-8 prior to the consumption input. In addition, it is also possible to input more than one consumer name at once in the consumer L1o field. As illustrated in FIG. 8, when the name of the subject is selected as a consumer L1s in the consumption date and time table T-3, the subsequent inputs are treated as those for the subject until the consumer is individually input or the consumer L1s is changed. When managing information of a plurality of consumers, the subject can be easily switched by entering the name individually for each event as shown in an example of FIG. 8, and a report for each subject can be generated by extracting data for each target.

There are two methods for entering consumed article items, one by using a nickname, and the other by using a flag in the case of a screen-displayable information terminal 300. The screen-displayable information terminal 300 can be used for different methods as appropriate, such that frequently consumed articles are entered by nicknames, while other articles are entered using flags.

In the case of the method using the nickname, as shown in the example of the consumption record in FIG. 3, the recognized nicknames I1t of the food material input table T-6 correspond to the nicknames A3i of the nickname query Q-1, and among the articles recorded in the food material table T-2, the location L3s corresponds to the current flag N1o in the location summary table M-5 and the location table M-6. Also, for those that are not flagged with the spare flag F1o and the finished flag F2o, which will be described later, the data in the food material table T-2 is extracted and written out as the food material record report R-1. The food material record writing query Q-2 is a confirmation query before updating the food material record report R-1 when using nicknames. When using the flag, the user calls the list of article data as shown in the examples of FIGS. 6A and 6B from the screen of the inventory list query Q-7 of the information terminal 300, checks the current check box N2r, and applies the current flag N2t to a plurality of articles in the food material table T-2, and then the updating unit 103 collectively records the consumption in the date and time T1t specified in the consumption date and time table T-3 to the food material record report R-1. The current food material confirmation query Q-3 is a query for confirmation before the food material record report R-1 is updated when using flags. Note that the current flags N2t in the food material table T-2 are temporarily used for input, and they are collectively deleted after updating the database 110.

The food material table T-2 has an input column for a current memo M1t, and the user can enter a note regarding the consumption of the article when entering consumption. The current memo M1t is written out only in the food material record report R-1, which is the consumption history, together with information such as consumption date and time, and it does not remain as a record in the food material table T-2.

As shown in the screen example of the consumption event input using a nickname in FIG. 8, the user can collectively input to the consumption date and time table T-3 and the food material input table T-6 by continuous sentences. As an example, as in the first input box, if the sentence "At 8:00 in the morning carrot and lettuce and mayonnaise and bread and milk and butter" is input, 8:00 immediately before the input time is recorded in the date and time T1t of the consumption date and time table T-3. Nicknames I1t of carrot, lettuce, mayonnaise, bread, milk, and butter in the food material input table T-6 corresponding to nicknames A3i in the nickname query Q-1, respectively are linked to the corresponding data in the food material table T-2, and the data are recorded in chronological order in the food material record report R-1 as consumed. If the input nickname I1t does not have a one-to-one relationship with the existing nickname A3i but exceptionally has a one-to-many relationship, a system may be provided such that the older one with the ID number A1i is prioritized for correspondence.

It is assumed that the input of a sentence by an input box or by e-mail is usually for a single intention at a time, however, as in the example of the fourth input box in FIG. 8, when a plurality of intentions are consecutively input into one sentence, the inspection unit 102 searches for a plurality of character strings representing the intentions of the user in the sentence, and extracts character strings dependent on each intention from each character string before and after the plurality of character strings representing the retrieved intentions, thereby the sentence can be divided for each intention. If the user inputs, for example, "What I ate at 8:00 was milk and banana and apple and at 9:00 stomach condition level 2 and what I have in the refrigerator is milk until January 30th", the updating unit 103 recognizes the user's intention of "what I ate" (consumption of food material), "stomach condition" (physical condition record), and "what I have in the refrigerator" (confirmation of inventory), and selects the tables to be recorded. Since the character strings representing these intentions are agreed with the user in advance, the updating unit 103 can reliably select the recording destination table without missing the intention of the user.

The character strings dependent on each of the recognized intentions are usually after the character strings representing the intentions when a plurality of intentions are included in one sentence. However, the information on some fields is exceptionally before the character string representing the intention. In the above example, "stomach condition" is preceded by the time string "9:00", and "9:00" is immediately preceded by "at". By defining the rules for processing such cases in advance, the time string can be subordinated to the intention immediately following it. The inspection unit 102 processes the example of "8:00" in the same way, analyzes the input date and time by a time stamp and the character string related to the date and time in the sentence, and recognizes the occurrence dates and times of the events of the food material consumption and the change of physical condition as occurring at 8:00 and 9:00 on the input day, respectively. Then, the updating unit 103 records the dates and times of the events in the corresponding table. As for the contents of food consumption at 8:00, milk, banana, and apple, which are the nicknames A3i, are extracted from the sentence, and after being matched with the information on the articles registered in the food material table T-2, they are written out in the food material record report R-1. Note that a plurality of intentions in the sentence may be recognized by the above-described method, or the sentence delimitation may be performed by including specific keywords in a sentence based on the agreement of the user.

Consumed articles are not displayed in the inventory list query Q-7 when the user sets a finished flag F2o to the articles in the food material table T-2 at the time of completion of consumption or the like. When there is no stock after consumption, it is also possible to set the finished flag F2o on the screen for checking the food material record writing query Q-2 or the food material current confirmation query Q-3. If the article is frequently replaced or the same article is always kept in stock, it may be put in a state of being always in stock in the database by not setting the finished flag F2o on the article. Note that the life information system 1 assumes a general consumer as a main user, and can be used without strict number management of inventory. The finished flag F2o can also be entered with a sentence such as "no more potatoes". Or it may be arranged if a consumption input contains "all" in front of the nickname, such as "all the spinach, all the pork, and . . . ", the finished flag F2o is set at the same time the consumption input is made.

When there is more than one inventory of the same article item in the food material table T-2, the user can flag a specific item as the spare flag F1o, so that the non-spare inventory among the plurality of inventory articles is preferentially consumed. If there is no spare flag, it is also possible to treat it as being consumed such as in order of earlier target consumption deadline, and then in order of earlier purchase date.

Figure 9:
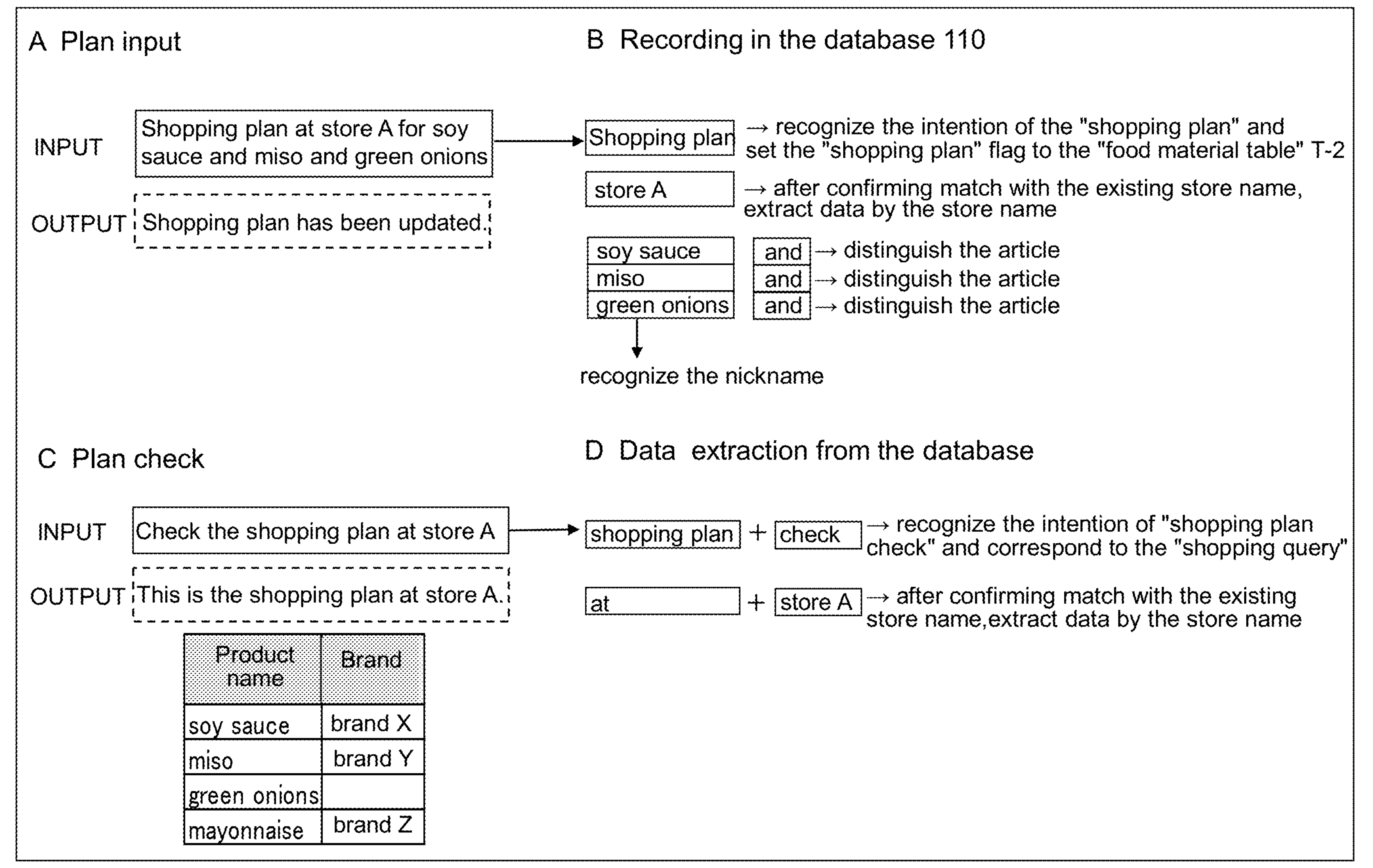
FIG. 9 is a diagram illustrating an example of a screen and processing related to a purchase plan.

For articles purchased in the past or for those articles the user wishes to newly purchase, the user can display the shopping query Q-6, which is the purchase plan list, by recording the items purchased in the past or the items to be newly purchased, together with the information on the store R1o or the brand E2o and the product name C2s, and by setting up purchase flags F3o which mean "to be purchased" in the food material table T-2. Also the user can display a store R1e, a sales area R5e, or the class C1e, respectively in the shopping query Q-6. By setting the location L3o to "to be purchased" for an article that the user wishes to purchase, the user can exclude it from the inventory list in the inventory list query Q-7. The "purchase plan" flag F3o can be set by including it in the sentence when the article is consumed or when checking inventory, or it can be checked from the inventory list screen as shown in FIGS. 6A and 6B. FIG. 9 is an example of update and confirmation of a purchase plan. A is an example of a screen of the information terminal 300 for updating purchase plan information, B indicates responses of the inspection unit 102 and the updating unit 103 corresponding to the input content of A, C is an example of a confirmation request from the user for an existing purchase plan, and D is an example of responses from the inspection unit 102 and the notification unit 105. In this example, the displayed content of the output portion of C is finally transmitted by the notification unit 105.

Further, the life information system 1 allows the user to obtain reference information on purchasing not only known articles to be purchased, but also unknown articles as recommended articles. The knowledge base 111 stores information on recommended articles based on experiences of other users or obtained from other sources. The analysis unit 104 extracts data of recommended articles which are not included in the article inventory according to the food material table T-2 or the inventory list query Q-7 in the individual user's database 110 by using the data of the recommended articles accumulated in the knowledge base 111, and the notification unit 105 can transmit them to the information terminal 300 used by the user as a reference for purchase. The determination of whether or not the user's inventory in the database 110 does not include the recommended articles of the knowledge base 111 is made by using the keywords provided for each recommended article. Further, the analysis unit 104 may refer to consumption records such as the food material record report R-1, or physical condition data described later, when extracting data on recommended articles from the knowledge base 111. Also, limits may be placed on the number and frequency of recommended articles to be notified so that the number of recommended articles and the frequency of notification do not increase.

When the user inputs a keyword indicating the intention to check the inventory and part of the nickname or the product name, the inventory list query Q-7 calls up the inventory data of the food material table T-2, and allows the user to edit the information including flags. FIG. 7 shows an example of calling the inventory check screen by a sentence and displaying each article. When a plurality of articles are retrieved, a plurality of similar screens are displayed. On this screen, the user can update a finished flag F2n indicating the presence or absence of inventory, the remarks D2r, the consideration D3r, the target consumption deadline T5r, or the like.

FIG. 6A and FIG. 6B are examples of confirmation screens of the inventory list query Q-7 in the information terminal 300 such as the smartphone 302. The user can list and display the articles in the inventory list query Q-7 in the information terminal 300 in order of the target consumption deadline T5r set as shown in the example in FIG. 6B. By doing so, the user can confirm the foods and the like that should be consumed preferentially. Since each article is managed by the storage spot L4e, the class C1e, the product name C2v, the purchase store R1e, the target consumption deadline T5r or the like, the user can devise a menu that should be preferentially consumed at home, and can easily make a consumption plan according to the purpose without waste.

The user can set various flags in the food material table T-2 by checking the check boxes on the screens as shown in FIGS. 6A and 6B, and the examples in FIG. 7. In the inventory list query Q-7, F1n and F2n, which represent unchecked in "finished" and "spare", are initially displayed. However, as shown in FIGS. 6A and 6B, the check box for a flag such as "finished", "spare" or "purchase" is displayed, and if the flag F2n is set to "finished" on the screen and changed to F2y, it will no longer be displayed in the stock list as being out of stock.

In addition, the user can set a flag in the food material table T-2 for the articles planned to be consumed from the confirmation screen of the inventory list query Q-7. In the example of FIGS. 6A and 6B, for fields Day1F5r, Day2F6r, and Day3F7r, labeled as D1, D2, and D3, the user can check the list of articles flagged from Day 1 to Day 3 in the food material plan query Q-4 by flagging the articles to be consumed for three days with the first day of the schedule as the first day, and can use the list as a reference for the planned use of the articles. Other than the target consumption deadline T5r, the user can also set an urgent flag F4o for articles to be consumed preferentially regardless of the expiration date.

By recording menus at the time of consumption recording of foods and other items at home, the user can check at a later date what menu those foods items were used for, referring to the fields for consideration, and can plan shopping and menus efficiently. In addition, it is possible to check what kind of menu can be prepared based on the inventory at that time. Since the ingredients are linked to the menu, it is possible to calculate the price for each menu by recording the price at the time of purchase and the quantity at the time of consumption. This system can be applied not only to food menus, but also to clothing combinations (coordination) and the like.

Figure 20:
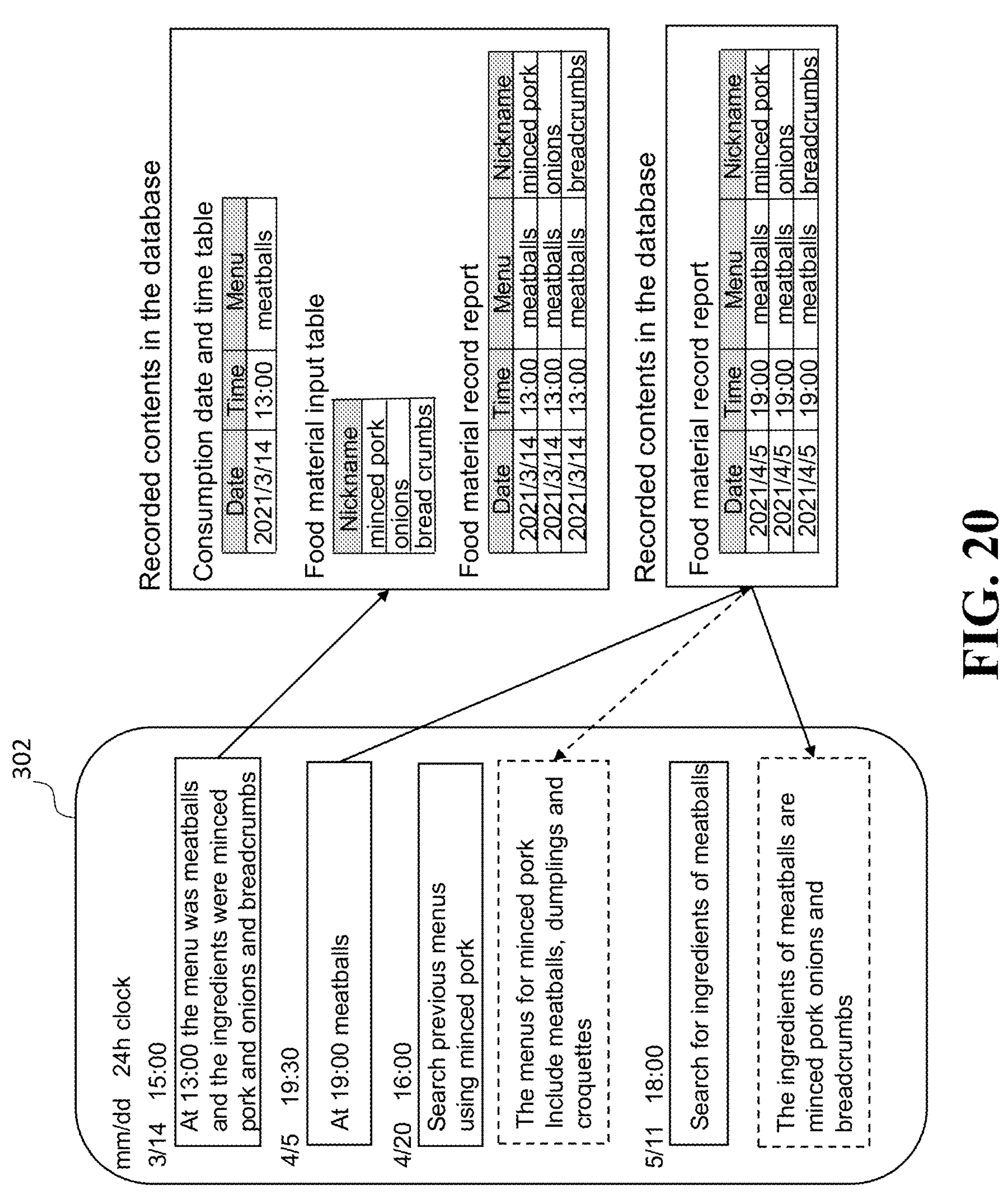
FIG. 20 is a diagram illustrating an example of a screen and processing related to menus.

Based on the input from the information terminal 300 by the user, the updating unit 103 can associate the article data with the menu. At the time of consumption recording, the user first selects the menu name E5s recorded in the menu table T-1 in the consumption date and time table T-3, and inputs the nicknames I1t of the articles which will be the ingredients of the menu in the food material input table T-6. Then the article is recorded in association with the menu E5c in the food material record report R-1. In the subsequent consumption recording, when the user inputs the menu name as the nickname I1t instead of individually entering the nicknames I1t of the articles, the notification unit 105 can extract the plurality of article data associated with the menu from the most recent data of the food material record report R-1. These data are confirmed by the user, or when the user does not confirm the articles constituting the menu, the updating unit 103 can directly record the consumption of the plurality of articles collectively constituting the menu. A combination of names of menus and nicknames of articles may be registered in another table so that the user can register menus directly or from the most recent data in the food material record report R-1 or the like. For example, a plurality of items may be collectively written down from a menu name such as "breakfast standard" and edited as necessary. In addition, in response to a request from the information terminal 300 used by the user, the notification unit 105 can retrieve, from the nickname of the article, the menus associated with the nickname of the article in the food material record report R-1 as described above, or retrieve the associated articles from the menu name, and transmit the search result to the information terminal 300 used by the user. In that case, the combination of the menu and the ingredients may be recorded in advance in a separate menu content table according to the input content such as "the standard breakfast menu is eggs and ketchup and ham and coffee and . . . ". FIG. 20 is a diagram showing an example of a screen and processing related to the menu.

Although it is possible to treat prepared foods separately from the menu, in the present embodiment, the prepared food names at the time of cooking using inventory articles at home or another place is also treated as the menu E5s. If the cooking method is recorded in the remarks Do in the menu table T-1, the recipe can also be recorded. As an example, when the user stores prepared foods such as "hamburger" cooked at home in a freezer, the updating unit 103 converts the dish "hamburger" from the menu name E5o to the product name C2o, and the converted product name "hamburger" can be handled in the same manner as the other items in the food material table T-2. At that time, articles associated with the menu E5o "hamburger" are written down in the remarks D1o of the food material record report R-1, so that the articles can be identified as ingredients. When the prepared menu is consumed later, the user can simply input the menu name newly recorded as the product name instead of the nicknames, and information including details of the ingredients such as "onion" and "flour" can be collectively written in the food material record report R-1, which is the consumption history. For inventory management, it is more convenient to handle prepared foods such as "hamburger" by the nickname of the prepared food instead of the ingredients. However, when analyzing physical condition as described later, for example, the prepared food can be made an object of analysis by setting up a field for it to distinguish from others and recording it separately from other articles, thus replacing the "hamburger" itself with articles such as "onion" or "flour" as ingredients.

In order to analyze in detail, the relationship between consumer lifestyle habits such as eating habits and physical condition and to improve the comfort of life by obtaining reference information for improving physical condition, it is desirable to keep accurate and detailed records for each individual. In the case where the physical condition changes every day for the consumer, the level of physical condition that the consumer can feel is converted into a numerical value at an appropriate time, including a minor level, and if the long-term tendency can be checked based on the continuous recording of quantified physical condition levels, it is useful to motivate the user to improve his/her lifestyle. By quantifying daily physical condition, the user can check the transition of the physical condition over a long period of time, and is less likely to miss minor changes in physical condition that are not necessarily illnesses, but are signs of poor health condition. In addition, since the user can record not only poor physical condition but also good physical condition, such data can be used as a reference for finding lifestyle habits that have positive effects on physical condition. By using the life information system 1, the user can become aware of the causal relationship between lifestyle habits and physical condition, can use it as a reference for improving lifestyle habits, and can obtain objective and post-verifiable analysis results.

The physical condition may include minor health conditions and mental mood states that the user would like to be aware of, as well as cosmetic skin and hair conditions. By the method of inputting text strings, contents can be set freely in a wide range. By recording mood as well as physical condition, it can also be applied to grasp the articles that bring comfort.

Information on the effects of foods on physical condition is relatively easy to obtain for each product name, but the main sources of information on the effects on physical condition of further subdivided brands are advertisements by sellers, making it difficult to guarantee objectivity. Although there is a system for third parties to evaluate tastes and atmospheres of restaurants and ready-made foods, there is no system for quantifying and evaluating the impact on the physical condition of individual consumers. Considering the environment where reliable information is insufficient and the differences in individual constitutions, in order to improve physical condition, instead of simply applying general evaluations to the subjects, it is necessary to analyze the records of the subjects themselves in detail.

Therefore, the life information system 1 provides the user with information on articles or stores which may influence physical condition based on the analysis result of correlation between time series records not only of the content of consumption of food and other articles in the home, but also the use of restaurants and ready-made foods, and records of physical condition that are quantified at regular time intervals.

Articles consumed to correlate with physical condition are not limited to foods. For example, it may be a scent of something. In the following, food is mainly explained as an example, but the life information system 1 also handles relationships between physical condition and articles including non-food items, and even covers slight changes in physical condition. For example, supplements and physical condition, cosmetics and skin condition, hair care products and scalp condition, toothpaste and gum condition, clothing and skin condition, and the like are covered. Further, it can be applied to the relationships between lifestyle habits such as sports and physical condition, and the relationships between various environmental factors and physical condition. These can be analyzed by combining various data.

The life information system 1 analyses the state of physical condition and consumption of articles, and provides advice to the user. Based on the user's input to the information terminal 300, the acquisition unit 101 can receive not only information on the consumption of articles but also information on the state of physical condition. When it is input by a sentence, it goes through the processing result by the inspection unit 102, but when it is input or selected by a character string to each data field directly from the screen of the information terminal 300 without using a sentence, the user-specific data of the database 110 is updated based on the data acquired by the updating unit 103 directly from the acquisition unit 101. For each user's physical condition of concern, such as "heartburn" or "diarrhea", for example, the most unpleasant time for the user in the past is set to level 3, and the system is designed to input the level E1o in the level table T-4 numerically each time the user experiences an uncomfortable physical condition. In the above example, if the physical condition is more uncomfortable than the most unpleasant time in the past, the user inputs a level 3 or higher, for example, 5. Level E1o is assumed to be an objective easy-to-understand index as far as possible, for example, level 2 is twice the diameter of level 1 for "eczema". A table describing the severity of each level may be created so that the user's input of the numerical value of the level does not fluctuate.

Prior to entering the physical condition level, the user registers the physical condition feature R4o in the physical condition table M-9. A plurality of secondary features can be optionally assigned to the physical condition in addition to the primary feature. For example, when the feature of the primary physical condition is "itchiness", examples of secondary features could be "scalp", "back", or the like. The user can freely register these features and input a plurality of secondary features in addition to one primary feature. FIG. 8 shows an example of a physical condition event input in the form of a sentence, in which the word "level" is processed as having an intention to record a physical condition event. In addition, when only the word "level" is input without any feature input, this is an example of a case where a rule has been established according to the user's prior setting that "itchiness" is recorded. If there is no such agreement, the feature input in the sentence is recorded as the feature R4s of the level table T-4 as it is, together with the level E1o, after being matched with the feature R4o in the physical condition table M-9.

Since there may be cases where the user frequently inputs physical condition events, and events with the same main physical condition feature R4o (hereinafter referred to as events of the same type) persist, a rule is established that events of the same type are counted at regular intervals, for example, only once in one hour. When a plurality of events are recorded within a predetermined time, the analysis unit 104 gives priority to the physical condition having a higher absolute level of intensity, identifies the target event, and makes it the subject of the conversion value calculation described below. As a result, it is possible to analyze changes in physical condition over a period longer than the timing of individual inputs, such as one week or one month. Depending on the nature of the physical condition, the recording may be not only once in one hour as in the above example, but shorter than that, or may be adjusted to an interval such as only once in a day or in a week. The influence of physical condition events excluded from the conversion value calculation due to their small levels are considered to be represented by physical condition events that are included in the conversion value calculation, and do not affect the process of identifying causative substances explained below.

Figure 10:
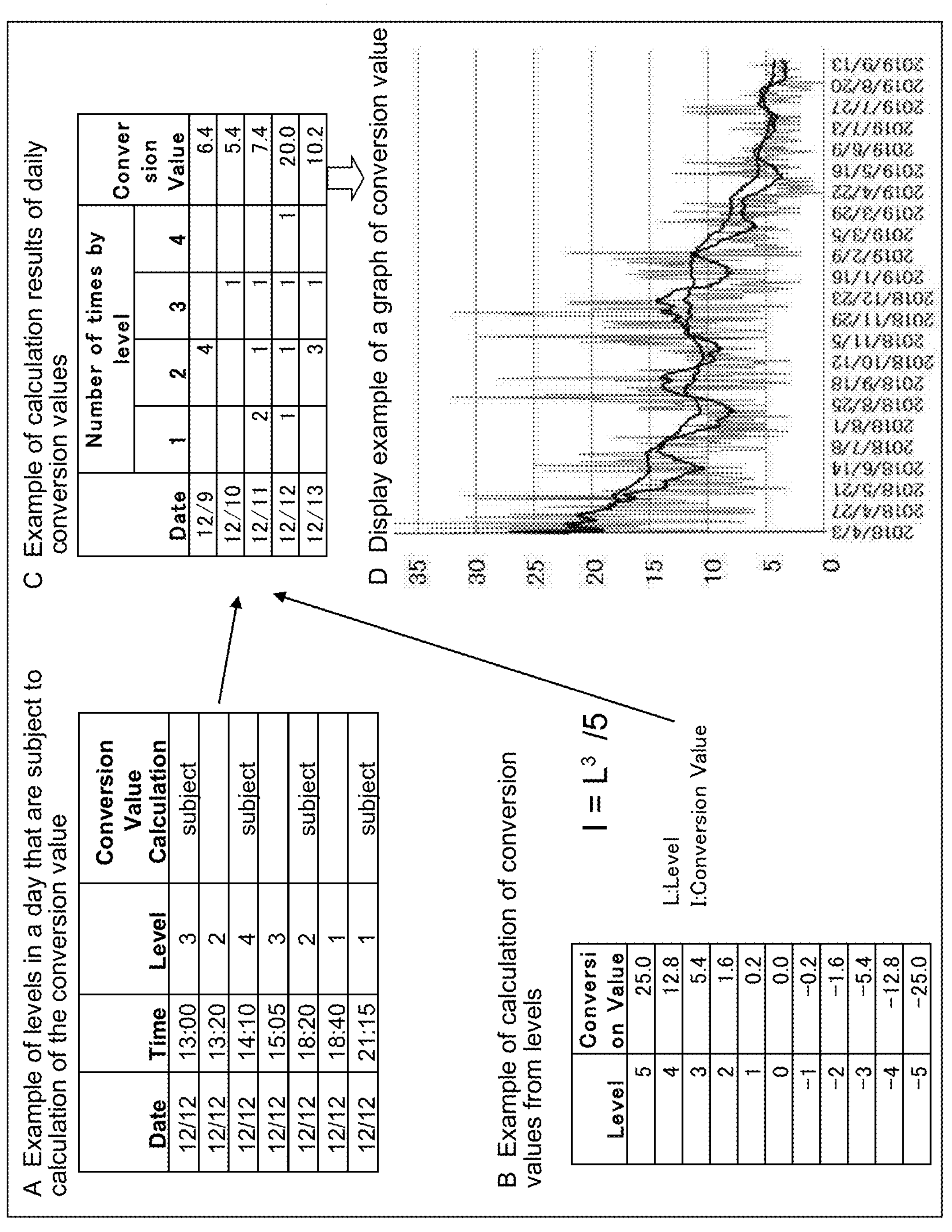
FIG. 10 shows a calculation example of a physical condition level and a conversion value, and a display example of a screen.

The level E1o is for grasping the physical condition as a numerical value, and it can be aggregated as it is. However, in the present embodiment, the numerical values are not simply added up, and further conversion calculation is performed from the level to the conversion value in order to bring the degree of good or poor physical condition closer to the user's experience, assuming that there are strengths and weaknesses in the causes of the physical condition. Specifically, the conversion value A2i of the conversion value report R-4 is calculated based on a certain calculation method from level E1o, and the conversion value A2i is aggregated and analyzed. FIG. 10 shows a calculation example of the conversion values A2i from input levels E1o and a display example of a graph of the conversion values. In this example, if the level is L and the conversion value is I, calculation is performed by the following formula:

$$I=L^3/5$$

In this case, as shown in B of FIG. 10, the conversion value for level 2 is 1.6, the conversion value for level 3 is 5.4, and the conversion value for level 4 is 12.8. Since it is possible to input 0.5 as a level, it is possible to flexibly cope with a situation in which opportunities for inputs of level 1 or less increase in the aspects in which, for example, unpleasant physical conditions are improving. This method can be used as a guideline for measuring the level of good condition instead of the discomfort level by reversing the positive and negative of the level, depending on the situation. Since the purpose of using the numerical formula as in the above example is to analyze by replacing subjective matter with a numerical value, the numerical formula may be set as in the embodiment, or may be modified so that the user can feel that it best represents his/her physical condition. As another embodiment, the input level may be used as it is without performing the conversion value calculation, or data input by means of an index other than the numerical value may be converted into a numerical value in the same manner as the conversion value described below. A value quantified in chronological order based on data of a physical condition event, including the conversion value described in the present embodiment, to represent the transition of the degree of good or poor physical condition, is referred to as the physical condition level value. The data serving as the source of the physical condition level value calculation may be, for example, data such as a weight or a blood pressure acquired from an input of a user or another device.

A of FIG. 10 is an example of a time series of the physical condition events of the same type for which, the primary feature R4o of the physical condition is "itchiness", and the fixed time interval is set to every hour. In this example, four out of the seven physical condition events recorded in the level table T-4 on December 12th are subjects for the conversion value calculation. In this example, subject physical condition events are identified in descending order of the levels within the calculation period in a day, provided that events that are less than one hour apart from already qualified subject events are excluded according to a rule. B of FIG. 10 is a calculation example showing the correspondence relationship between the conversion values from the levels based on the above numerical formula. C of FIG. 10 is a calculation example showing that the levels E1o set to be the calculation subjects in A of FIG. 10 are aggregated in the conversion value report R-4, then replaced by the conversion values A2i by the method of B in FIG. 10, and the conversion values for each day are aggregated in the right column. D of FIG. 10 is an example in which the daily converted values counted in this way are aggregated over a long period of one year or more and represented graphically. A moving average line is displayed on the graph, allowing users to see long-term trends without worrying about daily fluctuations.

For detailed analysis of state of physical condition and consumptions of articles, it is desirable that the user inputs the status from purchase to consumption of articles from the information terminal 300 for the articles he/she wishes to record in his/her daily life. However, if there is at least a record of the articles consumed, it is possible to compare the record with the physical condition or with the target consumption pace. In this case, the user needs to input information such as the date and time T1t, the nicknames I1t for recognizing article items and the like, as the contents of articles consumed. As a result, it is possible to check the evaluation results of the influence on physical condition of each brand of articles, store of articles or restaurant.

The analysis unit 104 separates the foodstuffs and other articles consumed by the user prior to a physical condition event by an arbitrary time selected by the user in advance (hereinafter referred to as the observation time), such as six hours, for example, extracts from the database 110 the articles consumed within the observation time, such as six hours from the occurrence of the target physical condition event, and extracts those with high scores as suspect causative articles. Initially, the observation time may start out short-term and then be expanded, for example, to one day, then to one week, and a desired time period depending on the situation. By switching the observation time, the scores of the article items described below vary.

In accordance with the occurrences of physical condition levels after consumption, the article items are given a possibility % A4i which is a possibility degree value indicating the degree of possibility of the cause of a physical condition in the score report R-5, and the latest information is maintained for each article item. As an example, the possibility % changes as follows. Since the possibility of a new article is unknown, it starts at 50%, and unless a level value is entered that means that the physical condition is poor within the observation time after the first consumption (hereinafter, such a case is called a "problem"), the possibility % is set to 0%. If there is no problem within the observation time, the possibility % of all other articles consumed during that time will also be 0%. If a problem occurs within the observation time, 100% prorated by the possibility % of each article is added to the possibility % of the articles consumed during that time. A possibility % of an article exceeding 100%, as a result, is replaced by the upper limit of 100%. However, if there is an item whose possibility % has already reached 100% among a plurality of items consumed at the same time, the possibilities % of the other articles are not changed and are left unchanged. Also, if the possibilities % of a plurality of articles consumed at the same time are all 0%, 100% is evenly prorated to each article.

As an example, if two articles are consumed within the observation time and there is a problem, assuming that the first article item is 50% and the second is 0% at that time, the % is added only to the first item thereby exceeding 100%, but leaving the maximum at 100%. At 100%, the article is most likely the cause of a particular physical condition. When the possibility % reaches 100%, it is desirable not to consume the article, but if a problem arises when consuming it with other articles, the possibility % of the other articles will not be changed, and the article having a possibility % of 100% is deemed to be a cause of the problem. It should be noted that for a single physical condition event, there is not necessarily a single item that may be the cause of the event.

In addition to the above possibility % calculation method, when testing the reaction of physical condition by suppressing the consumption of a specific article to a small amount, when recording the amount due to fluctuations in the amount consumed each time, or when a substance is contained whose effect on the physical condition is already known from another source, such cases can be treated differently by other methods such as including keywords to that effect separately defined in the current memo M1t of the food material table T-2. Also, when poor physical condition occurs frequently, only physical condition events above a certain level may be treated as factors for changing the possibility % A4i. Alternatively, for the purpose of reflecting freshness of foods and the like, an additional calculation method may be used, such as treating the number of days elapsed since the date of acquisition as a factor that changes the possibility % A4i, or, as an example, adding a field in the food material table T-2 in addition to the target expiration date T5o of the food, recording the expiration date indicated on the food, and treating the number of days remaining from the date of consumption to the expiration date as a factor that changes the possibility % A4i.

Regarding the consumption of articles within the observation time going back from the physical condition event, a score Abi of each article item having the possibility % A4i is the mean value of scores A5i in the food material record report R-1 for each article item traced back to past records which are obtained by prorating the conversion value A2i at the time of the physical condition events to the article items on the basis of the latest possibility % A4i. This calculation method is an example, and other adjustments may be made such as increasing the score of an event close to the consumption of an article within the observation time, or may refer to the knowledge base 111 to change the score depending on the physical condition feature R4o and the lapse of time within the observation time. Candidates for articles that cause a physical condition event are those articles with the high scores A6i among articles consumed within the observation time prior to the timing of the physical condition event.

In the food material record report R-1, a possibility % A4c for the article item is recorded as of that time, but the score A5i is calculated and updated with the latest possibility % A4i of the score report R-5. The score A6i for each article item in the score report R-5 is calculated as the average of the scores A5i in the food material record report R-1. It is considered that the higher the score A6i, the greater the influence and the more likely it is to be a causative agent of fluctuations in physical condition.

E of FIG. 11 shows an example of the consumption status of article items and the transition of the possibility % depending on the presence or absence of a problem, assuming the example in A of FIG. 10. When the observation time is 6 hours after consuming a specific article item, it is shown how the possibility % A4c before consumption of the article has changed depending on whether a level indicating a problem of poor physical condition is recorded within 6 hours. The possibility % changes according to the state of physical condition events, but is calculated using the latest possibility % A4i at the time of analysis, as described in the "possibility % update status" in the figure.

In this example, article items 1 and 2 had no problems within 6 hours of consumption, and the possibility % is updated to 0% for both. Since article items 3 to 8 consumed at 12:00 am had problems at 13:00 and 14:10 after they were consumed, the possibilities % was increased by adding 100% prorated by the ratio of the possibility % before consumption. Article items 4 and 8 were also consumed along with the other articles at 17:30. Article item 1, which was consumed at first, was also consumed again. For articles consumed at 17:30, there were problems later at 18:20 and 21:15, thus the possibility % prorated to 100% by the ratio of the possibility % before consumption was added to each article item. Since the article item 1 was 0% before the calculation, the article item 1 remains the same at 0% after the calculation, and the article item 9, whose calculation result is 131%, is replaced by 100% because the upper limit is 100%.

F of FIG. 12 shows that the physical condition event subject to conversion value calculation in A of FIG. 10 is converted from the recorded level according to the calculation example in B of FIG. 10, and the updated possibility % whose "update status of possibility %" is the latest in E of FIG. 11 is assigned to the physical condition event within 6 hours after the consumption of each article item. In G of FIG. 12, the converted value of each physical condition event is averaged for each article item and the latest score A6i is calculated by averaging the score A5i for each physical condition event prorated by the possibility % of the article item assigned to the physical condition event in F of FIG. 12. Thus, the score report R-5 holds the latest information as the score A6i of the article item. In this example, the article item 5 is the most likely cause of the poor physical condition for the day, followed by the article items 7 and 6.

Articles like article item 9, although they have a high possibility %, have a lesser level of post-consumption malaise and so have a relatively low score. As another example, in the case of an article item that had a 0% possibility % 5 or more times in the past, for example, if a problem occurs after a new article is consumed and the possibility % that the article item caused the problem is now 100%, then the raw material of the item may have changed. It is possible to include a flag for this effect in the remarks D1o to indicate this, or to treat the new article as if it were a different article item from the one consumed in the past by removing the article from the food material table T-2 as a terminated article if there have been no problems with it in the past.

Figure 19:
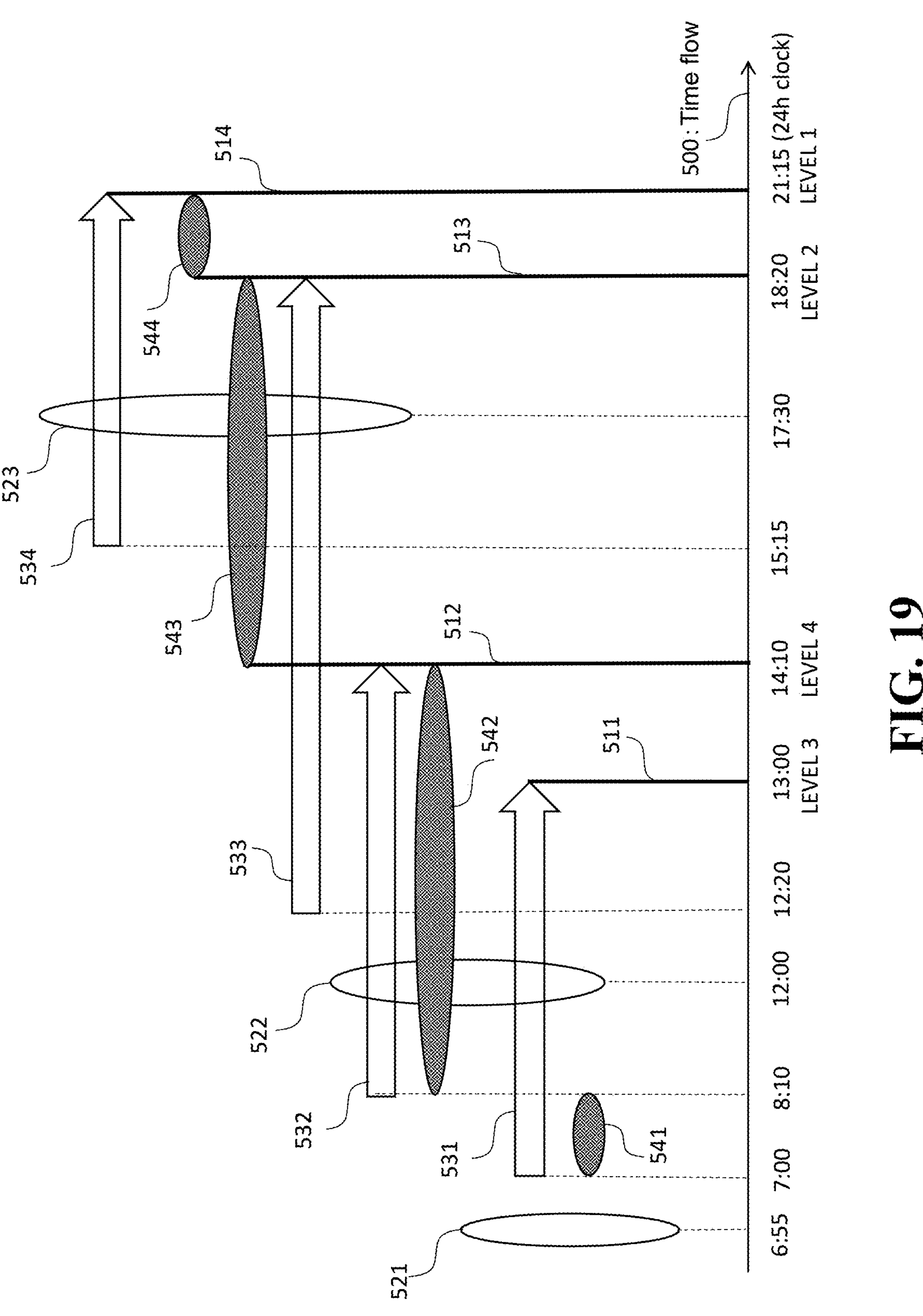
FIG. 19 is an example of observation times and analysis target group ranges according to a state of events.

FIG. 11 shows an example in which the occurrence timings of article consumption events are simplified, however, as a variation, there may be a case in which article consumption events are performed not only once but also a plurality of times at different timings in the observation time traced back from a particular physical condition event. In such case, a pro-rata percentage of 100% is added to the overall consumptions of the subject articles during the observation time. As an example, even if the consumption times of article items 3 and 4 in FIG. 11 are not 12:00, but 11:50 and 12:10 respectively, the calculation result of the scores does not change. Even if there are physical condition events for which the conversion values are calculated multiple times during the observation time, the % prorated for 100% is added to the article item only once. When there are physical condition events subject to a plurality of conversion value calculations within the observation time, a group of consumed article items is created with reference to the physical condition event with maximum converted value within the observation time after the consumption of the articles, and 100% is prorated accordingly. FIG. 19 shows an example of observation times and analysis target group ranges according to a state of events.

Figure 14:
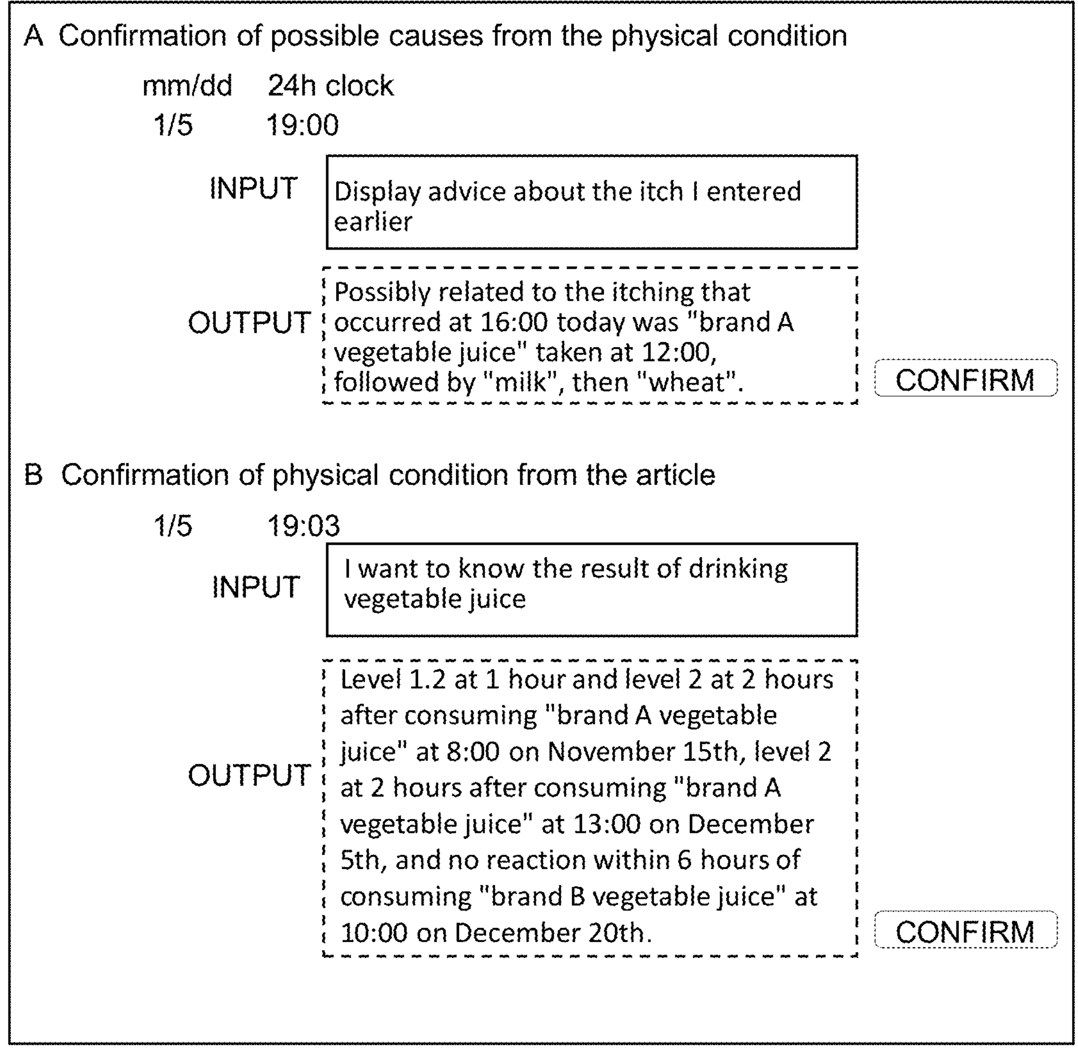
FIG. 14 is a display example of a screen for confirming reference information related to the consumption of articles and physical condition.

According to the analysis results obtained by the analysis unit 104, the notification unit 105 can extract article items with the high score A6i such as the highest score among the items consumed the previous day, or three items in order of the highest score, on a daily basis using a pre-defined method, and send a notification to the information terminal 300 used by the user. The user can refer to the notification for the consumption of articles, such as reducing the consumption of the corresponding article item, or increasing the consumption of the article item that is likely to be the cause of good condition contrary to the cause of poor condition, or the like. A of FIG. 14 shows an example in which a response is output when a specific inquiry is entered from the information terminal 300 used by the user.

When the user uses a restaurant or a ready-made meal, the consumption date and time T2o, the store R3o, the menu E4o, and features such as the main or worrisome raw material names, production area, quantity, or the like as the content D6o are entered into the eating out table T-5. Since consumers are unlikely to know all the raw materials used in restaurant and ready-made-meals, it is assumed that the quality of raw materials, combinations per menu, cooking methods, etc., are stable from restaurant to restaurant. The mandatory input items by users are limited to store/restaurant names and menu names, and input of raw materials is not mandatory, but only limited to what are noticed. The fourth entry box in FIG. 8 is an example of such an entry. If the name of the same menu E4o of the same restaurant does not list raw materials in the second and subsequent contents D6o, the contents of the previous description may be used as a reference. In the case of using a restaurant or a ready-made store, not only the input raw materials but also the restaurant itself or the restaurant menu itself are subject to analysis. Even if there is no detailed input of raw materials, the data is analyzed for each user in the same manner as for the article item, based on the input of the physical condition after using the restaurant. For example, when the user's physical condition becomes worse after eating the same menu at the same restaurant multiple times, the analysis will indicate that the menu item at that restaurant requires caution.

The raw materials recorded in the contents D6o for eating out and ready-made meals, the article items such as food when consumed at home, and the raw materials recorded in the remarks D1o of the food material table T-2 are used for analysis of correlation at a more detailed level by the analysis unit 104, and if the same character string is detected, it can be analyzed in the same manner if a food with the same product name had been ingested. For example, when eating out, if the menu is "pancakes" with "honey" listed as a raw material, and if "honey" is included in the product name of the articles consumed at home, in that case, both can be regarded as ingesting "honey", and can be analyzed for correlation with the physical condition.

The food material record report R-1 is a time-series record of the articles in the food material table T-2 that have been consumed. The food material and level report R-2 is integrated from the food record report R-1, the eating out table T-5 and the level table T-4. A reaction confirmation report R-3 is created by first extracting the consumption events of articles from the integrated food material and the level report R-2 from a part of the specific article name input to the field of a nickname I4o for search, and then by extracting the physical condition data within a predetermined time from the consumption events of the extracted article. For the purpose of creating the reaction confirmation report R-3, some of the specific article names to be input in the field of the nickname I4o are searched by partial matching from not only the nickname A3i in the nickname query Q-1, but also a product name C2w, a remarks D1v, a current memo M1v, a restaurant menu E4v, raw material names included in a content D6v, or the like.

It is possible to extract, without omission, the contents entered by the user in the past if the corresponding character string is included.

Figure 13:
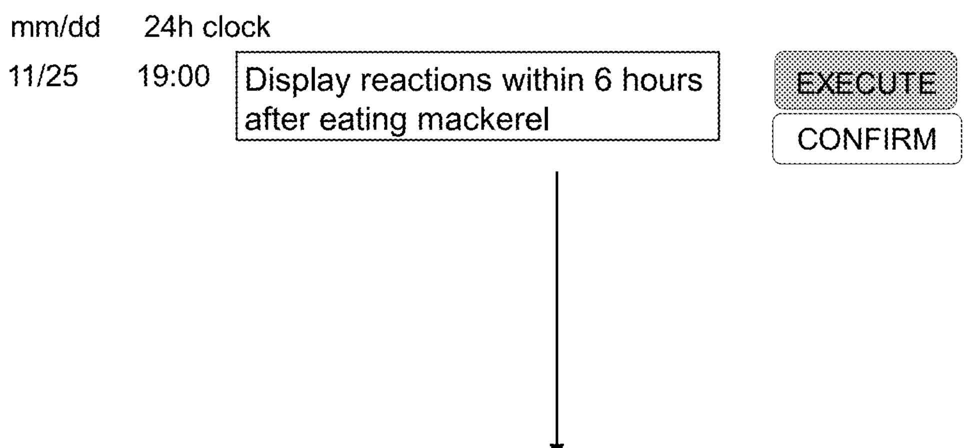
FIG. 13 is a display example of a screen for confirmation of reactions relating to the consumption of articles and physical condition.

Using the reaction confirmation report R-3, B of FIG. 14 is an example of checking the physical condition by a sentence after consumption of the article, and FIG. 13 is an example of outputting the physical condition check result after consumption of the article in tabular format. As shown in the example of B of FIG. 14, when the user inputs a keyword related to the article regarding the past consumption of the article, the notification unit 105 shows the past consumption records of the article, extracts the information on the physical condition within a certain time from the consumption dates and times of the article from the database 110, and transmits the data, and the results are then displayed in a list on the information terminal 300. The elapsed time is set to be an observation time unless otherwise specified by the user. B of FIG. 14 is an example in which the observation time is 6 hours.

Since information on foods and the like that may affect the physical condition of an individual is enormous and it is difficult for individuals and medical personnel to comprehensively collect information, the life information system 1 uses actual data of other consumers accumulated in the knowledge base 111. The analysis unit 104 accumulates the information obtained from the database 110 in the knowledge base 111 for reference to other users, to the extent permission of data use has been obtained from the users in advance, among data such as the analysis results of the correlations between the individual users' consumptions of the articles and their physical condition. Furthermore, the knowledge base 111 accumulates consumer data collected from information sources outside the life information system 1, such as data on the raw materials of articles, data on the dynamics of substances taken into the human body, data on recommended articles, and the like.

When analyzing the correlation between the consumption of articles by the user and the physical condition recorded in the database 110 not only for the records of individual users but also for the data of other consumers, the analysis unit 104 refers to the data of the knowledge base 111, such as product names and article items that affect physical condition having similar features, to infer article items that are likely to affect the physical condition of the user at an early stage before the individual user's records are sufficiently accumulated, and transmits them from the notification unit 105 to the user for reference information.

In addition, the analysis unit 104 may use the results of machine learning of the correlation between the consumption of articles and the actual physical condition data of other consumers stored in the knowledge base 111, based on consumption records and physical condition data of users recorded in the database 110, may predict articles that are likely to affect the user's physical condition or the timing at which the physical condition is likely to be affected after consumption of specific items, and may provide this information to the user as reference information, or it may be reflected in the method of calculating the possibility % and score described above.

The lifestyle event includes a lifestyle habit event, a physical condition event and the like. A lifestyle habit item is a type of lifestyle habit corresponding to a lifestyle habit event, and includes articles such as foods and the like. The life information system 1 can also record and analyze other lifestyle habits as lifestyle habit, such as "running", and various environmental factors as factors that affect physical conditions as well as the consumption of articles, as lifestyle habit items. In the case where the lifestyle habit or the consumption of the article continues for a long period of time, the time and the period may be input with a sentence such as "I did . . . from . . . to . . . " or "I do . . . every day from today" as an example. Physical condition events can also be input by a sentence such as "level 2 from 13:00 to 17:00" or "level 1 at 9:00 and 10:00".

If the user wants to treat a substance contained in food or the like as a subject for management, the user can first specify substances such as "protein" or "calcium", for which the user wants to check the consumption amount and treat as a subject for management. When the substance to be managed is not the article item itself but the content of the article item, in order to calculate the inclusion amount, it is presumed that it is recorded as an inclusion E6o of the inclusion conversion table M-10. The inclusion conversion table M-10 may be set separately according to a request from the user, or may be set by the analysis unit 104 with reference to the knowledge base 111.

Figure 21:
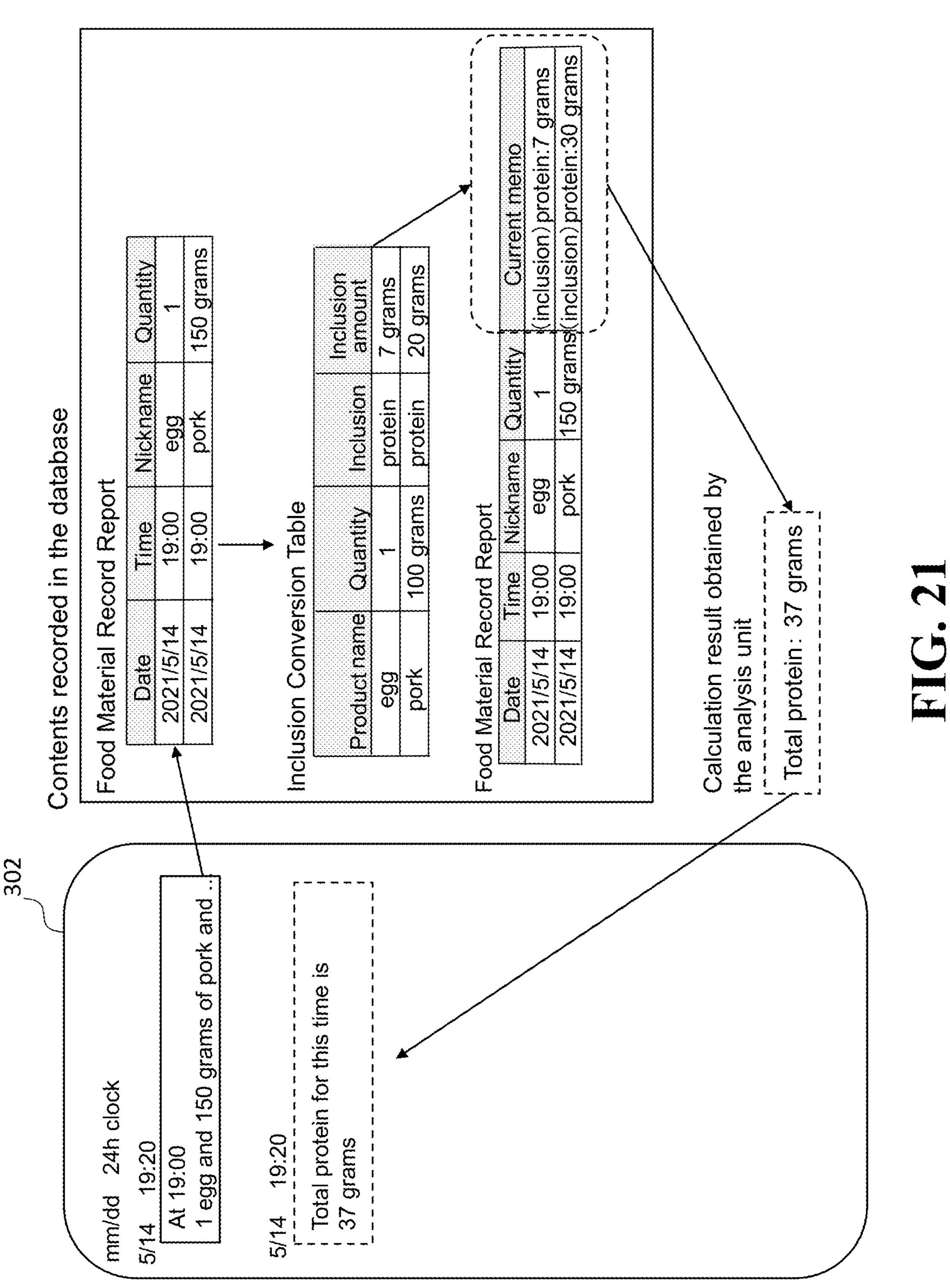
FIG. 21 is a diagram illustrating an example of a screen and processing related to the intake amounts of inclusion.

The user can input the amount of food consumed, for example, by a sentence such as "One egg and 150 grams of pork and . . . ", based on the input to the information terminal 300 used by the user. Using the data of the correspondence between a quantity Q3o of the article in the food material record report R-1 based on the above inputs, and the data of a quantity Q4o, the inclusion E6o and an inclusion amount Q5o in the inclusion conversion table M-10, the updating unit 103 calculates the quantity of the inclusion E6o contained in the consumed article, and records the name of the inclusion and the calculated inclusion amount at the time of consumption of the corresponding article in the current memo M2o of the food material record report R-1, and then the analysis unit 104 aggregates them. The fields "current memo" and "remarks" in the food material record report R-1 can be used for multiple purposes by including a character string or a mark indicating the content of the information, and the analysis unit 104 and the notification unit 105 can extract the necessary information according to the purposes. From these data, the analysis unit 104 can analyze the correlation between changes in intake of specific substances and changes in physical condition, and the notification unit 105 can transmit the analysis results to the information terminal 300 used by the user. FIG. 21 is a diagram showing an example of a screen and processing relating to the intake amount of an inclusion.

The inclusion E6o corresponding to the product name C3o in the inclusion conversion table M-10 becomes a subject for calculation when the product name C3o matches the product name C2o in the food material record report R-1. In order to perform conversion calculations in more detail, a conversion table may be provided not only for product names, but also for article items for which information can be obtained. The quantity of the article to be used as the basis for the calculation is entered as a combination of a numerical value and a unit, such as 3 grams, into a quantity Q3t in the food material input table T-6, and is transcribed into the quantity Q3o in the food material record report R-1. In the quantity Q4o in the inclusion conversion table M-10, a standard quantity such as "1 gram" is recorded. The conversion is performed from the inclusion E6o and the inclusion amount Q5o per base quantity for each product name C3o. The data recorded in the food material record report R-1 on the inclusion amounts at the time of consumption of the inclusion is used for analysis of correlation with physical condition by the analysis unit 104, as well as for comparative analysis between consumption targets and actual results, which will be described later.

In order to compare the specific substance designated by the user as a target of management with the physical condition, as an example calculated as in C of FIG. 10, the transition of the daily total conversion value of the physical condition and the transition of the daily total intake amount of the specific substance can be compared. For example, if there is a tendency for the total conversion value of the physical condition to increase when the total daily intake of a substance increases, it can be presumed that the intake of that substance is causing a deterioration in the physical condition. As in this example, when the conversion values of the physical condition are aggregated for each day, the aggregation timings can be standardized by collecting the intake amounts of the substance for each day. As an example, such a correlation can be presumed from the average of the ratio of the rate of increase in total daily intake amounts of the particular substance to the rate of increase in total daily conversion values of physical condition. The aggregation timing may be weekly or monthly, and it is possible to adjust the timing depending on the substance to be managed or the nature of the physical condition. Note that the substance to be managed may be a substance contained in one or a plurality of article items, or may be one or a plurality of article items themselves.

In the case of a substance that takes time to reach its maximum effect after intake, or a substance that has a long-lasting effect on the human body and tends to accumulate under normal intake conditions, not only the intake amount but also information stored in the knowledge base 111 regarding the timing of the maximum effect of the substance on the body condition immediately after ingestion, half-life, or other information, can be used to estimate the amount of substances accumulated in the body at each time point to compare them with the physical condition. Additionally, health-related measurements such as gender, weight, height, blood pressure, body fat percentage, and the like may be obtained separately by the user to adjust the estimated value of the amount of the accumulated substance in the body. The analysis unit 104 may predict the physical condition of the user when the intake of a specific substance designated by the user is increased or decreased, based on the user's past results or data stored in the knowledge base 111 by machine learning. The estimated cumulative amount in the body of the specific substance in the article consumed by the subject consumer can also be calculated from the standard intake amount per each product name obtained from the knowledge base 111, even when the consumption quantity is not input at the time of consumption.

For consumers, when purchasing a large number of articles from many stores, it is difficult to remember every detail on the articles from each store, and relying on memory to make purchases can easily lead to waste. However, in the life information system 1, the user can input comments in the field of consideration about articles, restaurant menus or the like, based on individual subjective views, and can always refer to the latest information. By displaying consideration lists for each store/restaurant, each class of article, each product name of articles or the like, the user can use them as a reference when making another purchase. Furthermore, if price information is also entered, it is possible to check the cost-performance of articles or stores/restaurants.

Specifically, the user inputs a comment in the field "consideration" such as a consideration D8o of the store table M-4, a consideration D9o of the menu table T-1, and a consideration D3o of the food material table T-2. For example, when a physical condition becomes poor by eating a certain food raw, and an allergic symptom is generated each time, a comment which is easy for the user to understand such as "dangerous without heating" can be mentioned. On the screen of the reaction confirmation report R-3 as shown in the example of FIG. 13, the user can view and edit the considerations (D3r, D4r, D5r) which are the latest comments. The consideration D3o for a food material is written as D3c in the food material record report R-1 when the food material is consumed, but D3c is a record at the time of writing and is not the latest information. D3o is always overwritten with the latest information, and D3r matches its contents. Other types of consideration are similar. The consideration D5o for restaurants applies to menus. If the user eats only one menu at one restaurant, the contents of the consideration D5o will be a comment to the restaurant, but if the user has the opportunity to eat more than one menu, a plurality of comments will be given to the single restaurant.

Consideration is not only based on the experience and the consideration of the user, but also reference information can be added from the knowledge base 111. In addition to the above consideration field, flags such as "delicious", "good", "bad", "need caution", "observation required", "no repeat", or the like, can be set to allow multiple selections for each item. None of these is an essential requirement.

By recording actual consumption of articles that the user thinks should be increased, decreased, or kept at a certain pace, the life information system 1 allows the user to easily compare the pace of consumption of articles with the preset target consumption pace, thus motivating the user to approach the target. For example, it can be used for the purpose of quitting smoking, or preventing the user from forgetting to take medicine.

At first, the user sets a target consumption pace for an article that the user wishes to manage. In the case of an article to be consumed at an even pace, for example, a target consumption pace of one tablet three times a day in the case of supplements is set. Alternatively, a target consumption pace is set for articles whose consumption is to be reduced, for example, cigarettes, which are to be reduced in stages to zero after a certain period of time. This setting may be done by sentences, or by inputting numerical values on the screen of the terminal and selecting the method from a list of options. The analysis unit 104 compares the daily target consumption quantity calculated from the target consumption pace for the target article with the actual result of the consumption quantity input by the user and recorded in the food material record report R-1, and the notification unit 105 can transmit advice based on the comparison results or, if the frequency of the user input is below the expected frequency, a notification to the information terminal 300 used by user to confirm consumption or not.

This method can be applied not only to the article itself but also to the inclusion E6o contained in the article using the inclusion conversion table M-10. In that case, consumption targets are set for specific substances based on the user's requests. For example, even if a plurality of different articles are consumed in a day, if the substance contained in the article is the same for which the user wants to set a target value, the consumption amounts of those articles are converted into the inclusion amounts of the target substance, aggregated as a daily consumption quantity, and compared with the target value.

Figure 17:
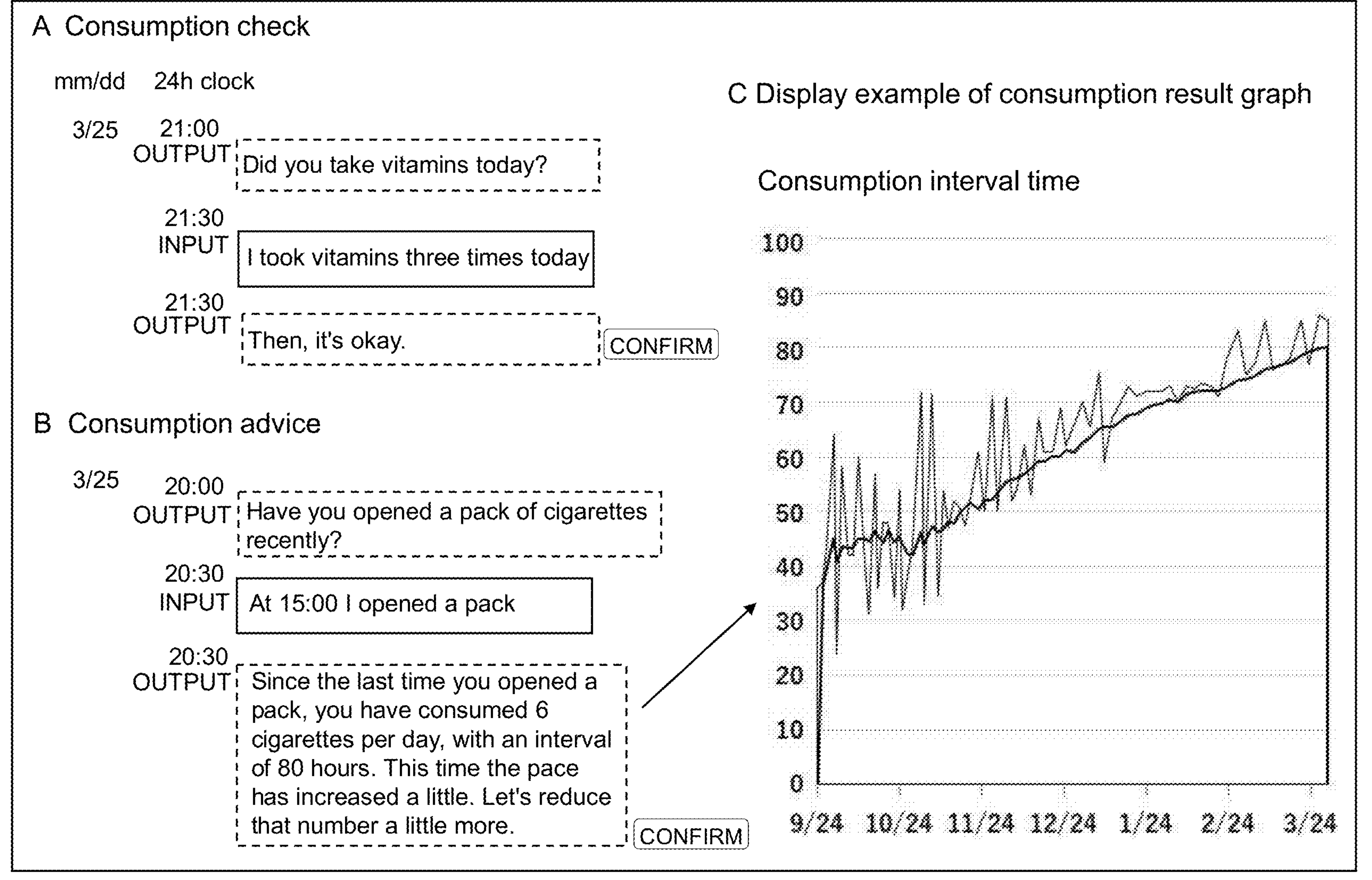
FIG. 17 shows a display example of a screen of consumption results and targets.

In the example of "vitamin" in A of FIG. 17, the user has set a target to take one tablet of vitamin supplement after each meal three times a day, and since there is no input of the consumption result at 21:00, a notification requesting confirmation is displayed. In the example of the user's response in A of FIG. 17, although no time was input, the number of times, "three times" was input, thus the consumption was recorded at that time and there was no difference from the targeted number of vitamin consumptions, and this input was treated as no problem. In the example of cigarettes in B of FIG. 17, the consumed amount is grasped by the pack, but the analysis unit 104 calculates the number of cigarettes consumed per day in more detail and sends advice to the user as reference information. The user can input the actual consumption for each cigarette, but can also input for each pack of cigarettes as in the example in B of FIG. 17. In this example, the "pack" is a nickname representing an article item of " . . . brand cigarettes" containing 2o cigarettes, and the user can record the pace of consumption by simply inputting the sentence "Opened a pack" without having to record the number of cigarettes every time. C of FIG. 17 is an example of graphical display of the consumption interval time of a pack of cigarettes based on the actual consumption result input by the method of the example in B of FIG. 17, and it can be seen that the greater the consumption interval, the closer the user is to that target. The notification unit 105 can transmit data for displaying such a graph on the information terminal 300 used by the user.

A supplementary explanation of FIG. 3 is as follows. When data in the form of a sentence is input to the information terminal 300 used by the user, processing is performed in the server 100 in the following sequence: the sentence is inspected, the intention is recognized, a table corresponding to the intention is selected, the nicknames are extracted from the remaining character string, data is extracted from the table where nicknames match and information on articles corresponding to the nicknames are recorded corresponding to the intention, and then the database 110 is updated. As an example of processing corresponding to the intention, the consumption record table is updated if the sentence contains the character string "What I ate", and the purchase record table is updated if the sentence contains the character string "What I bought". In addition, as an example of extracting the nicknames, the nicknames I1t of "banana" and "chocolate bar" are extracted from the sentence "What I ate was bananas and a chocolate bar . . . ", and the nicknames I1t of the extracted articles are made to correspond to the existing article nicknames A3i in the database 110. Then, the data of the article item of the product name C2s "banana" of the class C1s "fruit", and the article item of the product name C2s "chocolate bar" of the class C1s "confectionery", is extracted. Assuming that information on the brand E2o and the deadline T5o is also recorded for these items, not only the class C1s and the product name C2s, but also information on a plurality of items such as the brand E2o and deadline T5o, is linked and extracted corresponding to the nickname I1t such as "banana" or "chocolate bar". At the time of the consumption record of these article items corresponding to the character string "What I ate", information on a plurality of fields is recorded in the food material record report R-1 as well as a nickname A3c. The table at the lower right of FIG. 3 shows an example of data in the database 110. In the case of "banana", the alias E3o is not specified, thus "banana" which is the product name C2s, is treated as the nickname A3c as it is, while in the case of "chocolate", the alias E3o, which is "chocolate bar", is an example of "chocolate bar" being treated as the nickname A3c. The fields of these data examples are excerpts, and are not limited to those shown in the figure. The same is true for other figures.

Supplementary explanations of FIGS. 4A and 4B are as follows. FIG. 4A is a diagram showing a flow of a method of specifying an article item and a method of determining its nickname. With regard to recording in the food material table T-2 for an article item which is new or at the time of data update based on the input to the information terminal 300 by the user, since the product name C2s is mandatory, in addition to that, if there is information on the brand E2o, the article item is specified by the combination of the brand E2o and the product name C2s, and if there is no information on the brand E2o, it is specified by the combination of the store name R1o and the product name C2s. The nickname A3i is a keyword that makes it easier for the user to call up the data of the article item specified as described above in this way from the database 110. For example, if the product name C2s alone would cause confusion with another article item owned by the user, the user can register the alias E3o for the article item, and can use the alias E3o as the nickname A3i when calling up the data thereafter. If the alias E3o is not registered, the product name C2s is used as the nickname A3i. This is to make it easier for the user to identify the article item. For example, when purchasing many coffee beans of different brands at the same store, the combination of the store name R1o and the product name C2s is usually insufficient and the brand E2o information is required, but if the user does not need to distinguish between the brands E2o, such as when they are similar but only slightly different, it is possible not to input the brand E2o information, and the operation can be made flexible according to the user's needs. FIG. 4B is a diagram illustrating a flow of a method of allocating an article item such as at the time of acquisition. By using the nickname A3i (existing nickname) registered in the database 110 according to the flow in FIG. 4A, when data is added to the field of the nickname I3t in the purchase content table T-8 for a newly acquired article item, and a match is confirmed between the new item and the existing nickname A3i, it is assigned to the existing article item, and information such as the brand E2o, the consideration D3o or the like is copied from the data of the existing article item. If the input nickname I3t does not match either the existing nickname A3i or the existing product name C2o, it is registered as an article item with a new product name C2o. Even if the input nickname I3t matches the existing product name C2o, but the identity cannot be determined from the information on the brand E2o or the store R1o, the new article item of the existing product name C2o is registered, and the new article item is determined by the nickname A3i according to the flow in FIG. 4A. If the alias E3o is not set and multiple article items are included in the same product name C2o, a temporary alias E3o may be suggested to the user by adding a serial number after the product name C2o such as "coffee 1", "coffee 2", "coffee at store A", or "coffee at store B", or by combining the product name C2o with the store name R1o, or the brand name E2o, or multiple candidates may be presented on the screen, and the user may be allowed to select the desired item at the time of calling. When registering a new item such as at the time of acquisition, the user may directly enter the field as described above in the input box for each field on the screen of the information terminal 300, or the user may enter the field by using a sentence such as "On new registration . . . the brand name is . . . the product name is . . . the alias is . . . ".

A supplementary explanation of FIG. 5 is as follows. A of FIG. 5 is an example of purchase input, showing that the sentence "What I bought at store A today was ham of brand B 280 yen and cheese 500 yen and baguette 340 yen", is entered by the user to the information terminal 300. B of FIG. 5 is an example of the corresponding recognition result by the inspection unit 102. According to a prior agreement, the intention R6o of "purchase input" is recognized from "What I bought" in the sentence, the date February 16th is recognized from the time stamp at the time of input for "today", and "store A" is recognized as the store name R2s after confirming the match with the existing store name R2o. Prior to extracting the nickname I3t, "and" is used to efficiently extract the nickname I3t and improve recognition accuracy by separating the character string and distinguishing the articles. "ham", "cheese" and "baguette" are recognized as nicknames I3t, respectively, and the numerical value after each nickname I3t is recognized as the purchase price P1t of the article. For "brand B", in the case of purchase input, if there is "of" after the nickname I3t, assuming that there is an agreement that the character string immediately after "of" is recognized as the brand, in this example "brand B" is recognized as the brand E2t according to a prior agreement. Or, without using "of" or the like, the character string just after the nickname I3t may be simply recognized as the brand E2t. Although it is necessary to input the nickname I3t, or the product name instead of the nickname I3t, the input of the brand E2t is not essential. C of FIG. 5 is an example of the storage input, and D of FIG. 5 is an example of the corresponding recognition result by the inspection unit 102. When the sentence "In the refrigerator keep ham until February 20th and cheese until March 5th" is input, the intention R6o of the "storage input" is first recognized from the character string "keep" according to a prior agreement. Next, the storage spot L4s of "refrigerator" is recognized as a character string related to the location before the character string "keep", according to a prior agreement. Then, in the same way as in B of FIG. 5, character strings related to articles are distinguished by "and", nicknames "ham" and "cheese" are recognized, and the dates after each nickname, "February 20th" and "March 5th", are recognized as the target consumption deadlines T5o corresponding to each nickname, assuming that such agreements have been made in advance. Similarly, when the sentence "On the shelf keep baguette for 2 days" is input, the character string "keep" is recognized as the intention R6o of "storage input", the storage spot L4s "shelf" is recognized, the nickname "baguette" is recognized, and from the character string "for 2 days" representing the date, and the time stamp of 2/16, 2/18 which are two days after the time stamp at the time of input, are recognized.

A supplementary explanation of FIG. 7 is as follows. When the user inputs the sentence "Inventory check J bagel" on the input screen of the information terminal 300, assuming that such an agreement has been made in advance, by the character string "Inventory check", the intention R6o for confirmation of inventory is recognized, and since "J bagel" matches the existing nickname A3i, data is extracted according to conditions such as absence of the finished flag F2n based on the record in the food material table T-2. In this example, details such as the acquisition date T4v and the spot L4e are displayed on the output screen of the information terminal 300. In this case, an article item with the product name C2s, "bagel", whose brand E2o is company J, is given the alias E3o, "J bagel". In this figure, the data of the inventory list query Q-7 also includes the fields of the alias E3o and the price P1o.

A supplementary explanation of FIG. 8 is as follows. FIG. 8 shows an example of the screen when multiple inputs are made to the information terminal 300 by the user on Dec. 11, 2019, and the recorded contents of the database 110. The fields of the table in this example are excerpts, including fields related to the consumer L1s and the date and time T1t based on the consumption date and time table T-3. Assuming that two persons "I, Child 1" are set as the basic setting for the subject consumer L1o in the consumer table M-8 by pre-registration by the user, if there is no designation of the consumer L1o when the meal content is input, the same meal content is recorded for "I" and "child 1" according to a prior agreement. In this example, the user himself or herself is referred to as "I" and the child of the user is provisionally referred to as "child 1", however, an arbitrary name can be set for the consumer L1o, or if there is no setting, the user himself/herself is treated as the consumer L1s. In the sentence input at 10:25, the data is recorded in the food material record report R-1 as a consumption of the article items corresponding to each of the nicknames I1t by the two consumers L1s of "I, child 1". In the examples, "At 11:00 child 1 had a stomach condition level 2.5" entered at 11:50, "child 1 had a stomach condition level 0.5" entered at 12:00, "At 14:00, I had a meal outside at restaurant A and ate curry rice and the content was potatoes and carrots and beef and onions and rice and lettuce also at 15:00 level 1" entered at 15:15, and "At 16:00 I had level 1.5" entered at 17:03, according to a prior agreement, the sentence containing the character string "level" is treated to have the intention R6o of recording the physical condition event, and the number immediately after the character string "level" is treated as the number of the field of level E1o and recorded in the level table T-4. Furthermore, in this example, if there is a physical condition feature R4o registered in the physical condition table M-9 immediately before the character string "level", it is to be recorded as a physical condition feature R4s. Assuming that "stomach condition" is registered as the physical condition feature R4o, "stomach condition" is recorded as the physical condition feature R4s for the inputs at 11:50 and 12:00. In this example, "level" is treated as the intention R6o, but "stomach condition" can also be treated as a kind of the intention R6o as well as the physical condition feature R4s. In this case, only "level" without the physical condition feature R4s is an example of the basic setting of "itchiness" according to a prior agreement. Further, in this example, if there is a specification of consumer L1o at the beginning of a sentence, data regarding "I" and "Child 1" are distinguished and recorded for those with the specification, assuming that there is a prior agreement to record for the specified consumer L1o. Since the sentence entered at 15:15 contains the intention R6o of eating out, "meal outside", "At 15:00 level 1" including the trailing "level" and the earlier part are treated separately as parts related to the different intention R6o. A character string such as "also" immediately preceding that may be treated as a character string that divides a sentence into intentions according to a prior agreement, as a system for efficiently dividing a sentence according to intentions, or it may not be recognized. Thus, not all character strings in the input sentence are recognized. Regarding the part related to the intention R6o of eating out, the eating out table T-5 is updated for "restaurant A" of the store R3o, "curry rice" of the menu E4o, "potato and carrots and beef and onions and rice and lettuce" of the content D6o, and the like.

A supplementary explanation of FIG. 9 is as follows. A is an example of a screen where the sentence "shopping plan has been updated" is output after the sentence "shopping plan at store A for soy sauce and miso and green onions" is input. B shows that the sentence input in A is recorded in the database 110 through the following processing. The intention R6o of the "shopping plan" is recognized from the character string "shopping plan" in the input sentence in accordance with a prior agreement, the character string "store A" after "at" is confirmed to match the existing store name R1o, assuming that such a prior agreement has been made, and the corresponding data is extracted from the food material table T-2 based on the store name R1o. The character string after that relating to subsequent articles is distinguished by "and". As a result, "soy sauce", "miso", and "green onions" are recognized as nicknames, respectively, and made to correspond to the nicknames A3i in the nickname query Q-1, and the flag F3y of the "shopping plan" is set in the data of the corresponding food material table T-2. While A and B are examples based on the premise that the food material table T-2 already has data, it is possible to newly add the articles that have not been purchased in the past to the food material table T-2 as "shopping plan". C is an example of a plan check, and when the sentence "Check the shopping plan for store A" is input, the sentence "This is the shopping plan at store A" and an extracted article list is output. Assuming that such a prior agreement has been made, the intention R6o of the "shopping plan check" is recognized from the combination of the character strings "shopping plan" and "check", and is made to correspond to the shopping query Q-6. Further, in a case where "at" follows the "shopping plan", it is assumed that such a prior agreement is made for the following "store A", matching with the existing store R1o is confirmed, and data is extracted from the shopping query Q-6 for the store R1e. The list of articles to be output is an example of articles with the product name C2v and the brand E2v being displayed for articles purchased at "store A" among articles with the flag F3y of "purchase plan", including the above articles updated in A and B.

A supplementary explanation of FIG. 10 is as follows. A is an example of conversion value calculation subjects among levels in a day where a plurality of physical condition events of the same type are input within a single day on December 12th. In the case of irregular recordings like this, in order to quantify the physical condition as a physical condition level value in chronological order, the data subject to conversion value calculation is extracted. Specifically, in descending order of absolute value, the level 4 physical condition events at 14:10 are extracted first and then the level 3 physical condition events are extracted, but level 3 at 15:05 is excluded because the interval with level 4 at 14:10 is less than 1 hour, and only the 13:00 physical condition events at level 3 are extracted. Next, level 2 at 18:20 and level 1 at 21:15 are extracted as subjects in this order. As described above, when extracting a physical condition event to be a subject, the interval between the event and a physical condition event already extracted must be at least one hour. Similar to the above, the physical condition events at Level 2 at 13:20 and Level 1 at 18:40 are not included in the conversion calculation because the time difference between them is less than 1 hour. In the calculation example of the conversion values A2i from the levels E1o in B, it is shown that the conversion values A2i are 12.8 for level 4, 5.4 for level 3, 1.6 for level 2, and 0.2 for level 1, respectively for the four subject physical condition events in A. In the example in C of the calculation result of the daily conversion value A2i, the total conversion value on December 12th is calculated as 20.0. Also it is shown that the same calculation is performed and the conversion values A2i are aggregated daily from December 9th to 13th.

Supplementary explanations of FIGS. 13 and 14 are as follows. FIG. 13 shows that on Nov. 25, 2019, after the user input "Display reactions within 6 hours after eating mackerel" into the information terminal 300, actual consumption records with the keyword "mackerel" at 13:00 on Jun. 17, 2019, 12:30 on Aug. 8, 2019, and 19:00 on Nov. 23, 2019 are extracted at first, then the records of physical condition events within 6 hours from those dates and times are extracted from the past data of the food material and level report R-2. As an example, level 0.9 at 14:00 and level 2.4 at 15:00 within 6 hours after the consumption of "mackerel" at 13:00 on Jun. 17, 2019 are extracted. Thus, when specifying the time for checking the reaction each time, the physical condition event can be extracted regardless of the set observation time. FIG. 14A shows an example of confirming the possibility of the causes from the physical condition, where the user enters "Display advice about the itch entered earlier" into the information terminal 300, and assuming that the user had a record of a physical condition event related to "itchiness" at 16:00, prior to 19:00 at the time of input. The output was "There is a possibility that the itchiness at 16:00 today was related to 'brand A vegetable juice' consumed at 12:00, followed by 'milk', then 'wheat". Assuming that there is a 6 hours observation time, there was a meal record at 12:00 which is 4 hours before the physical condition event at 16:00, and among the article items such as food contained in the record, "brand A vegetable juice", "milk", and "wheat" are shown in descending order of the latest scores A6i of the score report R-5 in this example. These may be sentences including the nickname A3i as in this example, or may allow the user to identify the article items by combining the product name C2s and the store name R1v or the brand name E2v in a tabular form. B of FIG. 14 shows an example of checking the physical condition from an article in the opposite direction. When the user inputs a sentence "I want to know the result of drinking vegetable juice" to the information terminal 300 on January 5th, the output sentence "Level 1.2 at 1 hour and level 2 at 2 hours after consuming "brand A vegetable juice" at 8:00 on November 15th, level 2 at 2 hours after consuming "brand A vegetable juice" at 13:00 on December 5th, and no reaction within 6 hours of consuming "brand B vegetable juice" at 10:00 on December 20th", is shown. In this example, it is assumed that the database 110 is searched using the product name C2w of "vegetable juice", but it is also possible to perform a more narrowed-down search using the nickname A3i. Although this example is similar to the example of FIG. 13, since no time is specified, the observation time is assumed to be 6 hours, indicating information about the physical condition events within 6 hours after "vegetable juice" was consumed in the past. In this case, the product name "vegetable juice" includes "brand A" and "brand B" articles, which are shown separately. In the example of A of FIG. 14, if the user suspects that "vegetable juice" is the cause of poor physical condition, the user can check the details as shown in B of FIG. 14. In addition, it is possible to grasp the differences in physical condition after consumption of "brand A" and "brand B". In the case of these examples, it is assumed that processing methods corresponding to the input contents are determined in advance.

A supplementary explanation of FIG. 15 is as follows. A of FIG. 15 is an example of an input content by the user to the information terminal 300. If the sentence “Keep items purchased at store A in the storage white porridge 5 packs by next February with an interval of 2 weeks and natural water 3 bottles by May 2022 and rice cakes 2 bags by October with an interval of 1 month”, is input, B of FIG. 15 shows an example of the recognition result by the inspection unit 102 as follows. Assuming that such a prior agreement has been made, the intention R6o of “storage input” is first recognized by “keep” in the sentence, and the storage spot L4s is recognized by the following “in the storage”. Furthermore, “store A” after “purchased at” is recognized as the store name R1o after confirming a match with an existing store name. The character strings after “in the storage” are divided by “and” to distinguish the contents regarding the articles. As for “white porridge”, “natural water”, and “rice cakes”, they are matched with the existing nicknames A3i, and the data are extracted from the food material table T-2. If they cannot be matched with the existing nicknames A3i, they may be temporarily recorded as new articles. The “5 pieces”, “3 bottles”, and “2 bags” after each nickname are recognized as the number of each article. The subsequent “by next February”, “by May 2022”, and “by October” are recognized as the target consumption deadline T5o of each article. The subsequent “interval of two weeks” and “interval of one month” for “white porridge” and “rice cakes” are recognized as the shortest allowable consumption intervals T6o.

A supplementary explanation of FIG. 16 is as follows. As an example, when the user inputs “Check for coming expiration dates” to the information terminal 300, if the sentence is input according to a prior agreement, assuming that the target consumption deadline T5o or the recommended consumption deadline T7i, whichever comes first, is to be extracted for example, two days, “The items due today are cabbage, baguette, and white porridge. The items due tomorrow are chicken and radish”, is output. Such an output content may be the target consumption deadlines T5o by a prior agreement, or may be combined with the recommended consumption deadlines T7i as in this example. Next, when the sentence “Check for storage spot of white porridge” is entered, assuming that there is a prior agreement to extract the storage spot L4v and the quantity Q1i, based on the character string “Check for storage spot” for the article items corresponding to the nicknames included in the following character string, the data of the stockpile detail query Q-8 and the stockpile quantity query Q-9 is extracted based on the name “white porridge”, and “There are 10 packs of white porridge in the storage”, is output. In this manner, the user can immediately check the expiration date and storage location of the article, so that the stored articles can be utilized without waste. In this example, it is assumed that the total quantity Q1i in the stockpile quantity queries Q-9 is automatically calculated from the food material table T-2. However, if a field for the number of articles is provided in the food material table T-2 as necessary, the articles can be managed in more detail. The user can also correct the inventory quantities in the database 110 to accurate inventory quantities by entering quantities of article items by the location L3s, the spot L4s and the like with a sentence utilizing nicknames, such as “In an inventory check, there are 8 packs of white porridge in the storage”.

A supplementary explanation of FIG. 17 is as follows. As an example of checking consumption in A, in the information terminal 300 used by the user, the question “Did you take vitamins today?” is output at 21:00 by the life information system 1, and if the answer “I took vitamins three times today” is entered by the user at 21:30, the comment “Then, it’s okay”, is output at 21:30. A prior agreement may be made with the user in advance if the number of times is not entered, such as “vitamin at 9:00”, will be recognized as one tablet each time. As an example of consumption advice in B, if the question “Have you opened a pack of cigarettes recently?” is output to the information terminal 300 used by the user at 20:00, and the user inputs the answer, “At 15:00 I opened a pack” at 20:30, the comment, “Since the last time you opened a pack, you have consumed 6 cigarettes per day, with an interval of 8o hours. This time the pace has increased a little. Let’s reduce that number a little more.”, is output at 20:30. This is an example in which the question is displayed because the user did not input a sentence such as “At 15:00 I opened a pack” at the expected timing. Assuming that this user’s goal is to quit smoking, after making such a prior arrangement, by a method such as the comparison of the user’s performance in the interval between the consumption of a pack of cigarettes between the most recent one and the average of the most recent period, it is possible to vary the advice as to whether the user’s consumption record is good, or requires a little more effort.

The explanation of FIG. 19 is as follows. FIG. 19 illustrates an example of observation times and analysis target group ranges where the physical condition events to be converted are in the case of A of FIG. 10 and the consumption events of the articles are in the case of E of FIG. 11 along the time flow 500. An analysis target group is a collection of lifestyle habit events that occurred during the observation time in order to clarify the cause of the state of the physical condition event, and the target range can be divided within the observation time according to the physical condition events. A physical condition event a 511, physical condition event b 512, physical condition event c 513, and physical condition event d 514 respectively indicate the four physical condition events subject to conversion value calculation in A of FIG. 10. A lifestyle habit event a 521, lifestyle habit event b 522, and lifestyle habit event c 523 respectively indicate three consumption events of articles, which are lifestyle habit events shown in E of FIG. 11. An observation time a 531, observation time b 532, observation time c 533, and observation time d 534 are all the same as 6 hours and correspond to a physical condition event a 511, physical condition event b 512, physical condition event c 513, and physical condition event d 514 respectively, which are immediately after each corresponding observation time. An analysis target group range a 541, analysis target group range b 542, analysis target group range c 543, and analysis target group range d 544 correspond to the physical condition events immediately after the analysis target group ranges, and are the same as the observation time or within ranges shorter than the observation time in relation to other physical condition events. As an example, in the case of the physical condition event a 511 at 13:00 and the physical condition event b 512 at 14:10 in A of FIG. 10, assuming that the observation time is 6 hours, the observation time a 531 and the observation time b 532 are after 7:00 and after 8:10, respectively, but since the physical condition event b 512 of level 4 at 14:10 is a higher level than the physical condition event a 511 of level 3 at 13:00, the groups of consumed article items subject to 100% proportional calculation are divided into two groups of article items, of which one group is from 7:00 to 8:10 shown in the analysis target group range a 541 and the other is from 8:10 to 14:10 shown in the analysis target group range b 542. The lifestyle habit event b 522 falls within the analysis target group range b 542, and the article items consumed in the lifestyle habit event b 522 are the targets of the prorated calculation of 100% as shown in FIG. 11E, but if there are any lifestyle habit events other than that shown in the drawing within the range b 542 of the analysis target group, the article items at that time are also the targets of the prorated calculation of 100% together with the article items consumed in the lifestyle habit event b 522. In this example, since the lifestyle habit event b 522 occurs during the observation time a 531 which is the observation time of the physical condition event a 511 and during the observation time b 532 which is the observation time of the physical condition event b 512, it is suspected to be a cause of both physical condition events, and the scores for the article item are calculated for both physical condition events as in G of FIG. 12. The lifestyle habit events to be included in the analysis target group can be made to correspond to the physical condition feature R4o, for example, by providing a flag corresponding to the physical condition feature R4o in accordance with the class C1o of the article item or at the time of registration of the article item by the user. For example, for a group to be analyzed for physical condition events related to scalp condition, lifestyle habit events related to scalp condition can be extracted by flags and included. Even if the same article item is consumed multiple times in the analysis target group, 100% prorated % is added to the same article item only once.

The explanation of FIG. 20 is as follows. As an example, at 15:00 on March 14th, when the user inputs "At 13:00 the menu was meatballs and the ingredients were minced pork and onions and breadcrumbs" on the information terminal 300, the input date and time T1t and the menu name E5s are first recorded in the consumption date and time table T-3. If the menu name E5o "meatballs" is not registered in the menu table T-1 prior to that, it is newly registered and the menu table T-1 is updated. In this case, a rule of recording is agreed in advance that the character string between "menu was" and "and" is treated as the menu name E5s, and the nicknames following the character string "ingredients were" are recorded to the nicknames I1t in the food material input table T-6. As a result of the processing, the date and time T1o of the event, the menu name E5c, and the nicknames A3c are associated and recorded in the food material record report R-1. After such a record is made, for example, at 19:30 on April 5th, if an input of "at 19:00 meatballs" is entered, it is possible to extract the combination of the menu name E5c and the nicknames A3c related to the "meatballs" in the latest food material record report R-1 on March 14th, and record the same ingredients as the most recently consumed menu. Also, for example, if on April 20th the user inputs "Search previous menus using minced pork", assuming that there is a prior agreement in advance for the case if "search previous menus" is input, to search the latest menu E5c using the following nicknames, any menu E5c associated with "minced pork" in addition to "meatballs", such as "dumplings" and the like that has been recorded in the past, is extracted from the food material record report R-1, and the information "The menus for minced pork include meatballs, dumplings and croquettes" is output after the input. Conversely, if on May 11 the user inputs "Search for ingredients of meatballs", assuming that there has been a prior agreement in advance for the case if "search for ingredients of" is input, to treat the following character string as a menu name, nicknames of food materials in association with the menu name are extracted, and based on the latest consumption record on April 5, "The ingredients of meatballs are minced pork, onions and breadcrumbs" is output. The above-described method of searching for menus from ingredients can be used to search for menus in the knowledge base in addition to searching for the user's past menu records. Also, based on the settings in advance, it is possible to propose menus for ingredients whose target consumption deadline T5o and recommended consumption deadline T7i are approaching.

The explanation of FIG. 21 is as follows. In this example, based on the input content "At 19:00, 1 egg and 150 grams of pork and . . . " and the information in the inclusion conversion table M-10 that the protein inclusion amount Q5o per egg is 7 grams and the protein inclusion amount Q5o per 100 grams of pork is 2o grams, one egg and 150 grams of pork recorded in the food material record report R-1 are calculated as inclusions E6o of 7 grams and 3o grams of protein respectively. The information is added to the current memo M2o in the food material record report R-1. In this example, assuming that the total amount of the inclusions E6o is to be output each time, the information "Total protein for this time is 37 grams" is displayed on the information terminal 300 used by the user. Such information on the inclusion amount Q5o for the user may be collected and notified periodically such as daily, or it may be presented in the form of a graph.

The present invention also includes the following features.

[1]

An information processing system for providing advice by comparing lifestyle habit and physical condition comprising:

an acquisition unit that receives data of a lifestyle habit event that is an event relating to a state of the lifestyle habit and a physical condition event that is an event related to a state of the physical condition including occurrence date and time information of each event occurring from time to time on the basis of an input by a user;

an updating unit that updates a database based on the acquired data:

an analysis unit that extracts, with respect to data of individual physical condition events, the lifestyle habit events that occurred within an observation time on the basis of the occurrence time of the physical condition events, includes the lifestyle habit items corresponding to the lifestyle habit events in an analysis target group for analyzing the causes of the physical condition events, updates possibility degree values corresponding to the lifestyle habit items included in the analysis target group from the most recent possibility degree values based on past analysis results for the lifestyle habit items included in the analysis target group, and extracts the lifestyle habit items that may cause the physical condition from the database based on the results;

and a notification unit that transmits advice based on analysis results obtained by the analysis unit to an information terminal used by the user, wherein:

the lifestyle habit item is a type of lifestyle habit, and the data of lifestyle habit events includes information on lifestyle habit items, the possibility degree value is a numerical value indicating a degree of possibility that the lifestyle habit item is a cause of a physical condition event, and the observation time is a time set for observing occurrences of a physical condition event after a lifestyle habit event.

[2]

The information processing system according to [1], wherein the analysis unit obtains a physical condition level value which is a value digitized in time series so as to represent a transition of the degree of good or poor physical condition based on the data of the physical condition events.

[3]

The information processing system according to [2], wherein the analysis unit extracts the lifestyle habit items that may cause the physical condition from the database by determining a score representing the magnitude of the effect of each of the lifestyle habit items in the analysis target group at the time of the physical condition event on the physical condition, using the physical condition level value at the time of the physical condition event and the latest possibility degree value for the respective lifestyle habit item in the analysis target group corresponding to the lifestyle habit events extracted as analysis targets within the observation time.

[4]

The information processing system according to [3], wherein the analysis unit determines the latest score by obtaining statistics of the past score for each lifestyle habit item, and extracts the lifestyle habit items that may cause the physical condition from the database.

[5]

The information processing system according to any one of [1] to [4], wherein, when the user inputs a character string related to a specific lifestyle habit event for the lifestyle habit events in the past, the notification unit extracts data of the lifestyle habit events including the input character string, further extracts data of the physical condition events within a predetermined time specified by the user after the occurrence of the extracted lifestyle habit events, and transmits the data to an information terminal used by the user.

[6]

The information processing system according to any one of [1] to [5], wherein the analysis unit refers to the information of other consumers accumulated in the knowledge base, and analyzes the correlation between data on lifestyle events and data on physical condition events based on the input by the user, and the notification unit transmits to an information terminal used by the user, on the basis of an analysis result by the analysis unit, information about the lifestyle habit items that may affect the physical condition of the user, or prediction timings at which the physical condition will be affected after the lifestyle habit events of the user relating to the specific lifestyle habit items.

[7]

The information processing system according to any one of [1] to [6], wherein the data of the physical condition event input by the user is based on an arbitrary numerical value input by the user each time to represent the state of the physical condition.

[8]

The information processing system according to any one of [1] to [7], wherein the observation time is adjusted according to the state of the physical condition for each user.

[9]

The information processing system according to any one of [1] to [8], wherein, the analysis unit divides the observation time according to the state of the occurrences of a plurality of the physical condition events when a plurality of physical condition events occur within the observation time, extracts the lifestyle habit events that occurred within the respective divided observation times, and includes the lifestyle habit items corresponding to the lifestyle habit events in the separate analysis target groups for the respective physical condition events.

[10]

The information processing system according to any one of [1] to [9], wherein with the rule that the same kind of physical condition event is counted only once within a certain time period, the analysis unit determines the physical condition event to be an analysis target by giving priority to a physical condition event of higher level when multiple physical condition events are recorded within a certain time period, extracts the lifestyle habit events that occurred within the observation time with reference to occurrences of the physical condition event, and includes the lifestyle habit items corresponding to the lifestyle habit events in the analysis target group for analyzing the cause of the physical condition event.

[11]

The information processing system according to any one of [1] to [10], wherein the lifestyle habit is a consumption of an article.

[12]

The information processing system according to [11], wherein the article is either a raw material itself, or an article made from the same raw material which is treated as an article of the same lifestyle habit item.

[13]

The information processing system according to [11], wherein the article is a meal content when the user uses a restaurant or a ready-made food, and the analysis unit treats the user's meal content as the lifestyle habit item when the user inputs the meal content including at least one of the store name and the menu name.

[14]

The information processing system according to any one of [1] to [13], wherein the lifestyle habit items are registered by the user using arbitrary character strings.

[15]

The information processing system according to any one of [2] to [14], wherein the notification unit transmits data to an information terminal used by the user, based on a prior setting, for displaying the periodically aggregated physical condition level values as a graph representing a long-term trend in the physical condition of the user.

[16]

The information processing system according to any one of [1] to [15], wherein the user registers physical condition features in advance, and the analysis unit distinguishes data relating to features of the physical condition events that is input together with the physical condition features registered by the user, and extracts the lifestyle habit items that may cause the physical condition from the database.

[17]

The information processing system according to [16], wherein the physical condition features are registered by the user using arbitrary character strings.

[18]

The information processing system according to any one of to [17], wherein, after identifying substances to be managed based on the user's request in advance, the analysis unit determines the amount of a specific substance contained in the article consumed by the user from the description of the amount of the article input by the user and the information accumulated in the knowledge base, and also analyzes the correlation between the intake status of the specific substance and the physical condition events, and the notification unit transmits the analysis results obtained by the analysis unit to an information terminal used by the user.

[19]

The information processing system according to any one of [1] to [18], wherein the analysis unit compares data of the lifestyle habit events based on an input of a user with a target related to the lifestyle habit based on a prior setting, and the notification unit transmits advice based on the analysis results obtained by the analysis unit to an information terminal used by the user.

[20]

An information terminal for providing advice by comparing lifestyle habit and physical condition comprising:

an acquisition unit that receives data of a lifestyle habit event that is an event relating to a state of the lifestyle habit and a physical condition event that is an event related to a state of the physical condition, including occurrence date and time information of each event occurring from time to time on the basis of an input by a user;

an updating unit that updates a database based on the acquired data;

an analysis unit that extracts, with respect to data of individual physical condition events, the lifestyle habit events that occurred within an observation time on the basis of the occurrence time of the physical condition events, includes the lifestyle habit items corresponding to the lifestyle habit events in an analysis target group for analyzing the causes of the physical condition events, updates possibility degree values corresponding to the lifestyle habit items included in the analysis target group from the most recent possibility degree values based on past analysis results for the lifestyle habit items included in the analysis target group, and extracts the lifestyle habit items that may cause the physical condition from the database based on the results; and a notification unit that notifies advice to the user based on analysis results by the analysis unit, wherein:

the lifestyle habit item is a type of lifestyle habit, and the data of lifestyle habit events includes information on lifestyle habit items, the possibility degree value is a numerical value indicating a degree of possibility that the lifestyle habit item is a cause of a physical condition event, and the observation time is a time set for observing occurrences of a physical condition event after a lifestyle habit event.

[21]

A computer-readable recording medium storing a program for providing advice by comparing lifestyle habit and physical condition, which executes the steps of:

receiving data of a lifestyle habit event that is an event relating to a state of the lifestyle habit and a physical condition event that is an event related to a state of the physical condition, including occurrence date and time information of each event occurring from time to time on the basis of an input by a user, updating a database based on the acquired data, and extracting lifestyle habit items that are likely to be the cause of a physical condition from a database based on the results, and with respect to data of individual physical condition events, said program extracts the lifestyle habit events that occurred within an observation time on the basis of the occurrence time of the physical condition events, includes the lifestyle habit items corresponding to the lifestyle habit events in an analysis target group for analyzing the causes of the physical condition events, and updates possibility degree values corresponding to the lifestyle habit items included in the analysis target group from the most recent possibility degree values based on past analysis results for the lifestyle habit items included in the analysis target group, wherein:

the lifestyle habit item is a type of lifestyle habit, and the data of lifestyle habit events includes information on lifestyle habit items, the possibility degree value is a numerical value indicating a degree of possibility that the lifestyle habit item is a cause of a physical condition event, and the observation time is a time set for observing occurrences of a physical condition event after a lifestyle habit event.

The present invention also includes the following features.

[1]

An information terminal for managing information on articles comprising:

an acquisition unit that receives a sentence related to articles input according to rules defined for each user;

an inspection unit that identifies the user's intention by recognizing predetermined character string in the sentence for directing an action to a database, and extracts nicknames of the articles from the remaining character strings;

an updating unit that selects, based on the identified user's intention, a table of a type corresponding to the user's intention from tables of types containing user-specific data in the database, extracts data on one or a plurality of user-specific articles by associating nicknames of one or a plurality of articles extracted from the sentence with nicknames of the one or plurality of articles registered for each user in the selected table, and collectively updates the database; and a notification unit that notifies the user, wherein:

the rules defined for each user are that the user specifies character strings representing intentions for directing actions to the database in advance, and registers nicknames, which are keywords for specifying articles in the database in advance, and at least an acquisition record and a consumption record of articles are included in the types of user's intentions.

[2]

An information processing system for managing information on articles comprising:

an acquisition unit that receives a sentence related to articles input according to rules defined for each user;

an inspection unit that identifies the user's intention by recognizing predetermined character string in the sentence for directing an action to a database, and extracts nicknames of the articles from the remaining character strings;

an updating unit that selects, based on the identified user's intention, a table of a type corresponding to the user's intention from tables of types containing user-specific data in the database, extracts data on one or a plurality of user-specific articles by associating nicknames of one or a plurality of articles extracted from the sentence with nicknames of the one or plurality of articles registered for each user in the selected table, and collectively updates the database; and a notification unit that transmits a notification to an information terminal used by the user, wherein:

the rules defined for each user are that the user specifies character strings representing intentions for directing actions to the database in advance, and registers nicknames, which are keywords for specifying articles in the database in advance, and at least an acquisition record and a consumption record of articles are included in the types of user's intentions.

[3]

The information processing system according to [2], wherein the inspection unit extracts the nicknames of a plurality of articles by dividing the sentence by predetermined words or symbols, and the rule defined for each user is that the user specifies words or symbols for dividing sentences in advance, and registers the words or symbols in the database.

[4]

The information processing system according to [2] or [3], wherein:

by recognizing the character strings representing fields of information about the article entered after the nickname of the article in the sentence, the inspection unit extracts following contents of the fields, and the updating unit records the contents of the fields related to the article corresponding to the nickname.

[5]

The information processing system according to any one of [2] to [4], wherein:

the inspection unit searches for a plurality of character strings representing the intentions of the user from the sentence, extracts character strings dependent on each intention from each of the character strings before and after the plurality of character strings representing the intentions and separates the sentence according to each intention, and the updating unit makes each of the divided sentences correspond with a table of a type corresponding to the intentions in the database respectively, according to a rule defined in advance for each user.

[6]

The information processing system according to any one of [2] to [5], wherein:

the inspection unit converts character strings representing dates after nicknames of articles in a sentence input for purchase record or inventory check of articles into date data, the updating unit records the converted date data as target consumption deadlines in corresponding tables in the database, and the notification unit, in response to a request from an information terminal used by a user, transmits information for displaying a list of target consumption deadline order of the articles to the information terminal used by the user.

[7]

The information processing system according to [6], wherein:

when the user owns a plurality of articles of the same article item, the notification unit calculates a recommended consumption deadline for each article from a shortest allowable consumption interval, which is an interval at which the user can consume the article item, and a target consumption deadline for each article of the article item, and in response to a request from an information terminal used by the user, transmits information for displaying the recommended consumption deadline to the information terminal used by the user.

[8]

The information processing system according to any one of [2] to [7], wherein, in response to a request from an information terminal used by the user, the updating unit records the data of the article for each spot and for each class, and the notification unit transmits information for displaying an inventory list of articles by spot or class to the information terminal used by the user.

[9]

The information processing system according to any one of [2] to [8], wherein, in response to a request from an information terminal used by the user, the updating unit records data of an article for each store or brand, and sets a flag to the article data indicating that the user is planning to purchase the articles, the notification unit transmits information to the information terminal used by the user to display articles that the user is planning to purchase according to store or brand, the analysis unit refers to information about the articles accumulated in the knowledge base, according to the inventory status of the articles recorded in the database, and the notification unit transmits information about recommended articles to the information terminal used by the user.

[10]

The information processing system according to any one of [2] to [9], wherein:

the updating unit, based on an input by the user, can associate a menu with article data, and when a menu name is input instead of the nickname of an article by the user, data of a plurality of articles associated with the menu can be collectively updated, and the notification unit, in response to a request from an information terminal used by the user, searches a menu from nicknames of associated articles, or searches for associated articles from a menu name, and transmits the search result to the information terminal used by the user.

[11]

The information processing system according to any one of [2] to [5] or [8], comprising:

an analysis unit that first specifies a substance to be managed based on a user's request, that calculates an amount of the substance included in an article consumed by the user from a description regarding the amount of the article input by the user, and analyzes a correlation between the intake amount of the specific substance and the physical condition, and the notification unit transmits the analysis result to an information terminal used by the user.

[12]

The information processing system according to any one of [2] to [8], wherein:

the inspection unit, if there is a character string representing date and time before the character string representing the intention in the sentence input by the user, converts the character string into date and time data, the updating unit records the converted date and time data in the corresponding table of the database as the occurrence date and time of the actual user's life event, instead of the input time of the sentence, in accordance with the intention of the user, and the notification unit, in response to a request from the information terminal used by the user, transmits the extracted data of the user's life event for display on the information terminal used by the user.

[13]

An information terminal according to [1] for providing advice about consumption of an article to a user wherein, when character strings representing a nickname and a consumption quantity of an article consumed by the user are input to the information terminal, a comparison result with respect to a consumption target is output.

[14]

A computer-readable recording medium in which a program for managing information on articles is stored, which executes the steps of:

receiving a sentence related to articles input according to rules defined for each user;

identifying the user's intention by recognizing predetermined character string in the sentence for directing an action to a database, and extracting nicknames of the articles from the remaining character strings;

selecting a table of a type corresponding to the user's intention from tables of types containing user-specific data in the database based on the identified user's intention, and extracting data on one or a plurality of user-specific articles by associating nicknames of one or a plurality of articles extracted from the sentence with nicknames of the one or plurality of articles registered for each user in the selected table, and collectively updating the database, wherein:

the rules defined for each user are that the user specifies character strings representing intentions for directing actions to the database in advance, and registers nicknames, which are keywords for specifying articles in the database in advance, and at least an acquisition record and a consumption record of articles are included in the types of user's intentions.

REFERENCE SIGNS LIST

1 Life information system
100 Server
101 Acquisition unit
102 Inspection unit
103 Updating unit
104 Analysis unit
105 Notification unit
110 Database
111 Knowledge base
200 Communication network
300 Information terminal
301 Computer
302 Smartphone
303 Smart speaker
410 Processor
420 Memory
430 Storage device
440 Communication device
450 Bus
461 Input device
462 Output device
500 Time flow
511 Physical condition event a
512 Physical condition event b
513 Physical condition event c
514 Physical condition event d
521 Lifestyle habit event a
522 Lifestyle habit event b
523 Lifestyle habit event c
531 Observation time a
532 Observation time b
533 Observation time c
534 Observation time d
541 Analysis target group range a
542 Analysis target group range b
543 Analysis target group range c
544 Analysis target group range d

The invention claimed is:

1. An information processing system comprising:

a memory; and a processor in communication with the memory configured to:

receive a sentence related to an article input according to rules defined for a user;

identify an intention of the user by recognizing a predetermined character string of a plurality of predetermined character strings in the sentence for directing an action to a database;

extract a nickname of the article by recognizing a predetermined character string of a plurality of predetermined character strings from remaining character string in the sentence;

select, based on the identified intention of the user, a table of a type corresponding to the intention of the user from a plurality of tables of types;

extract data on a user-specific article by associating the nickname of the article extracted from the sentence with the nickname of the article registered for the user in the selected table; and collectively update the database, wherein:

the rules defined for the user comprise (i) registering a user-specific character string representing the intention of the user for directing an action to the database in advance, (ii) registering the nickname, the nickname comprising a keyword for the user-specific article in the database in advance, and (iii) types of intention of the user including an acquisition record or a consumption record of articles, and wherein the processor is further configured to receive data of a lifestyle habit event comprising an event relating to a state of the lifestyle habit, and a physical condition event comprising an event related to a state of the physical condition including occurrence date and time information of each event on a basis of an input by a user to an information terminal accessible by the user;

update a database based on the received data;

extract, with respect to the data of the physical condition event, the lifestyle habit event that occurred within an observation time on a basis of the occurrence time of the physical condition event;

associate a lifestyle habit item corresponding to the lifestyle habit event in an analysis target group for analyzing a cause of the physical condition event;

update a possibility degree value corresponding to the lifestyle habit item in the analysis target group from a most recent possibility degree value based on a past analysis result for the lifestyle habit item in the analysis target group;

extract the lifestyle habit item being the most probable cause of the physical condition from the database based on the result; and send advice to the information terminal accessible by the user, wherein:

the lifestyle habit item comprises a type of the lifestyle habit, the data of the lifestyle habit event includes information on the lifestyle habit item, the possibility degree value comprises a numerical value indicating a degree of possibility that the lifestyle habit item is a cause of the physical condition event, the observation time comprises a time set for observing occurrences of the physical condition event after the lifestyle habit event, the occurrence date and time information is entered as a timestamp representing input date and time by a user, and the occurrence date and time information can be replaced when otherwise inputted by a user, wherein the received data is displayed on a confirmation screen or announced from a speaker of the information terminal accessible by the user, and in response to a user selection of a confirmation option on the confirmation screen or communication via voice to the information terminal, the database is updated based on the received data.

2. The information processing system according to claim 1, wherein the processor is further configured to:

register predetermined words or symbols in the database, and extract the nickname of the article by dividing the remaining character strings by the predetermined words or symbols, wherein the rules defined for the user comprise user-specific words or symbols for dividing sentences in advance.

3. The information processing system according to claim 1, wherein the processor is further configured to:

recognize a character string representing field of information about the article entered after the nickname of the article in the sentence;

extract following content of the field; and record the content of the field related to the article corresponding to the nickname in the database.

4. The information processing system according to claim 1, wherein the processor is further configured to:

search for the plurality of predetermined character strings representing the intentions of the user from the sentence;

extract character strings dependent on each intention from each of the character strings before or after the plurality of predetermined character strings representing the intentions;

separate the sentence according to each of the intentions; and associate the character strings in the divided sentences with the tables of types corresponding to the intentions of the user in the database respectively, according to the rule defined in advance for the user.

5. The information processing system according to claim 1, wherein the processor is further configured to:

convert a character string representing a date after the nickname of the article in the sentence for a purchase record or an inventory check into date data;

record the converted date data as a target consumption deadline in the corresponding table in the database; and send information for displaying a list of target consumption deadline order of the articles to the information terminal accessible by the user.

6. The information processing system according to claim 1, wherein the processor is further configured to:

in response to a subject consumer owning a plurality of articles of the same article item, calculate a recommended consumption deadline for each article of the plurality of articles from (i) a shortest allowable consumption interval, the shortest allowable consumption interval comprising an interval at which the subject consumer consumes the article item, and (ii) a target consumption deadline for each article item, and the target consumption deadline is able to be different for each article; and in response to an input result to the information terminal by the user, send information for displaying the recommended consumption deadline for each article to the information terminal accessible by the user.

7. The information processing system according to claim 1, wherein:

in response to a subject consumer owning a plurality of articles of the same article item, the processor is further configured to calculate a storable period of an article from a relationship between a consumption deadline and an acquisition date;

further calculate a maximum storable quantity of the articles to be kept for a subject consumer from a shortest allowable consumption interval, which is an interval at which the subject consumer consumes the article item; and send information about the maximum storable quantity of the articles to the information terminal accessible by the user.

8. The information processing system according to claim 1, wherein the processor is further configured to, in response to an input result to the information terminal by the user, record data of an article for a spot and a class in the database; and send information for displaying an inventory list of the article for the spot or the class to the information terminal accessible by the user.

9. The information processing system according to claim 1, wherein the processor is further configured to, in response to an input result to the information terminal by the user, record data of an article for a store or a brand in the database;

set a flag to the article data indicating a subject consumer is planning to purchase the article; and send information to the information terminal accessible by the user to display the article planned to be purchased by the subject consumer according to the store or the brand.

10. The information processing system according to claim 1, wherein the processor is further configured to, in response to an input result to the information terminal by the user, record data of an article for each store or brand in the database;

refer to information about the article accumulated in a knowledge base according to an inventory status of the article of a subject consumer recorded in the database; and send information about recommended article to the information terminal accessible by the user.

11. The information processing system according to claim 1, wherein the processor is further configured to, based on an input by the user, associate a menu with article data;

in response to the menu name input instead of the nickname of the article by the user, collectively update data of a plurality of articles associated with the menu;

in response to an input result to the information terminal by the user, search a menu from nickname of associated article, or search for associated article from a menu name; and send a result of the search to the information terminal accessible by the user.

12. The information processing system according to claim 1, wherein the processor is further configured to:

specify a substance to be managed based on an input result to the information terminal by the user;

calculate an amount of the substance included in an article consumed by a subject consumer from a description regarding an amount of the article input by the user;

perform an analysis of a correlation between an intake amount of the substance and physical condition of the user; and send a result of the analysis to the information terminal accessible by the user.

13. The information processing system according to claim 12, wherein the processor is further configured to calculate estimated cumulative amounts of the specific substance at each time point in a body of the subject consumer.

14. The information processing system according to claim 12, wherein the processor is further configured to predict physical condition of the subject consumer when the intake amount of the specific substance is increased or decreased by machine learning based on at least one of the subject consumer's past data or data stored in a knowledge base.

15. The information processing system according to claim 1, wherein the processor is further configured to:

convert, in response to a character string representing a date and a time before the character string representing the intention in the sentence input by the user, the character string into date and time data;

record the converted date and time data in the corresponding table of the database, in accordance with the intention of the user, as an occurrence date and time of a life event of a subject consumer, instead of the input time of the sentence input by the user; and send information about the life event of the subject consumer for display on the information terminal accessible by the user.

16. The information processing system according to claim 1, wherein the processor is further configured to:

calculate target consumption quantity of the article for a period, based on an input of the user in advance to set a target consumption pace for an article to be managed;

compare, based on an input status of character strings in the sentence representing a nickname and a consumption quantity of an article consumed by a subject consumer to the information terminal by the user, an actual consumption result with the target consumption pace to obtain a comparison result; and send the comparison result to the information terminal accessible by the user.

17. The information processing system according to claim 1, wherein the processor is further configured to:

calculate a cost of consumption for a period of time by recording a purchase price for articles in the database and assigning the recorded purchase price to consumption events during the period of time.

18. The information processing system according to claim 1, wherein the processor is further configured to:

recognize a character string representing a replacement, which is entered immediately after a nickname of an article in the sentence, and replace the nickname by an immediately following nickname.

19. The information processing system according to 1, wherein the processor is further configured to obtain a physical condition level value comprising a value digitized in time series so as to represent a transition of degree of good or poor physical condition based on the data of the physical condition event.

20. The information processing system according to 19, wherein the processor is further configured to extract the lifestyle habit item being the most probable cause of the physical condition from the database by determining a score representing magnitude of an effect of each the lifestyle habit item in the analysis target group at the time of the physical condition event on the physical condition, using the physical condition level value at the time of the physical condition event and the latest possibility degree values for the respective lifestyle habit item in the analysis target group corresponding to the lifestyle habit event extracted as an analysis target within the observation time.

21. The information processing system according to 20 wherein the processor is further configured to:

determine the latest score by obtaining statistics of the past scores for each lifestyle habit item; and extract the lifestyle habit item being the most probable cause of the physical condition from the database.

22. The information processing system according to 19, wherein the processor is further configured to send data to the information terminal accessible by the user, based on a prior setting, for displaying periodically aggregated physical condition level values as a graph representing a trend in the physical condition of a subject consumer.

23. The information processing system according to 1, wherein in response to the user inputting a character string related to a specific lifestyle habit event for a lifestyle habit event having previously occurred, the processor is further configured to:

extract data of the lifestyle habit event including the input character string, and data of a physical condition event within a predetermined time set by the user after a recorded occurrence time of the extracted lifestyle habit event; and send the data to the information terminal accessible by the user.

24. The information processing system according to 1, wherein the processor is further configured to:

refer to information of other consumers accumulated in a knowledge base;

analyze a correlation between data on the lifestyle habit event and data on the physical condition event based on the input by the user; and send to the information terminal accessible by the user, on the basis of an analysis result, information about the lifestyle habit item affecting the physical condition of a subject consumer.

25. The information processing system according to 1, wherein the processor is further configured to:

refer to the information of other consumers accumulated in a knowledge base; and send to the information terminal accessible by the user, prediction timing at which a physical condition of a subject consumer will be affected after the lifestyle habit event of the subject consumer relating to the specific lifestyle habit item.

26. The information processing system according to 1, wherein the data of the physical condition event input by the user is based on an arbitrary numerical value input by the user each time to represent a state of the physical condition of a subject consumer.

27. The information processing system according to 1, wherein the processor is further configured to divide the observation time according to state of occurrences of a plurality of the physical condition events in response to a plurality of physical condition events occurring within the observation time;

extract the lifestyle habit event that occurred within the respective divided observation time; and associate the lifestyle habit item corresponding to the lifestyle habit event in the separate analysis target group for the respective physical condition event.

28. The information processing system according to 1, wherein a rule provides that the same kind of physical condition event is counted only once within a certain time period, and the processor is further configured to determine the physical condition event to be an analysis target by giving priority to a physical condition event of higher level in response to a plurality of physical condition events being recorded within a certain time period;

extract the lifestyle habit event that occurred within the observation time with reference to the recorded occurrence time of the physical condition event; and associate the lifestyle habit item corresponding to the lifestyle habit event in the analysis target group for analyzing the cause of the physical condition event.

29. The information processing system according to 1, wherein the lifestyle habit comprises a meal content in response to a subject consumer using a restaurant or a ready-made food, and the processor is further configured to treat the meal content of the subject consumer as the lifestyle habit item in response to the user inputting the meal content comprising at least one of the store name and the menu name.

30. The information processing system according to 1, wherein a physical condition feature of a subject consumer is registered in advance, and the processor is further configured to distinguish data relating to a feature of the physical condition event that is input together with the registered physical condition feature; and in response to an input result to the information terminal by the user, extract the lifestyle habit item causing the physical condition of the feature to be analyzed from the database.

31. An information processing system comprising:

a memory; and a processor in communication with the memory configured to:

receive a sentence related to a virtual item input according to rules defined for a user;

identify an intention of the user by recognizing a predetermined character string of a plurality of predetermined character strings in the sentence for directing an action to a database;

extract a nickname of the virtual item by recognizing a predetermined character string of a plurality of predetermined character strings from remaining character string in the sentence;

select, based on the identified intention of the user, a table of a type corresponding to the intention of the user from a plurality of tables of types;

extract data on the user-specific virtual item by associating the nickname of the virtual item extracted from the sentence with the nickname of the virtual item registered for the user in the selected table; and collectively update the database, wherein the rules defined for the user comprise (i) registering a user-specific character string representing the intention of the user for directing an action to the database in advance, (ii) registering the nickname, the nickname comprising a keyword for the user-specific virtual item in the database in advance, and (iii) types of intention of the user including an addition record or an application record of virtual items, and wherein the processor is further configured to receive data of a lifestyle habit event comprising an event relating to a state of the lifestyle habit, and a physical condition event comprising an event related to a state of the physical condition including occurrence date and time information of each event on a basis of an input by a user to an information terminal accessible by the user;

update a database based on the received data;

extract, with respect to the data of the physical condition event, the lifestyle habit event that occurred within an observation time on a basis of the occurrence time of the physical condition event;

associate a lifestyle habit item corresponding to the lifestyle habit event in an analysis target group for analyzing a cause of the physical condition event;

update a possibility degree value corresponding to the lifestyle habit item in the analysis target group from a most recent possibility degree value based on a past analysis result for the lifestyle habit item in the analysis target group;

extract the lifestyle habit item being the most probable cause of the physical condition from the database based on the result; and send advice to the information terminal accessible by the user, wherein:

the lifestyle habit item comprises a type of the lifestyle habit, the data of the lifestyle habit event includes information on the lifestyle habit item, the possibility degree value comprises a numerical value indicating a degree of possibility that the lifestyle habit item is a cause of the physical condition event, the observation time comprises a time set for observing occurrences of the physical condition event after the lifestyle habit event, the occurrence date and time information is entered as a timestamp representing input date and time by a user, and the occurrence date and time information can be replaced when otherwise inputted by a user, wherein the received data is displayed on a confirmation screen or announced from a speaker of the information terminal accessible by the user, and in response to a user selection of a confirmation option on the confirmation screen or communication via voice to the information terminal, the database is updated based on the received data.

32. A method of information processing in an electronic device comprising a memory, and a processor in communication with the memory, the method comprising:

receiving a sentence related to an article input according to rules defined for a user;

identifying an intention of the user by recognizing a predetermined character string of a plurality of predetermined character strings in the sentence for instructing operation to a database;

extracting a nickname of the article by recognizing a predetermined character string of a plurality of predetermined character strings from remaining character string in the sentence;

selecting, based on the identified intention of the user, a table of a type corresponding to the intention of the user from a plurality of tables of types;

extracting data on the user-specific article by associating the nickname of the article extracted from the sentence with the nickname of the article registered for the user in the selected table; and collectively updating the database, wherein:

the rules defined for the user comprise (i) registering a user-specific character string representing the intention of the user for directing an action to the database in advance, (ii) registering the nickname, the nickname comprising a keyword for the user-specific article in the database in advance, and (iii) types of intention of the user including an acquisition record or a consumption record of articles, and wherein the method further comprising: receiving data of a lifestyle habit event comprising an event relating to a state of the lifestyle habit, and a physical condition event comprising an event related to a state of the physical condition including occurrence date and time information of each event occurring from time to time on a basis of an input by a user to an information terminal accessible by the user;

updating a database based on the received data;

extracting, with respect to the data of the physical condition event, the lifestyle habit event that occurred within an observation time on a basis of the occurrence time of the physical condition event;

associating a lifestyle habit item corresponding to the lifestyle habit event in an analysis target group for analyzing a cause of the physical condition event;

updating a possibility degree value corresponding to the lifestyle habit item in the analysis target group from a most recent possibility degree value based on a past analysis result for the lifestyle habit item in the analysis target group;

extracting the lifestyle habit item being the most probable cause of the physical condition from the database based on the result; and send advice to the information terminal accessible by the user, wherein:

the lifestyle habit item comprises a type of the lifestyle habit, the data of the lifestyle habit event includes information on the lifestyle habit item, the possibility degree value comprises a numerical value indicating a degree of possibility that the lifestyle habit item is a cause of the physical condition event, the observation time comprises a time set for observing occurrences of the physical condition event after the lifestyle habit event, the occurrence date and time information is entered as a timestamp representing input date and time by a user, and the occurrence date and time information can be replaced when otherwise inputted by a user, wherein the received data is displayed on a confirmation screen or announced from a speaker of the information terminal accessible by the user, and in response to a user selection of a confirmation option on the confirmation screen or communication via voice to the information terminal, the database is updated based on the received data.

33. A non-transitory computer-readable recording medium in which a program is stored, which when executed by an electronic device comprising a memory, and a processor, causes the electronic device to perform operations comprising:

receiving a sentence related to an article input according to rules defined for a user;

identifying an intention of the user by recognizing a predetermined character string of a plurality of predetermined character strings in the sentence for instructing operation to a database;

extracting a nickname of the article by recognizing a predetermined character string of a plurality of predetermined character strings from remaining character string in the sentence;

selecting, based on the identified intention of the user, a table of a type corresponding to the intention of the user from a plurality of tables of types;

extracting data on the user-specific article by associating the nickname of the article extracted from the sentence with the nickname of the article registered for the user in the selected table; and collectively updating the database, wherein:

the rules defined for the user comprise (i) registering a user-specific character string representing the intention of the user for directing an action to the database in advance, (ii) registering the nickname, the nickname comprising a keyword for the user-specific article in the database in advance, and (iii) the types of intention of the user including an acquisition record or a consumption record of articles, and wherein operations of the electronic device further comprising:

receiving data of a lifestyle habit event comprising an event relating to a state of the lifestyle habit, and a physical condition event comprising an event related to a state of the physical condition including occurrence date and time information of each event occurring from time to time on a basis of an input by a user to an information terminal accessible by the user;

updating a database based on the received data;

extracting, with respect to the data of the physical condition event, the lifestyle habit event that occurred within an observation time on a basis of the occurrence time of the physical condition event;

associating a lifestyle habit item corresponding to the lifestyle habit event in an analysis target group for analyzing a cause of the physical condition event;

updating a possibility degree value corresponding to the lifestyle habit item in the analysis target group from a most recent possibility degree value based on a past analysis result for the lifestyle habit item in the analysis target group;

extracting the lifestyle habit item being the most probable cause of the physical condition from the database based on the result; and send advice to the information terminal accessible by the user, wherein:

the lifestyle habit item comprises a type of lifestyle habit, the data of the lifestyle habit event includes information on the lifestyle habit item, the possibility degree value comprises a numerical value indicating a degree of possibility that the lifestyle habit item is a cause of the physical condition event, and the observation time comprises a time set for observing occurrences of the physical condition event after the lifestyle habit event, the occurrence date and time information is entered as a timestamp representing input date and time by a user, and the occurrence date and time information can be replaced when otherwise inputted by a user, wherein the received data is displayed on a confirmation screen or announced from a speaker of the information terminal accessible by the user, and in response to a user selection of a confirmation option on the confirmation screen or communication via voice to the information terminal, the database is updated based on the received data.

* * * * *